US012797384B2

(12) United States Patent
Chen et al.

(10) Patent No.: US 12,797,384 B2
(45) Date of Patent: Nov. 17, 2026

(54) METHODS AND MATERIALS FOR INHIBITING NICOTINAMIDE PHOSPHORIBOSYLTRANSFERASE ACTIVITY

(71) Applicant: University of Pittsburgh—Of the Commonwealth System of Higher Education, Pittsburgh, PA (US)

(72) Inventors: Beibei Chen, Pittsburgh, PA (US); Toren Finkel, Pittsburgh, PA (US); Yuan Liu, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 621 days.

(21) Appl. No.: 18/022,642

(22) PCT Filed: Nov. 19, 2021

(86) PCT No.: PCT/US2021/060115

§ 371 (c)(1),
(2) Date: Feb. 22, 2023

(87) PCT Pub. No.: WO2022/109285

PCT Pub. Date: May 27, 2022

(65) Prior Publication Data

US 2023/0321086 A1 Oct. 12, 2023

Related U.S. Application Data

(60) Provisional application No. 63/116,624, filed on Nov. 20, 2020.

(51) Int. Cl.

| | |
|---|---|
| ***A61K 31/498*** | (2006.01) |
| ***A61K 31/4985*** | (2006.01) |
| ***A61K 31/501*** | (2006.01) |
| ***A61K 31/513*** | (2006.01) |
| ***A61K 31/5377*** | (2006.01) |
| ***A61K 31/538*** | (2006.01) |

(52) U.S. Cl.

CPC ........ *A61K 31/498* (2013.01); *A61K 31/4985* (2013.01); *A61K 31/501* (2013.01); *A61K 31/513* (2013.01); *A61K 31/5377* (2013.01); *A61K 31/538* (2013.01)

(58) Field of Classification Search

CPC .................................................. A61K 31/4985
USPC ........................................................... 514/230
See application file for complete search history.

(56) References Cited

U.S. PATENT DOCUMENTS

| | | | |
|---|---|---|---|
| 5,304,121 | A | 4/1994 | Sahatjian |
| 5,886,026 | A | 3/1999 | Hunter et al. |
| 6,099,562 | A | 8/2000 | Ding et al. |
| 6,803,031 | B2 | 10/2004 | Rabinowitz et al. |
| 2016/0229835 | A1 | 8/2016 | Burkholder et al. |
| 2017/0174704 | A1 | 6/2017 | Gigstad et al. |
| 2019/0031686 | A1 | 1/2019 | Bair et al. |

FOREIGN PATENT DOCUMENTS

| | | | |
|---|---|---|---|
| WO | WO-2015161142 A1 * | 10/2015 | .............. A61P 43/00 |
| WO | WO 2015/179759 | 11/2015 | |

OTHER PUBLICATIONS

Galli et al. "Recent Advances in NAMPT Inhibitors: A Novel Immunotherapic Strategy," Frontiers in Pharmacology, May 2020, 11:1-20.
Illum, "Is nose-to-brain transport of drugs in man a reality?" J. Pharm. Pharmacol., Jan. 2004, 56(1):3-17.
Illum, "Transport of drugs from the nasal cavity to the central nervous system," Eur. J. Pharm. Sci., Jul. 2000, 11(1):1-18.
PCT International Preliminary Report on Patentability in International Appln. No. PCT/US2021/060115, mailed on Jun. 1, 2023, 5 pages.
PCT International Search Report and Written Opinion in International Appln. No. PCT/US2021/060115, mailed on Feb. 8, 2022, 6 pages.
Revollo et al., "The regulation of nicotinamide adenine dinucleotide biosynthesis by Nampt/PBEF/visfatin in mammals," Current Opinion in Gastroenterology, Mar. 2007, 23(2):164-70.
Samal et al., "Cloning and characterization of the cDNA encoding a novel human pre-B-cell colony-enhancing factor," Mol. Cell. Biol., Feb. 1994, 14(2):1431-1437.

* cited by examiner

*Primary Examiner* — Jeffrey H Murray
*Assistant Examiner* — Rilla Marie Samsell
(74) *Attorney, Agent, or Firm* — Fish & Richardson P.C.

(57) ABSTRACT

This document provides compounds that are inhibitors of NAMPT activity, as well as the methods of using such compounds for treating diseases and conditions such as cancer, inflammatory conditions, autoimmune conditions, and conditions characterized by acute or sub-acute neuronal injury.

19 Claims, No Drawings

METHODS AND MATERIALS FOR INHIBITING NICOTINAMIDE PHOSPHORIBOSYLTRANSFERASE ACTIVITY

CLAIM OF PRIORITY

This application is a National Stage application under 35 U.S.C. § 371 of International Application No. PCT/US2021/060115, having an International Filing Date of Nov. 19, 2021, which claims priority to U.S. Patent Application Ser. No. 63/116,624, filed on Nov. 20, 2020, the entire contents of which are hereby incorporated by reference.

FEDERALLY SPONSORED RESEARCH AND DEVELOPMENT

This invention was made with government support under grant number HL139860 awarded by National Institutes of Health (NIH). The government has certain rights in the invention.

TECHNICAL FIELD

This document relates to methods and materials for inhibiting nicotinamide phosphoribosyltransferase (NAMPT) activity. For example, this document provides compounds (e.g., organic compounds) having the ability to inhibit NAMPT activity within cells and/or within a mammal, formulations containing one or more compounds having the ability to inhibit NAMPTactivity within cells and/or within a mammal, methods for making one or more compounds having the ability to inhibit NAMPTactivity within cells and/or within a mammal, methods for inhibiting NAMPTactivity within cells and/or within a mammal, and methods for treating mammals (e.g., humans) having a condition responsive to inhibition of NAMPT activity.

BACKGROUND

Intracellularily, the enzyme NAMPT is a rate-limiting enzyme of the nicotinamide adenine dinucleotide (NAD+) salvage pathway that converts nicotinamide to nicotinamide mononucleotide (NMN) and forms most of the NAD+ found in mammals (Revollo et al., *Current Opinion in Gastroenterology,* 23(2):164-70 (2007)). Intracellular NAMPT also catalyzes the synthesis of NMN from phosphoribosyl pyrophosphate (PRPP) in the presence of ATP (Galli et al., *Frontiers in Pharmacology,* 11:656 (2020)). In some cases, extracellular NAMPT can act as a cytokine involved in promoting B cell maturation and inhibiting neutrophil apoptosis (Samal et al., *Mol. Cell. Biol.,* 14(2):1431-7 (1994)).

SUMMARY

This document provides methods and materials for inhibiting NAMPT activity. For example, the document provides compounds (e.g., organic compounds) having the ability to inhibit NAMPT activity within cells and/or within a mammal, formulations containing one or more compounds having the ability to inhibit NAMPT activity within cells and/or within a mammal, methods for making one or more compounds having the ability to inhibit NAMPT activity within cells and/or within a mammal, methods for making formulations containing one or more compounds having the ability to inhibit NAMPT activity within cells and/or within a mammal, methods for inhibiting NAMPT activity within cells and/or within a mammal, and methods for treating mammals (e.g., humans) having a condition responsive to inhibition of NAMPT activity. Suitable examples of conditions responsive to inhibition of NAMPT activity within cells and/or within the mammal include cancer, disorders characterized by dysregulation of the immune system, inflammatory conditions, and acute neuronal injury.

As described herein, the methods and materials provided herein can be used to inhibit NAMPT activity within cells in vitro, in vivo, or ex vivo. In some cases, the compounds provided herein can be used to treat mammals (e.g., humans) having a disease, disorder, or condition associated with excess activation of an NAMPT polypeptide within cells and/or within the mammal and/or associated with excess $NAD^+$ formation within cells and/or within the mammal. In some cases, one or more compounds provided herein can be used to treat mammals (e.g., humans) having a disease, disorder, or condition that is responsive to inhibition of NAMPT activity.

In one general aspect, the present disclosure provides a method for inhibiting NAMPT activity within a mammal, wherein said method comprises administering, to said mammal, an effective amount of a compound of Formula (I):

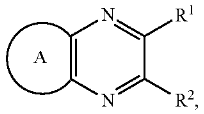

(I)

or a pharmaceutically acceptable salt thereof, wherein ring A, $R^1$, and $R^2$ are as described herein.

In another general aspect, the present disclosure provides a pharmaceutical composition comprising a compound of Formula (I), or a pharmaceutically acceptable salt thereof, and a pharmaceutically acceptable carrier.

In yet another general aspect, the present disclosure provides a compound of Formula (II):

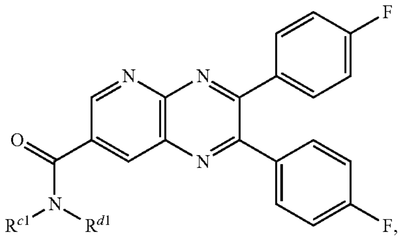

(II)

or a pharmaceutically acceptable salt thereof, wherein $R^{c1}$ and $R^{d1}$ are as described herein.

In yet another general aspect, the present disclosure provides a compound of Formula (III):

(III)

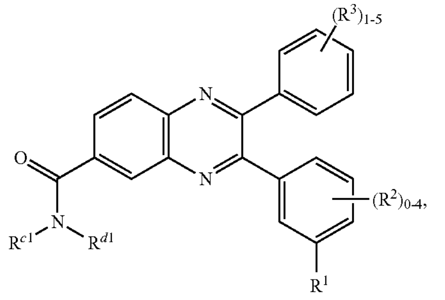

or a pharmaceutically acceptable salt thereof, wherein $R^{c1}$, $R^{d1}$, $R^1$, $R^2$, and $R^3$ are as described herein.

In yet another general aspect, the present disclosure provides a compound of Formula (IV):

(IV)

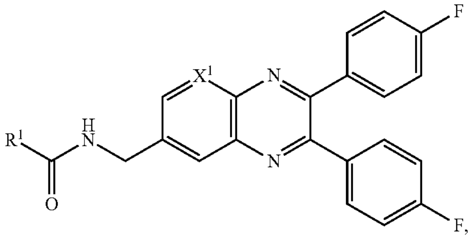

or a pharmaceutically acceptable salt thereof, wherein $R^1$ are as described herein.

In yet another general aspect, the present disclosure provides a compound of Formula (V):

(V)

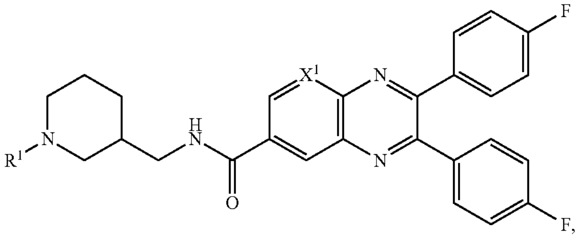

or a pharmaceutically acceptable salt thereof, wherein $X^1$ and $R^1$ is as described herein.

In yet another general aspect, the present disclosure provides a compound of Formula (VI):

(VI)

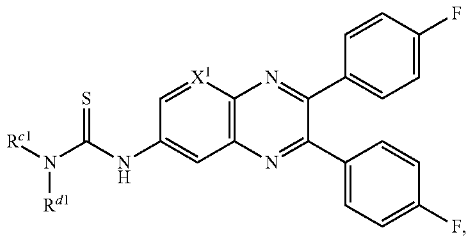

or a pharmaceutically acceptable salt thereof, wherein $X^1$, $R^{c1}$, and $R^{d1}$ are as described herein.

In yet another general aspect, the present disclosure provides a pharmaceutical composition comprising a compound of any one of the Formulae (II)-(VI), or a pharmaceutically acceptable salt thereof, and a pharmaceutically acceptable carrier.

In yet another general aspect, the present disclosure provides a method for inhibiting NAMPT activity within a mammal, wherein said method comprises administering, to said mammal, an effective amount of a compound of any one of the Formulae (II)-(VI), or a pharmaceutically acceptable salt thereof, and a pharmaceutically acceptable carrier.

In yet another general aspect, the present disclosure provides a method of treating a mammal having a disease, disorder, or condition responsive to inhibiting NAMPT activity within the mammal, wherein said method comprises administering, to said mammal, any one of the compounds described herein, or a pharmaceutical composition comprising same.

In some embodiments, the mammal is human. In some embodiments, the disease, disorder, or condition is selected from a cancer, an inflammatory condition, an autoimmune condition, and an acute or sub-acute neuronal injury.

In some embodiments, the method comprises treating a mammal having a solid tumor or cancer involving T cells, B cells, or other circulating cells. In some embodiments, the method comprises treating a mammal having a disorder of immunity or an inflammatory condition. For example, the method can comprise treating a mammal having multiple sclerosis, systemic lupus erythematosus, or rheumatoid arthritis. In some embodiments, the method can comprise treating a mammal having a disorder characterized by traumatic injury to the central or peripheral nervous system (e.g., a spinal cord injury, a traumatic brain injury, or a chemotherapeutic-induced neuropathy).

In yet another general aspect, the present disclosure provides a method for inhibiting NAMPT activity within a mammal, wherein said method comprises administering, to said mammal, any one of the compounds described herein or a pharmaceutical composition comprising same.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

This document provides methods and materials for inhibiting NAMPT activity. For example, the document provides compounds (e.g., organic compounds) having the ability to inhibit NAMPT activity within cells and/or within a mammal, formulations containing one or more compounds having the ability to inhibit NAMPT activity within cells and/or within a mammal, methods for making one or more compounds having the ability to inhibit NAMPT activity within cells and/or within a mammal, methods for making formulations containing one or more compounds having the ability to inhibit NAMPT activity within cells and/or within a mammal, methods for inhibiting NAMPT activity within cells and/or within a mammal, and methods for treating mammals (e.g., humans) having a condition responsive to an inhibition of NAMPT activity. Suitable examples of conditions responsive to inhibition of NAMPT activity within cells and/or within a mammal include, without limitation, cancer, autoimmune conditions, inflammatory conditions, and acute or sub-acute neuronal injuries. For example, a compound (e.g., an organic compound) provided herein can be used to inhibit or reduce tumor growth and/or metastasis.

Methods of Treatment Using One or More Inhibitors of NAMPT Activity

In some cases, this document provides methods for inhibiting NAMPT activity within a cell by contacting the cell with one or more compounds provided herein (e.g., a compound set forth in any one of the Formulae (I)-(VI), or a pharmaceutically acceptable salt thereof).

In some cases, methods for inhibiting NAMPT activity within cells can be performed in vivo. For example, one or more compounds provided herein (e.g., a compound set forth in any one of the Formulae (I)-(VI), or a pharmaceutically acceptable salt thereof) can be administered to a mammal (e.g., a human) to inhibit NAMPT activity within cells within that mammal. In some cases, methods for inhibiting NAMPT activity within cells can be performed in vitro. For example, one or more compounds provided herein (e.g., a compound set forth in any one of the Formulae (I)-(VI), or a pharmaceutically acceptable salt thereof) can be added to a cell culture containing cells (e.g., human cells) to inhibit NAMPT activity within those cells. In some cases, such intervention can improve the quality of the cell while in culture or subsequently.

In some cases, this document provides methods for inhibiting NAMPT activity within a mammal by administering one or more compounds provided herein (e.g., a compound set forth in any one of the Formulae (I)-(VI), or a pharmaceutically acceptable salt thereof) to the mammal. For example, one or more cytokine activities of NAMPT can be inhibited within a mammal by administering one or more compounds provided herein (e.g., a compound set forth in any one of the Formulae (I)-(VI), or a pharmaceutically acceptable salt thereof) to the mammal.

This document also provides methods for treating diseases, disorders, and conditions in a mammal by administering one or more compounds provided herein (e.g., a compound set forth in any one of the Formulae (I)-(VI), or a pharmaceutically acceptable salt thereof) to a mammal in need thereof. In some cases, the disease, disorder, or condition being treated can be a disease, disorder, or condition that is responsive to inhibiting NAMPT activity within cells and/or within the mammal. In some cases, the disease, disorder, or condition being treated can be a disease, disorder, or condition that is associated with excess NAMPT activity within the mammal.

Examples of diseases, disorders, and conditions that can be treated with one or more compounds provided herein include, without limitation, cancers, inflammatory conditions, autoimmune conditions, and acute or sub-acute neuronal injuries.

Suitable examples of cancers that can be treated with one or more compounds provided herein include, without limitation, prostate cancer, pancreatic cancer, ovarian cancer, breast cancer, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastroesophageal cancer, gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma, hepatobiliary cancer); leiomyosarcoma (LMS); mastocytosis (e.g., systemic mastocytosis); muscle cancer; myelodysplastic syndrome (MD); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasmlungrectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Suitable examples of inflammatory conditions and disorders associated with inflammation that can be treated with one or more compounds provided herein include, without limitation, asthma, chronic obstructive lung disease, pulmonary fibrosis, pneumonitis (e.g., hypersensitivity pneumonitis and radiation pneumonitis), pneumonia, cystic fibrosis, psoriasis, arthritis, rheumatoid arthritis, rhinitis, pharyngitis, cystitis, prostatitis, dermatitis, allergy (e.g., hay fever), nephritis, conjunctivitis, encephalitis, meningitis, opthalmitis, uveitis, pleuritis, pericarditis, myocarditis, atherosclerosis, diabetes, osteoarthritis, psoriatic arthritis, autoimmune diseases or conditions, inflammatory bowel disease (e.g., Crohn's disease or ulcerative colitis), colitis, sepsis, vasculitis, bursitis, connective tissue disease, systemic lupus erythematosis (SLE), polymyalgia rheumatica, scleroderma, Wegener's granulomatosis, temporal arteritis, vasculitis, cryoglobulinemia, multiple sclerosis, and edema.

Suitable examples of neuronal injury that can be treated with one or more compounds provided herein include, without limitation, stroke, brain and/or spinal cord trauma, hypoglycemic coma, prolonged epileptic seizures, mild and severe traumatic brain injury, and/or nerve impairment cased by exposure to toxins (e.g., chemotherapeutic agents).

In some cases, provided herein are methods for treating a cancer (e.g., any one of the cancers described herein) in a mammal (e.g., human) by administering one or more compounds provided herein (e.g., a compound set forth in any one of the Formulae (I)-(VI), or a pharmaceutically acceptable salt thereof) to a mammal in need thereof.

In some cases, provided herein are methods for treating inflammation (e.g., any one of the inflammation disorders described herein) in a mammal (e.g., human) by administering one or more compounds provided herein (e.g., a compound set forth in any one of the Formulae (I)-(VI), or a pharmaceutically acceptable salt thereof) to a mammal in need thereof.

In some cases, provided herein are methods for treating autoimmune disease (e.g., any one of the autoimmune diseases described herein) in a mammal (e.g., human) by administering one or more compounds provided herein (e.g., a compound set forth in any one of the Formulae (I)-(VI), or a pharmaceutically acceptable salt thereof) to a mammal in need thereof.

In some cases, provided herein are methods for treating neuronal injury (e.g., any one of the acute or sub-acute neuronal injuries or diseases described herein) in a mammal (e.g., human) by administering one or more compounds provided herein (e.g., a compound set forth in any one of the Formulae (I)-(VI), or a pharmaceutically acceptable salt thereof) to a mammal in need thereof.

In some cases, one or more compounds provided herein (e.g., a compound set forth in any one of the Formulae (I)-(VI), or a pharmaceutically acceptable salt thereof) can be used as described herein (e.g., to inhibit NAMPT activity within cells and/or within a mammal and/or to treat a disease, disorder, or condition as described herein) as the sole active ingredient(s). For example, a composition containing a compound set forth in any one of the Formulae (I)-(VI), or a pharmaceutically acceptable salt thereof, can lack any other active ingredients that inhibit NAMPT activity within cells and/or a mammal. In some cases, a composition containing a compound set forth in any one of the Formulae (I)-(VI), or a pharmaceutically acceptable salt thereof, can lack any other active ingredients that are effective to treat a disease, disorder, or condition as described herein.

Therapeutic Compounds

As described herein, any one or more of the compounds provided herein (a) can be used to inhibit NAMPT activity within cells and/or within a mammal and/or (b) can be used to treat (or prevent) a disease, disorder, and condition in a mammal (e.g., a human) as described herein.

Formula (I)

In some embodiments, the present disclosure provides a compound of Formula (I):

(I)

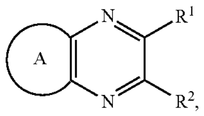

or a pharmaceutically acceptable salt thereof, wherein ring A, $R^1$, and $R^2$ are as described herein.

In some embodiments of Formula (I):

ring A is selected from $C_{3-8}$ cycloalkyl, 4-10 membered heterocycloalkyl, $C_{6-10}$ aryl, and 5-10 membered heteroaryl, each of which is optionally substituted with 1, 2, or 3 substituents independently selected from $R^A$;

each $R^A$ is independently selected from $Cy^1$, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(NR^{e1})NR^{c1}R^{d1}$, $C(NR^{e1})NR^{c1}OR^{a1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}C(S)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^8$;

each $R^8$ is independently selected from $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, 3, 4, or 5 substituents independently selected from $R^g$;

$R^1$ is selected from $R^9$, $OR^9$, $N(R^N)R^9$, and $S(O)_2R^9$;

$R^2$ is selected from $R^9$, $OR^9$, $N(R^N)R^9$, and $S(O)_2R^9$;

$R^N$ is selected from H, $C_{1-4}$ alkyl, and $C_{1-4}$ haloalkyl;

each $R^9$ is independently selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{e1}$ is selected from H, $OR^{a1}$, $NR^{c1}R^{d1}$, and $C_{1-4}$ haloalkyl;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, when the compound of Formula (I) has formula (i):

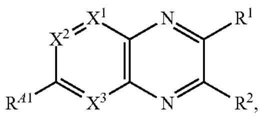

(i)

in which $X^1$, $X^2$, and $X^3$ are each independently selected from N, CH, and $CR^A$; and $R^{A1}$ is selected from $C(O)R^{b1}$ and $C(O)NR^{c1}R^{d1}$, then (i) at least one of $X^1$, $X^2$, and $X^3$ is N; or (ii) at least one of $R^1$ and $R^2$ is selected from $C_{1-6}$ haloalkyl and $S(O)_2R^9$.

In some embodiments, when the compound of Formula (I) has formula (i), then at least one of $X^1$, $X^2$, and $X^3$ is N. In some aspects of these embodiments, $X^1$ is N. In some aspects of these embodiments, $X^2$ is N. In some aspects of these embodiments, $X^3$ is N.

In some embodiments, when the compound of Formula (I) has formula (i), then at least one of $R^1$ and $R^2$ is selected from $C_{1-6}$ haloalkyl and $S(O)_2R^9$. In some aspects of these embodiments, $R^1$ is $C_{1-6}$ haloalkyl. In some aspects of these embodiments, $R^1$ is $S(O)_2R^9$. In some aspects of these embodiments, $R^2$ is $C_{1-6}$ haloalkyl. In some aspects of these embodiments, $R^2$ is $S(O)_2R^9$.

In some embodiments, ring A is $C_{3-8}$ cycloalkyl, optionally substituted with 1, 2, or 3 substituents independently selected from $R^A$.

In some embodiments, ring A is 4-10 membered heterocycloalkyl, optionally substituted with 1, 2, or 3 substituents independently selected from $R^A$.

In some embodiments, ring A is $C_{6-10}$ aryl, optionally substituted with 1, 2, or 3 substituents independently selected from $R^A$.

In some embodiments, ring A is 5-10 membered heteroaryl, optionally substituted with 1, 2, or 3 substituents independently selected from $R^A$.

In some embodiments, $R^A$ is selected from halo, CN, $NO_2$, $C_{1-6}$ alkyl, $C_{1-6}$ haloalkyl, $OR^{a1}$, $C(O)NR^{c1}R^{d1}$, $C(O)OR^{a1}$, and $NR^{c1}R^{d1}$ wherein said $C_{1-6}$ alkyl is optionally substituted with 1 or 2 independently selected $R^7$.

In some embodiments, $R^A$ is selected from halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^A$ is selected from halo, $C_{1-6}$ alkyl, and $C_{1-6}$ alkoxy.

In some embodiments, $R^A$ is $Cy^1$.

In some embodiments, $R^A$ is $C(O)NR^{c1}R^{d1}$.

In some embodiments, $R^A$ is $C(O)OR^{a1}$.

In some embodiments, $R^A$ is $C_{1-6}$ alkyl substituted with $R^7$.

In some embodiments, $R^7$ is selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $S(O)_2R^{b1}$, and $S(O)_2NR^{c1}R^{d1}$.

In some embodiments, $R^7$ is selected from CN, $NO_2$, OH, $C_{1-6}$ alkoxy, $C_{1-6}$ haloalkoxy, amino, $C_{1-6}$ alkylamino, and di($C_{1-6}$ alkyl)amino.

In some embodiments, $Cy^1$ is $C_{6-10}$ aryl, optionally substituted with 1, 2, or 3 substituents independently selected from $R^{Cy1}$.

In some embodiments, $Cy^1$ is $C_{3-10}$ cycloalkyl, optionally substituted with 1, 2, or 3 substituents independently selected from $R^{Cy1}$.

In some embodiments, $Cy^1$ is 5-10 membered heteroaryl, optionally substituted with 1, 2, or 3 substituents independently selected from $R^{Cy1}$.

In some embodiments, $Cy^1$ is 4-10 membered heterocycloalkyl, optionally substituted with 1, 2, or 3 substituents independently selected from $R^{Cy1}$.

In some embodiments, $R^{Cy1}$ is selected from halo, CN, $NO_2$, OH, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^{Cy1}$ is selected from $C_{3-10}$ cycloalkyl, $C_{6-10}$ aryl, 5-10 membered heteroaryl, and 4-10 membered heterocycloalkyl, each of which is optionally substituted with 1, 2, or 3 substituents independently selected from $R^8$.

In some embodiments, $R^8$ is selected from $C_{1-6}$ alkyl, halo, CN, $NO_2$, OH, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^8$ is selected from $C_{3-10}$ cycloalkyl, $C_{6-10}$ aryl, 5-10 membered heteroaryl, and 4-10 membered heterocycloalkyl, each of which is optionally substituted with 1, 2, or 3 substituents independently selected from $R^g$.

In some embodiments, $R^1$ is selected from $R^9$ and $S(O)_2R^9$. In some embodiments, $R^1$ is $R^9$. In some embodiments, $R^1$ is $S(O)_2R^9$. In some embodiments, $R^1$ is $OR^9$. In some embodiments, $R^1$ is $NHR^9$.

In some embodiments, $R^2$ is selected from $R^9$ and $S(O)_2R^9$. In some embodiments, $R^2$ is $R^9$. In some embodiments, $R^2$ is $S(O)_2R^9$. In some embodiments, $R^2$ is $OR^9$. In some embodiments, $R^2$ is $NHR^9$.

In some embodiments, $R^1$ and $R^2$ are both $R^9$.

In some embodiments, $R^1$ is $R^9$ and $R^2$ is $S(O)_2R^9$.

In some embodiments, $R^1$ is $S(O)_2R^9$ and $R^2$ is $R^9$.

In some embodiments, $R^1$ is $R^9$ and $R^2$ is $OR^9$.

In some embodiments, $R^1$ is $R^9$ and $R^2$ is $NHR^9$.

In some embodiments, $R^9$ is selected from $C_{1-6}$ haloalkyl, $C_{6-10}$ aryl, 5-10 membered heteroaryl, and 4-10 membered heterocycloalkyl, each of which is optionally substituted with 1, 2, or 3 substituents independently selected from $R^{10}$.

In some embodiments, $R^9$ is $C_{1-6}$ haloalkyl.

In some embodiments, $R^9$ is $C_{6-10}$ aryl, optionally substituted with 1, 2, or 3 substituents independently selected from $R^{10}$.

In some embodiments, $R^9$ is 5-10 membered heteroaryl, optionally substituted with 1, 2, or 3 substituents independently selected from $R^{10}$.

In some embodiments, $R^9$ is 4-10 membered heterocycloalkyl, optionally substituted with 1, 2, or 3 substituents independently selected from $R^{10}$.

In some embodiments:

$R^1$ is $C_{1-6}$ haloalkyl; and $R^2$ is $C_{6-10}$ aryl, optionally substituted with 1, 2, or 3 substituents independently selected from $R^{10}$.

In some embodiments:

$R^1$ is $C_{1-6}$ haloalkyl; and $R^2$ is 5-10 membered heteroaryl, optionally substituted with 1, 2, or 3 substituents independently selected from $R^{10}$.

In some embodiments:

$R^1$ is $S(O)_2R^9$; and $R^2$ is $C_{6-10}$ aryl, optionally substituted with 1, 2, or 3 substituents independently selected from $R^{10}$.

In some embodiments:

$R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments:

$R^1$ is 5-10 membered heteroaryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments:

$R^1$ is 5-10 membered heteroaryl, optionally substituted with 1, 2, or 3 substituents independently selected from $R^{10}$; and $R^2$ is 5-10 membered heteroaryl, optionally substituted with 1, 2, or 3 substituents independently selected from $R^{10}$.

In some embodiments, $R^{10}$ is selected from halo, CN, $NO_2$, OH, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino; wherein said $C_{1-6}$ alkyl is optionally substituted with 1, 2, or 3 substituents independently selected from $R^{11}$.

In some embodiments, $R^{10}$ is halo (e.g., $R^{10}$ is F).

In some embodiments, $R^{10}$ is selected from $S(O)_2R^{b1}$ and $S(O)_2NR^{c1}R^{d1}$.

In some embodiments, $R^{10}$ is $S(O)_2R^{b1}$.

In some embodiments, $R^{10}$ is $C_{1-6}$ alkyl optionally substituted with 1, 2, or 3 substituents independently selected from $R^{11}$.

In some embodiments, $R^{11}$ is selected from CN, $NO_2$, OH, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^{a1}$, $R^{b1}$, $R^{c1}$, and $R^{d1}$ are independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, or 3 substituents independently selected from $R^g$.

In some embodiments, $R^{c1}$ and $R^{d1}$ together with the N atom to which they are attached form a 4-7 membered heterocycloalkyl, which is optionally substituted with 1, 2, or 3 substituents independently selected from $R^g$.

In some embodiments, the compound of Formula (I) has formula (i), wherein $R^{A1}$ is selected from $Cy^1$, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(NR^{e1})NR^{c1}R^{d1}$, $C(NR^{e1})NR^{c1}OR^{a1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$.

In some embodiments, the compound of Formula (I) has Formula (Ia):

(Ia)

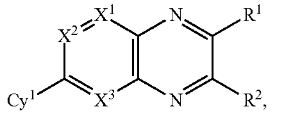

or a pharmaceutically acceptable salt thereof, wherein $X^1$, $X^2$, and $X^3$ are each independently selected from N, CH, and $CR^A$. In some embodiments, not more than two of $X^1$, $X^2$, and $X^3$ are N. In some embodiments, $X^1$ is N. In some embodiments, $X^2$ is N. In some embodiments, $X^3$ is N.

In some embodiments of Formula (Ia):

$X^1$ is selected from N, CH, and $CR^A$;

$X^2$ is selected from CH and $CR^A$; and $X^3$ is selected from CH and $CR^A$.

In some embodiments, $X^1$ is N, and $X^2$ and $X^3$ are independently selected from CH and $CR^A$.

In some embodiments, each $R^A$ is as described herein. In some embodiments, each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, each $R^A$ is independently selected from H, halo, $C_{1-6}$ alkyl, and $C_{1-6}$ alkoxy.

In some embodiments, the compound of Formula (Ia) has formula:

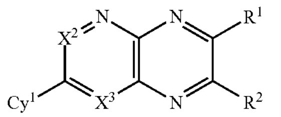

or a pharmaceutically acceptable salt thereof.

In some embodiments, $Cy^1$ is $C_{6-10}$ aryl, optionally substituted with 1, 2, or 3 substituents independently selected from $R^{Cy1}$. In some embodiments, $Cy^1$ is $C_{3-10}$ cycloalkyl, optionally substituted with 1, 2, or 3 substituents independently selected from $R^{Cy1}$. In some embodiments, $Cy^1$ is 4-10 membered heterocycloalkyl, optionally substituted with 1, 2, or 3 substituents independently selected from $R^{Cy1}$. In some embodiments, $Cy^1$ is 5-10 membered heteroaryl, optionally substituted with 1, 2, or 3 substituents independently selected from $R^{Cy1}$.

In some embodiments, $Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$.

In some embodiments, each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$.

In some embodiments, $R^8$ is selected from $OR^{a1}$ and $NR^{c1}R^{d1}$ In some embodiments, $R^8$ is $OR^{a1}$. In some embodiments, $R^8$ is $NR^{c1}R^{d1}$.

In some embodiments:

$R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments:

$R^1$ is $C_{1-6}$ haloalkyl; and $R^2$ is $C_{6-10}$ aryl, optionally substituted with 1, 2, or 3 substituents independently selected from $R^{10}$.

In some embodiments:

$R^1$ is $C_{6-10}$ aryl, optionally substituted with 1, 2, or 3 substituents independently selected from $R^{10}$; and $R^2$ is $C_{1-6}$ haloalkyl.

In some embodiments:

$R^1$ is 5-10 membered heteroaryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments:

$R^1$ is $C_{6-10}$ aryl, optionally substituted with 1, 2, or 3 substituents independently selected from $R^{10}$; and $R^2$ is 5-10 membered heteroaryl, optionally substituted with 1, 2, or 3 substituents independently selected from $R^{10}$.

In some embodiments, the 5-10 membered heteroaryl is thiophene (optionally substituted with 1, 2, or 3 substituents independently selected from $R^{10}$).

In some embodiments, the $C_{6-10}$ aryl is phenyl (optionally substituted with 1, 2, or 3 substituents independently selected from $R^{10}$).

In some embodiments, $R^{10}$ is selected from halo and $S(O)_2R^{b1}$. In some embodiments, $R^{10}$ is halo. In some embodiments, $R^{10}$ is $S(O)_2R^{b1}$. In some aspects of these embodiments, $R^{b1}$ is $C_{1-6}$ alkyl.

In some embodiments of Formula (Ia):

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is phenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{1-6}$ haloalkyl;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is trifluoromethyl;

$R^2$ is phenyl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{6-10}$ aryl, optionally substituted with 1, 2, or 3 substituents independently selected from $R^{10}$; and $R^2$ is $C_{1-6}$ haloalkyl;

each $R^{10}$ is independently selected from halo and $S(O)_2R^{b1}$.

In some embodiments of Formula (Ia):

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is phenyl, optionally substituted with 1, 2, or 3 substituents independently selected from $R^{10}$; and $R^2$ is trifluoromethyl;

each $R^{10}$ is independently selected from halo and $S(O)_2R^{b1}$.

In some embodiments of Formula (Ia):

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is 5-10 membered heteroaryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is thiophenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is 5-10 membered heteroaryl, optionally substituted with 1, 2, or 3 substituents independently selected from $R^{10}$; and each $R^{10}$ is independently selected from halo and $S(O)_2R^{b1}$.

In some embodiments of Formula (Ia):

each $R^A$ is independently selected from halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is phenyl, optionally substituted with 1, 2, or 3 substituents independently selected from $R^{10}$;

$R^2$ is thiophenyl, optionally substituted with 1, 2, or 3 substituents independently selected from $R^{10}$; and each $R^{10}$ is independently selected from halo and $S(O)_2R^{b1}$.

In some embodiments, the compound of Formula (I) has Formula (Ib):

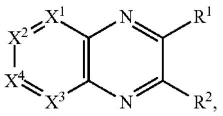

(Ib)

or a pharmaceutically acceptable salt thereof, wherein $X^1$, $X^2$, $X^3$, and $X^4$ are each independently selected from N, CH, and $CR^A$. In some embodiments, not more than two of $X^1$, $X^2$, $X^3$, and $X^4$ is N. In some embodiments, $X^1$ is N. In some embodiments, $X^3$ is N.

In some embodiments, $X^1$ is N. In some embodiments, $X^1$ is CH. In some embodiments, $X^1$ is $CR^A$. In some embodiments, $X^2$ is N. In some embodiments, $X^2$ is CH. In some embodiments, $X^2$ is $CR^A$. In some embodiments, $X^3$ is N. In some embodiments, $X^3$ is CH. In some embodiments, $X^3$ is $CR^A$. In some embodiments, $X^4$ is N. In some embodiments, $X^4$ is CH. In some embodiments, $X^4$ is $CR^A$.

In some embodiments of Formula (Ib):

$R^1$ is selected from $C_{1-6}$ haloalkyl and $S(O)_2R^9$; and $R^2$ is $R^9$.

In some embodiments, the compound of Formula (Ib) has formula:

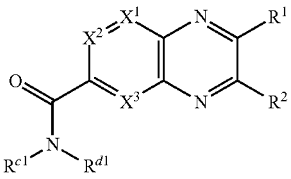

or a pharmaceutically acceptable salt thereof. In some aspects of these embodiments:

$X^1$ is selected from N, CH, and $CR^A$;

$X^2$ is selected from CH and $CR^A$; and $X^3$ is selected from CH and $CR^A$.

In some embodiments, $X^1$ is N. In some embodiments, $X^1$ is $CR^A$.

In some embodiments, the compound of Formula (Ib) has formula:

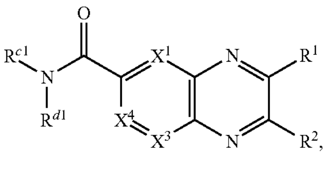

or a pharmaceutically acceptable salt thereof.

In some embodiments:

$X^1$ is selected from N, CH, and $CR^A$;

$X^4$ is selected from CH and $CR^A$; and $X^3$ is selected from N, CH and $CR^A$.

In some embodiments, $X^1$ is N. In some embodiments, $X^1$ is $CR^A$.

In some embodiments, $X^3$ is N. In some embodiments, $X^3$ is $CR^A$. In some embodiments, $X^4$ is $CR^A$.

In some embodiments of Formula (Ib):

$R^1$ is $C_{1-6}$ haloalkyl; and $R^2$ is $C_{6-10}$ aryl, optionally substituted with 1, 2, or 3 independently selected $R^{10}$.

In some embodiments of Formula (Ib):

$R^1$ is $C_{1-6}$ haloalkyl; and $R^2$ is 5-10 membered heteroaryl, optionally substituted with 1, 2, or 3 independently selected $R^{10}$.

In some embodiments, the compound of Formula (Ib) has formula:

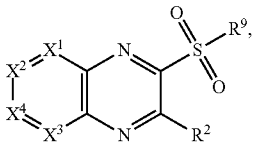

or a pharmaceutically acceptable salt thereof.

In some embodiments, the compound of Formula (Ib) has formula:

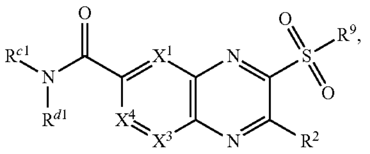

or a pharmaceutically acceptable salt thereof. In some embodiments:

$X^1$ is selected from N, CH, and $CR^A$;

$X^4$ is selected from CH and $CR^A$; and $X^3$ is selected from N, CH and $CR^A$.

In some embodiments, $X^1$ is N. In some embodiments, $X^1$ is $CR^A$.

In some embodiments, $X^3$ is N. In some embodiments, $X^3$ is $CR^A$.

In some embodiments, $R^9$ is $C_{6-10}$ aryl, optionally substituted with 1, 2, or 3 independently selected $R^{10}$.

In some embodiments, $R^{10}$ is selected from halo and $C_{1-6}$ alkyl.

In some embodiments of Formula (Ib):

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$;

or any $R^{c1}$ and $R^{d1}$ together with the N atom to which they are attached form a 4-7 membered heterocycloalkyl, which is optionally substituted with 1 or 2 substituents independently selected from $R^g$;

each $R^9$ is independently selected from $C_{6-10}$ aryl and 5-10 membered heteroaryl, each of which is optionally substituted with 1, 2, or 3 independently selected $R^{10}$; and each $R^{10}$ is independently selected from halo and $C_{1-6}$ alkyl.

In some embodiments, the compound of Formula (I) has Formula (Ic):

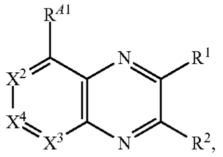

(Ic)

or a pharmaceutically acceptable salt thereof, wherein:

$X^2$, $X^3$, and $X^4$ are each independently selected from N, CH, and $CR^A$; and $R^{A1}$ is selected from $C(O)NR^{c1}R^{d1}$ and $C(O)OR^{a1}$.

In some embodiments of Formula (Ic):

$X^3$ is selected from N, CH, and $CR^A$;

$X^2$ is selected from CH and $CR^A$; and $X^4$ is selected from CH and $CR^A$.

In some embodiments, $X^3$ is N. In some embodiments, $X^3$ is $CR^A$.

In some embodiments of Formula (Ic), each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^A$ is selected from halo, $C_{1-6}$ alkyl, and $C_{1-6}$ alkoxy.

In some embodiments, $R^{A1}$ is $C(O)OR^{a1}$.

In some embodiments, $R^{A1}$ is $C(O)NR^{c1}R^{d1}$.

In some embodiments of Formula (Ic), $R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments of Formula (Ic), $R^{c1}$ and $R^{d1}$ together with the N atom to which they are attached form a 4-7 membered heterocycloalkyl, which is optionally substituted with 1 or 2 substituents independently selected from $R^g$.

In some embodiments of Formula (Ic), $R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

In some embodiments, each $R^{10}$ is independently selected from halo and $C_{1-6}$ alkyl.

In some embodiments of Formula (Ic):

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$; or $R^{c1}$ and $R^{d1}$ together with the N atom to which they are attached form a 4-7 membered heterocycloalkyl, which is optionally substituted with 1 or 2 substituents independently selected from $R^g$;

$R^1$ and $R^2$ are each independently an $C_{6-10}$ aryl, optionally substituted with 1, 2, or 3 independently selected $R^{10}$; and each $R^{10}$ is independently selected from halo and $C_{1-6}$ alkyl.

In some embodiments, the compound of Formula (I) has Formula (Id):

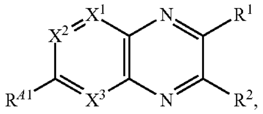

(Id)

or a pharmaceutically acceptable salt thereof, wherein:

$X^1$, $X^2$, and $X^3$ are each independently selected from N, CH, and $CR^A$; and $R^{A1}$ is selected from $NR^{c1}R^{d1}$, $NR^{c1}C(O)R^{b1}$, $NR^{c1}C(O)OR^{a1}$, and $NR^{c1}C(O)NR^{c1}R^{d1}$.

In some embodiments of Formula (Id):

$X^1$ is selected from N, CH, and $CR^A$;

$X^3$ is selected from N, CH, and $CR^A$; and $X^2$ is selected from CH and $CR^A$.

In some embodiments, $X^1$ is N. In some embodiments, $X^1$ is $CR^A$.

In some embodiments, $X^3$ is N. In some embodiments, $X^3$ is $CR^A$.

In some embodiments of Formula (Id), each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^A$ is selected from halo, $C_{1-6}$ alkyl, and $C_{1-6}$ alkoxy.

In some embodiments, $R^{A1}$ is $NR^{c1}C(O)OR^{a1}$. In some embodiments, $R^{a1}$ is selected from $C_{1-6}$ alkyl, $C_{1-4}$ haloalkyl, $C_{2-6}$ alkenyl, and $C_{2-6}$ alkynyl, each of which is optionally substituted with 1 or 2 $R^g$.

In some embodiments, $R^{A1}$ is $NR^{c1}C(O)R^{b1}$. In some embodiments, $R^{b1}$ is selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1 or 2 $R^g$.

In some embodiments, $R^{A1}$ is selected from $NR^{c1}R^{d1}$ and $NR^{c1}C(O)NR^{c1}R^{d1}$. In some embodiments, $R^{A1}$ is $NR^{c1}R^{d1}$ In some embodiments, $R^{A1}$ is $NR^{c1}C(O)NR^{c1}R^{d1}$.

In some embodiments, each $R^{c1}$ and $R^{d1}$ is independently selected from H, $C_{1-6}$ alkyl, $C_{2-6}$ alkynyl, $C_{3-10}$ cycloalkyl, 4-10 membered heterocycloalkyl, 5-10 membered heteroaryl, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1 or 2 independently selected $R^g$.

In some embodiments, $R^{c1}$ and $R^{d1}$ together with the N atom to which they are attached form a 4-7 membered heterocycloalkyl, which is optionally substituted with 1 or 2 substituents independently selected from $R^g$.

In some embodiments of Formula (Id), $R^1$ and $R^2$ are each independently an $C_{6-10}$ aryl, optionally substituted with 1, 2, or 3 independently selected $R^{10}$.

In some embodiments, each $R^{10}$ is independently selected from halo and $C_{1-6}$ alkyl.

In some embodiments of Formula (Id):

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^{a1}$ is selected from $C_{1-6}$ alkyl, $C_{1-4}$ haloalkyl, $C_{2-6}$ alkenyl, and $C_{2-6}$ alkynyl, each of which is optionally substituted with 1 or 2 $R^g$;

$R^{b1}$ is selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1 or 2 $R^g$;

each $R^{c1}$ and $R^{d1}$ is independently selected from H, $C_{1-6}$ alkyl, $C_{2-6}$ alkynyl, $C_{3-10}$ cycloalkyl, 4-10 membered heterocycloalkyl, 5-10 membered heteroaryl, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1 or 2 independently selected $R^g$; or $R^{c1}$ and $R^{d1}$ together with the N atom to which they are attached form a 4-7 membered heterocycloalkyl, which is optionally substituted with 1 or 2 substituents independently selected from $R^g$;

$R^1$ and $R^2$ are each independently an $C_{6-10}$ aryl, optionally substituted with 1, 2, or 3 independently selected $R^{10}$; and each $R^{10}$ is independently selected from halo and $C_{1-6}$ alkyl.

In some embodiments, the compound of Formula (I) has Formula (Ie):

(Ie)

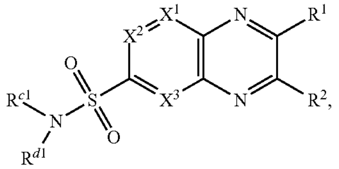

or a pharmaceutically acceptable salt thereof, wherein $X^1$, $X^2$, and $X^3$ are each independently selected from N, CH, and $CR^A$.

In some embodiments of Formula (Ie):

$X^1$ is selected from N, CH, and $CR^A$;

$X^3$ is selected from N, CH, and $CR^A$; and $X^2$ is selected from CH and $CR^A$.

In some embodiments of Formula (Ie), each $R^A$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments of Formula (Ie), $R^{c1}$ and $R^{d1}$ are each independently selected from $C_{1-6}$ alkyl, $C_{3-10}$ cycloalkyl, (4-10 membered heterocycloalkyl)-$C_{1-4}$ alkylene, and (5-10 membered heteroaryl)-$C_{1-4}$ alkylene, each of which is optionally substituted with 1 or 2 $R^g$.

In some embodiments, $R^1$ and $R^2$ are each independently an $C_{6-10}$ aryl, optionally substituted with 1 or 2 independently selected $R^{10}$.

In some embodiments, each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments of Formula (Ie):

each $R^A$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl) amino;

$R^{c1}$ and $R^{d1}$ are each independently selected from $C_{1-6}$ alkyl, $C_{3-10}$ cycloalkyl, (4-10 membered heterocycloalkyl)-$C_{1-4}$ alkylene, and (5-10 membered heteroaryl)-$C_{1-4}$ alkylene, each of which is optionally substituted with 1 or 2 $R^g$;

$R^1$ and $R^2$ are each independently an $C_{6-10}$ aryl, optionally substituted with 1 or 2 independently selected $R^{10}$; and each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl) amino.

In some embodiments of Formula (I), ring A is $C_{3-8}$ cycloalkyl (e.g., cyclobutyl, cyclopentyl, cyclohexyl, or cycloheptyl).

In some embodiments, the compound of Formula (I) has Formula (If):

(If)

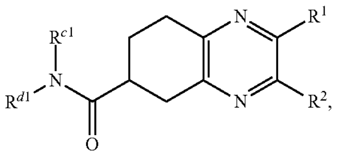

or a pharmaceutically acceptable salt thereof.

In some embodiments, the compound of Formula (I) has Formula (Ig):

(Ig)

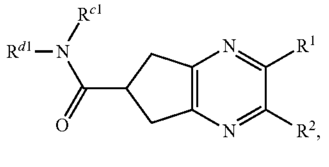

or a pharmaceutically acceptable salt thereof.

In some embodiments of Formula (If) or Formula (Ig):

$R^{c1}$ and $R^{d1}$ together with the N atom to which they are attached form a 4-7 membered heterocycloalkyl, which is optionally substituted with 1, 2, or 3 substituents independently selected from $R^g$;

$R^1$ and $R^2$ are each independently an $C_{6-10}$ aryl, optionally substituted with 1, 2, or 3 substituents independently selected from $R^{10}$; and each $R^{10}$ is independently a halo.

In some embodiments, when the compound of Formula (I) has formula (i), then $R^{c1}$ of $C(O)NR^{c1}R^{d1}$ of $R^{A1}$ is not imidazolyl-$C_{1-4}$ alkylene, pyrazolyl-$C_{1-4}$ alkylene, tetrazolyl-$C_{1-4}$ alkylene, indolyl-$C_{1-4}$ alkylene, pyridinyl-$C_{1-4}$ alkylene, pyridazinyl-$C_{1-4}$ alkylene, thiazolyl-$C_{1-4}$ alkylene, pyrimidinyl-$C_{1-4}$ alkylene, or triazolyl-$C_{1-4}$ alkylene.

In some embodiments, the compound of Formula (I) is not any of the compounds disclosed in U.S. patent publication No. 2017/0174704, which is incorporated by reference in its entirety.

In some embodiments, the compound of Formula (I) is selected from any one of the compounds listed in Table 2a, Table 3, Table 4, Table 5, Table 6, Table 7, Table 8, Table 9, Table 10, Table 11, Table 12, Table 13, Table 14, and Table 15a, or a pharmaceutically acceptable salt thereof.

In some embodiments, the compound of Formula (I) is selected from any one of the compounds listed in Table 2a, or a pharmaceutically acceptable salt thereof.

In some embodiments, the compound of Formula (I) is selected from any one of the compounds listed in Table 3, or a pharmaceutically acceptable salt thereof.

In some embodiments, the compound of Formula (I) is selected from any one of the compounds listed in Table 4, or a pharmaceutically acceptable salt thereof.

In some embodiments, the compound of Formula (I) is selected from any one of the compounds listed in Table 5, or a pharmaceutically acceptable salt thereof.

In some embodiments, the compound of Formula (I) is selected from any one of the compounds listed in Table 6, or a pharmaceutically acceptable salt thereof.

In some embodiments, the compound of Formula (I) is selected from any one of the compounds listed in Table 7, or a pharmaceutically acceptable salt thereof.

In some embodiments, the compound of Formula (I) is selected from any one of the compounds listed in Table 8, or a pharmaceutically acceptable salt thereof.

In some embodiments, the compound of Formula (I) is selected from any one of the compounds listed in Table 9, or a pharmaceutically acceptable salt thereof.

In some embodiments, the compound of Formula (I) is selected from any one of the compounds listed in Table 10, or a pharmaceutically acceptable salt thereof.

In some embodiments, the compound of Formula (I) is selected from any one of the compounds listed in Table 11, or a pharmaceutically acceptable salt thereof.

In some embodiments, the compound of Formula (I) is selected from any one of the compounds listed in Table 12, or a pharmaceutically acceptable salt thereof.

In some embodiments, the compound of Formula (I) is selected from any one of the compounds listed in Table 13, or a pharmaceutically acceptable salt thereof.

In some embodiments, the compound of Formula (I) is selected from any one of the compounds listed in Table 14, or a pharmaceutically acceptable salt thereof.

In some embodiments, the compound of Formula (I) is selected from any one of the compounds listed in Table 15a, or a pharmaceutically acceptable salt thereof.

In some embodiments, the present disclosure provides a compound selected from any one of the compounds listed in Table 8, or a pharmaceutically acceptable salt thereof.

In some embodiments, the present disclosure provides a compound selected from any one of the compounds listed in Table 15b, or a pharmaceutically acceptable salt thereof.

Formula (II)

In some embodiments, the present disclosure provides a compound of Formula (II):

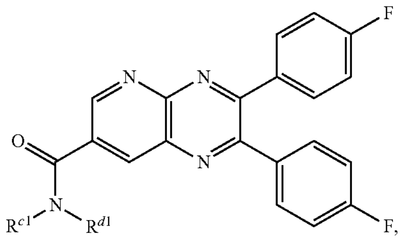

(II)

or a pharmaceutically acceptable salt thereof, wherein $R^{c1}$ and $R^{d1}$ are as described herein.

In some embodiments of Formula (II):

$R^{c1}$ and $R^{d1}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, the compound of Formula (II) is not a compound of formula:

(BC19408)

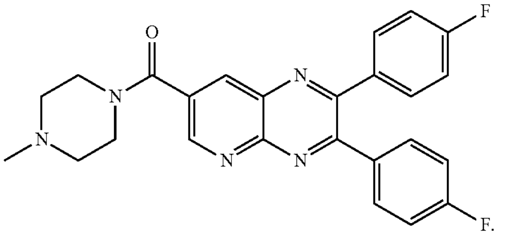

In some embodiments of Formula (II), each $R^{c1}$ and $R^{d1}$ is independently selected from H, $C_{1-6}$ alkyl, alkenyl, $C_{2-6}$ alkynyl, (5-10 membered heteroaryl)-$C_{1-4}$ alkylene, and (4-10 membered heterocycloalkyl)-$C_{1-4}$ alkylene, each of which is optionally substituted with 1 or 2 $R^g$.

In some embodiments of Formula (II), $R^{c1}$ and $R^{d1}$ together with the N atom to which they are attached form a 4-7 membered heterocycloalkyl, which is optionally substituted with 1, 2, or 3 substituents independently selected from $R^g$.

In some embodiments, each $R^9$ is independently selected from $C_{1-6}$ alkoxy, OH, amino, $C_{1-6}$ alkylamino, and di($C_{1-6}$ alkyl)amino.

In some embodiments, the compound of Formula (II) is selected from any one of the compounds listed in Table 11, or a pharmaceutically acceptable salt thereof.

Formula (III)

In some embodiments, the present disclosure provides a compound of Formula (III):

(III)

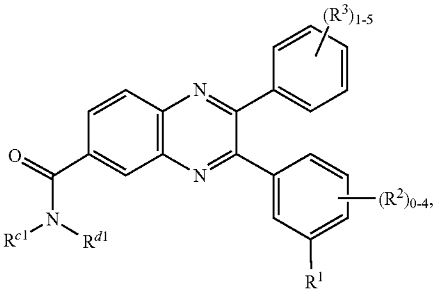

or a pharmaceutically acceptable salt thereof, wherein $R^{c1}$, $R^{d1}$, $R^1$, $R^2$, and $R^3$ are as described herein.

In some embodiments of Formula (III):

$R^1$ is selected from $C_{1-6}$ alkyl, $NR^{c1}R^{d1}$, $NR^{c1}C(O)R^{b1}$, and $NR^{c1}S(O)_2R^{b1}$, wherein said $C_{1-6}$ alkyl is substituted with a substituent selected from $OR^{a1}$, $NR^{c1}R^{d1}$, $NR^{c1}C(O)R^{b1}$, and $NR^{c1}S(O)_2R^{b1}$;

$R^2$ and $R^3$ are each independently selected from halo, CN, $NO_2$, $C_{1-6}$ alkyl, $C_{1-6}$ haloalkyl, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with a substituent selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_6$-aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments of Formula (III), when $R^1$ is $NR^{c1}R^{d1}$ then at least one $R^3$ is selected from halo, CN, $NO_2$, $C_{1-6}$ alkyl, $C_{1-6}$ haloalkyl, $C(O)NR^{c1}R^{d1}$, $C(O)OR^{a1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with a substituent selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^1$ is $C_{1-6}$ alkyl, substituted with a substituent selected from $OR^{a1}$, $NR^{c1}R^{d1}$, $NR^{c1}C(O)R^{b1}$, and $NR^{c1}S(O)_2R^{b1}$.

In some embodiments, $R^1$ is $NR^{c1}R^{d1}$.

In some embodiments, $R^1$ is $NR^{c1}C(O)R^{b1}$.

In some embodiments, $R^1$ is $NR^{c1}S(O)_2R^{b1}$.

In some embodiments, $R^3$ is selected from halo, $C_{1-6}$ alkyl, $NR^{c1}R^{d1}$, $NR^{c1}C(O)R^{b1}$, and $NR^{c1}S(O)_2R^{b1}$, wherein said $C_{1-6}$ alkyl is substituted with a substituent selected from $OR^{a1}$, $NR^{c1}R^{d1}$, $NR^{c1}C(O)R^{b1}$, and $NR^{c1}S(O)_2R^{b1}$.

In some embodiments, $R^{a1}$, $R^{b1}$, $R^{c1}$, and $R^{d1}$ is each independently selected from H, $C_{1-6}$ alkyl, and $C_{2-6}$ alkynyl, each of which is optionally substituted with 1 or 2 $R^g$.

In some embodiments, $R^{c1}$ and $R^{d1}$ together with the N atom to which they are attached form a 4-7 membered heterocycloalkyl, which is optionally substituted with 1 or 2 substituents independently selected from $R^g$.

In some embodiments, each $R^9$ is independently selected from $C_{1-6}$ alkyl, OH, $C_{1-6}$ alkoxy, amino, $C_{1-6}$ alkylamino, and di($C_{1-6}$ alkyl)amino.

In some embodiments, the compound of Formula (III) is selected from any one of the compounds listed in Table 12, or a pharmaceutically acceptable salt thereof.

Formula (IV)

In some embodiments, the present disclosure provides a compound of Formula (IV)

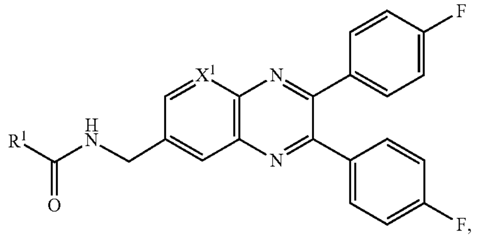

or a pharmaceutically acceptable salt thereof, wherein $R^1$ is as described herein.

In some embodiments:

$X^1$ is selected from N and CH;

$R^1$ is selected from $R^{b1}$ and $NR^{c1}R^{d1}$;

each $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_6$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, $X^1$ is N.

In some embodiments, $X^1$ is CH.

In some embodiments, $R^1$ is $R^{b1}$.

In some embodiments, $R^1$ is and $NR^{c1}R^{d1}$.

In some embodiments, each $R^{b1}$, $R^{c1}$, and $R^{d1}$ is independently selected from 5-10 membered heteroaryl, 4-10 membered heterocycloalkyl, (5-10 membered heteroaryl)-$C_{1-4}$ alkylene, and (4-10 membered heterocycloalkyl)-$C_{1-4}$ alkylene, each of which is optionally substituted with 1 or 2 $R^g$.

In some embodiments, each $R^g$ is independently selected from $C_{1-6}$ alkyl, OH, $C_{1-6}$ alkoxy, amino, $C_{1-6}$ alkylamino, and di($C_{1-6}$ alkyl)amino.

In some embodiments, the compound of Formula (IV) is selected from any one of the compounds listed in Table 13, or a pharmaceutically acceptable salt thereof.

Formula (V)

In some embodiments, the present disclosure provides a compound of Formula (V)

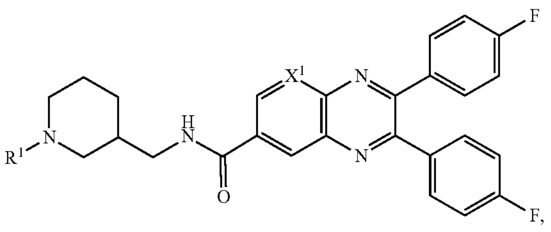

or a pharmaceutically acceptable salt thereof, wherein $X^1$ and $R^1$ is as described herein.

In some embodiments of Formula (V):

$X^1$ is selected from N and CH;

$R^1$ is selected from H, $S(O)_2R^{b1}$, and $C(O)R^{b1}$;

$R^{b1}$ is selected from $C_{1-6}$ alkyl and $C_{2-6}$ alkynyl, each of which is optionally substituted with a substituent selected from OH, halo, $C_{1-6}$ alkoxy, $C_{1-6}$ haloalkoxy, amino, $C_{1-6}$ alkylamino, and di($C_{1-6}$ alkyl)amino.

In some embodiments, $X^1$ is N.

In some embodiments, $X^1$ is CH.

In some embodiments, $R^{b1}$ is selected from $C_{1-6}$ alkyl and $C_{2-6}$ alkynyl, each of which is optionally substituted with a substituent selected from OH, halo, $C_{1-6}$ alkoxy, $C_{1-6}$ haloalkoxy, amino, $C_{1-6}$ alkylamino, and di($C_{1-6}$ alkyl) amino.

In some embodiments, $R^{b1}$ is $C_{1-6}$ alkyl, optionally substituted with a substituent selected from OH, halo, $C_{1-6}$ alkoxy, $C_{1-6}$ haloalkoxy, amino, $C_{1-6}$ alkylamino, and di($C_{1-6}$ alkyl)amino.

In some embodiments, $R^{b1}$ is $C_{2-6}$ alkynyl.

In some embodiments, the compound of Formula (V) is selected from any one of the compounds listed in Table 14, or a pharmaceutically acceptable salt thereof.

Formula (VI)

In some embodiments, the present disclosure provides a compound of Formula (VI):

(VI)

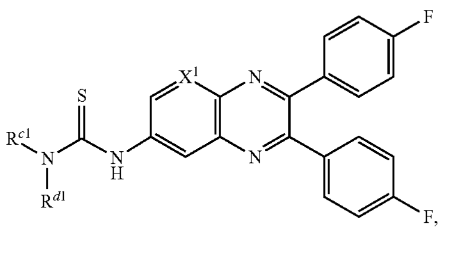

or a pharmaceutically acceptable salt thereof, wherein $X^1$, $R^{c1}$, and $R^{d1}$ are as described herein.

In some embodiments:

$X^1$ is selected from N and CH;

$R^{c1}$ and $R^{d1}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, $X^1$ is N.

In some embodiments, $X^1$ is CH.

In some embodiments, $R^{d1}$ is H, and $R^{c1}$ is selected from 5-10 membered heteroaryl, 4-10 membered heterocycloalkyl, (5-10 membered heteroaryl)-$C_{1-4}$ alkylene, and (4-10 membered heterocycloalkyl)-$C_{1-4}$ alkylene, each of which is optionally substituted with 1 or 2 $R^g$; or $R^{c1}$ and $R^{d1}$ together with the N atom to which they are attached form a 4-7 membered heterocycloalkyl, which is optionally substituted with $R^g$.

In some embodiments, $R^{d1}$ is H, and $R^{c1}$ is (5-10 membered heteroaryl)-$C_{1-4}$ alkylene, which is optionally substituted with 1 or 2 $R^g$.

In some embodiments, each $R^g$ is independently selected from $C_{1-6}$ alkyl, OH, $C_{1-6}$ alkoxy, amino, $C_{1-6}$ alkylamino, and di($C_{1-6}$ alkyl)amino.

In some embodiments, the compound of Formula (VI) is selected from any one of the compounds listed in Table 15a, or a pharmaceutically acceptable salt thereof.

In some embodiments, the present disclosure provides a compound listed in able 15b, or a pharmaceutically acceptable salt thereof.

In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compounds disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH-(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, any one of the compounds disclosed herein, or a pharmaceutically acceptable salt thereof, is substantially isolated.

Methods of Making Therapeutic Compounds

Compounds as set forth in any one of the Formulae disclosed herein, including salts thereof, can be prepared using organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates, and products can be identified by reference to the literature, including reference sources such as: Advances in Heterocyclic Chemistry, Vols. 1-107 (Elsevier, 1963-2012); *Journal of Heterocyclic Chemistry* Vols. 1-49 (J. Heterocyclic Chemistry, 1964-2012); Carreira et al., (Ed.) *Science of Synthesis, Vols.* 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, 2nd Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure,* 6th Ed. (Wiley, 2007); Trost et al. (Ed.) *Comprehensive Organic Synthesis* (Pergamon Press, 1991).

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* 4th Ed., Wiley & Sons, Inc., New York (2006).

Pharmaceutical Compositions and Formulations

This document also provides pharmaceutical compositions comprising an effective amount of a compound disclosed herein, or a pharmaceutically acceptable salt thereof; and a pharmaceutically acceptable carrier. The pharmaceutical composition also can comprise any one of the additional therapeutic agents and/or therapeutic molecules described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds disclosed herein, or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., any one of the compounds disclosed herein, or a pharmaceutically acceptable salt thereof) with a suitable non-irritating excipient that is solid at room temperature but liquid at the rectal temperature and therefore will melt in the rectum to release the active component(s). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., J. Pharm. Pharmacol., 56:3-17 (2004); and Ilium, L., Eur. J. Pharm. Sci., 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound set forth in any one of Formulae disclosed herein, or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., any one of the compounds disclosed herein, or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos. 6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., any one of the compounds disclosed herein, or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein, or a pharmaceutically acceptable salt thereof, can include that compound in an effective amount (e.g., a therapeutically effective amount).

Effective doses can vary, depending on the diseases being treated, the severity of the disease, the route of administration, the sex, age and general health condition of the subject, excipient usage, the possibility of co-usage with other therapeutic treatments such as use of other agents, and the judgment of the treating physician.

In some embodiments, an effective amount of a compound as disclosed herein, or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated as described herein.

In some cases, an effective amount of a compound as disclosed herein, or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound as disclosed herein, or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to inhibit NF-kβ within cells within a mammal (e.g., a human). In some cases, this document provides pharmaceutical kits useful, for example, to treat diseases, disorders, and conditions referred to herein. Such pharmaceutical kits can include one or more containers containing a pharmaceutical composition that includes a therapeutically effective amount of a compound provided herein, or a pharmaceutically acceptable salt thereof. In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein.

Combination Therapies

In some cases, one or more compounds provided herein, or a pharmaceutically acceptable salt thereof, can be combined with one or more therapeutic molecules. Examples of therapeutic molecules that can be used in combination with one or more compounds provided herein, or a pharmaceutically acceptable salt thereof, include, without limitation, chemotherapeutic agents (e.g., vincristine or cisplatin), anti-inflammatory agents (e.g., steroids or hydroxychloroquine), and biological agents directed against circulating TNF-α, IL-6, or other inflammatory mediators.

One or more compounds provided herein, or a pharmaceutically acceptable salt thereof, and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in this document, substituents of compounds provided herein are disclosed in groups or in ranges. It is specifically intended that these groups and ranges include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in this document various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features described herein, which are, for clarity, described in the context of separate embodiments, can also be provided in combination in a single embodiment. Conversely, various features described herein which are, for brevity, described in the context of a single embodiment, also can be provided separately or in any suitable subcombination.

The term "aromatic" refers to a carbocycle or heterocycle having one or more polyunsaturated rings having aromatic character (i.e., having (4n+2) delocalized 71 (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "Cn-m" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, without limitation, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, without limitation, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl-linking group having n to m carbons. Examples of alkylene groups include, without limitation, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, without limitation, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula $—NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, without limitation, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula $—N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, without limitation, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, without limitation, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula $—NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula $—S(O)_2NH_2$.

As used herein, the term "$C_{n-m}$ alkylaminosulfonyl" refers to a group of formula $—S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula $—S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula $—NHS(O)_2NH_2$.

As used herein, the term "$C_{n-m}$ alkylaminosulfonylamino" refers to a group of formula $—NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —$C(O)NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)-group, which may also be written as C(O).

As used herein, the term "carboxy" refers to a —C(O)OH group. In some embodiments, the "carboxy" group also refers to a bioisostere replacement group selected from the group consisting of:

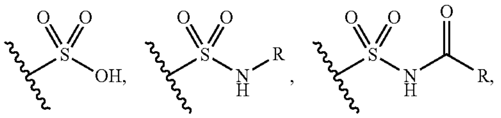

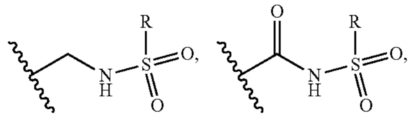

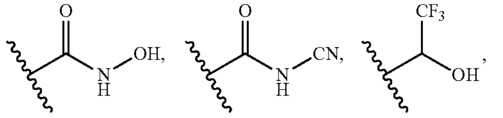

-continued

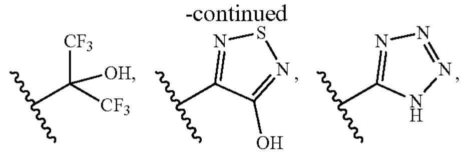

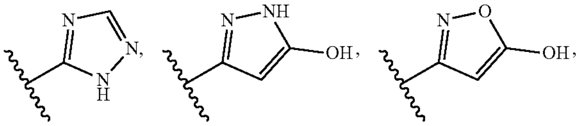

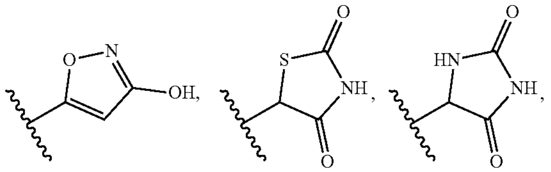

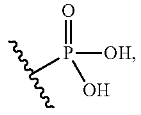

and the like, where R refers to a hydrogen, ($C_1$-$C_8$) alkyl, or $C_6$ aryl.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which can be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups can have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3, or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include, without limitation, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from nitrogen, sulfur, and oxygen. In some embodiments, the heteroaryl is a 5-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl. Ring-forming carbon atoms of a heteroaryl group can be optionally substituted by 1 or 2 independently selected oxo or sulfide groups (e.g., C(O) or C(S)).

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, or 10-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings (aryl rings or heteroaryl rings) fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring can be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C═O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Any appropriate method can be used to prepare optically active forms from, for example, optically inactive starting materials. For example, techniques such as resolution of racemic mixtures or stereoselective synthesis can be used to prepare optically active forms of a compound provided herein. Many geometric isomers of olefins, C═N double bonds, N═N double bonds, and the like also can be present in a compound described herein, and all such stable isomers are contemplated herein. Cis and trans geometric isomers of the compounds provided herein are described and can be isolated as a mixture of isomers or as separated isomeric forms. In some embodiments, a compound provided herein has the (R)-configuration. In some embodiments, a compound provided herein has the (S)-configuration.

Compounds provided herein also include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include, without limitation, ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution. For example, in aqueous solution, pyrazoles can exhibit the following isomeric forms, which are referred to as tautomers of each other:

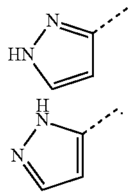

As readily understood by one skilled in the art, a wide variety of functional groups and other structures can exhibit tautomerism, and all tautomers of compounds as described herein are within the scope provided herein.

As used herein, the term “cell” is meant to refer to a cell that is in vitro, ex vivo, or in vivo. In some embodiments, an ex vivo cell can be part of a tissue sample excised from an organism such as a mammal (e.g., a human). In some embodiments, an in vitro cell can be a cell in cell culture. In some embodiments, an in vivo cell is a cell living in an organism such as a mammal (e.g., a human).

As used herein, the term “contacting” refers to the bringing together of indicated moieties or items in an in vitro system, an ex vivo system, or an in vivo system. For example, “contacting” a cell with a compound provided herein includes the act of administering that compound to a mammal (e.g., a human) containing that cell as well as, for example, introducing that compound into a cell culture containing that cell.

As used herein, the term “mammal” includes, without limitation, mice, rats, other rodents, rabbits, dogs, cats, swine, cattle, sheep, horses, elephants, deer, non-human primates (e.g., monkeys and apes), house pets, and humans.

As used herein, the phrase “effective amount” or “therapeutically effective amount” refers to the amount of active compound or pharmaceutical agent that elicits the biological or medicinal response in a tissue, system, mammal, or human that is being sought by a researcher, veterinarian, medical doctor, or other clinician.

As used herein, the term “treating” or “treatment” refers to (a) inhibiting a disease, disorder, or condition, for example, inhibiting a disease, disorder, or condition in a mammal (e.g., human) that is experiencing or displaying the pathology or symptomatology of the disease, disorder, or condition (e.g., arresting further development of the pathology and/or symptomatology), or (b) ameliorating the disease, disorder, or condition, for example, ameliorating a disease, disorder, or condition in a mammal (e.g., a human) that is experiencing or displaying the pathology or symptomatology of the disease, disorder, or condition (e.g., reversing the pathology and/or symptomatology).

As used herein, the term “preventing” or “prevention” of a disease, disorder, or condition refers to decreasing the risk of occurrence of the disease, disorder, or condition in a mammal or group of mammals (e.g., a mammal or group of mammals predisposed to or susceptible to the disease, disorder, or condition). In some embodiments, preventing a disease, disorder, or condition refers to decreasing the possibility of acquiring the disease, disorder, or condition and/or its associated symptoms. In some embodiments, preventing a disease, disorder, or condition refers to completely or almost completely stopping the disease, disorder, or condition from occurring.

EXAMPLES

Assay for In Vitro NAMPT Activity Via NMN Assessment

The following were added to a well: 20 μL 2× test compound in Basic Buffer (0.02% BSA, 2 mM DTT, 12 mM $MgCl_2$, 50 mM Tris pH7.5); 10 μL 8 μg/mL NAMPT, and 200 μM PRPP working solution (or PRPP working solution to background wells). 10 μL 100 μM NAM working solution was added to start the reaction. The plate was sealed and incubated for 45 minutes at 37° C. After incubation, 10 μL 20% acetophenone in DMSO, 10 μL 2N KOH, and 20 μL 88% formic acid were added. The plate was sealed and incubated for 30 minutes at 37° C. After incubation, fluorescence at Ex/Em 387/441 was read.

Assay for Total NADH and $NAD^+$ Measurements in Cells 2,000 cells/well and, at the same time, test compounds dissolved in media at the desired concentration were added to each well. The treated cells were incubated overnight in $C_{02}$ incubator. The cells were washed 6 times with PBS with 1 mM $CaCl_2$) and 1 mM $MgCl_2$. In the last wash, 10 μL of PBS with 1 mM $CaCl_2$) and 1 mM $MgCl_2$ per well were left in each well. Immediately thereafter, 10 μL 0.4% dodecyltrimethylammonium bromide (DTAB) in phosphate buffer pH 8.0 as added, and the plates were shaked at 1000 rpm for 5 minutes. 60 μL reaction mix was added, and fluorescence at Ex/Em 530/585 was immediately monitored. A linear increase should be achieved with 8 cycles every 92 seconds, 10 number of flashes/well/cycle. The reaction mix was prepared per the following table, respecting the amount and order in which each component was added:

| Component | [Stock] | [final] | Mix for 1 plate |
|---|---|---|---|
| Sodium phosphate buffer (pH 8.0) | 100 mM | | 24473.3 μL |
| Ethanol | 95% | 0.76% | 266.7 μL |
| Riboflavin 5'-monophosphate sodium salt hydrate (FMN) | 10 mM | 4 μM | 13.33 μL |
| Alcohol dehydrogenase (ADH) | 3,400 U/mL | 5.44 U/mL | 53.3 μL |
| Diaphorase | 100 U/mL | 0.18 U/mL | 60 μL |
| Resazurin | 2 mM | 8 μM | 133.3 μL |
| | | Total: | 25 mL |

All assays were performed in A431 cells. Referring to the tables below, activity: “+”≥25 μM, “++”≥1 μM and <25 μM, and “+++”<1 μM.

In each table header, A: NAMPT enzyme inhibitory activity, $IC_{50}$ (μM); B: Cellular NAD inhibitory activity, $IC_{50}$ (μM); and C: change in NAD levels in response to test compound, shown as % of NAD activity in the absence of test compound. In particular, column “C” shows the decrease in NAD levels in response to the indicated test compound, as the percent of NAD level compared to that in the absence of the test compound. A percentage of 100 percent would indicate no increase or decrease in NAD levels as compared to that measured for untreated control cells, while a percentage of 50 percent would indicate a decrease in NAD levels of 50 percent as compared to that measured for untreated control cells.

TABLE 1
| BC No. | Compound | A | B |
|---|---|---|---|
| BC18405 | 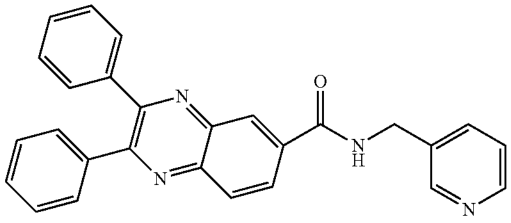 [SMILES: O=C(NCc1cccnc1)c1ccc2nc(-c3ccccc3)c(-c3ccccc3)nc2c1] | +++ | +++ |
TABLE 2a
| BC No. | Structure | C |
|---|---|---|
| BC19192 | 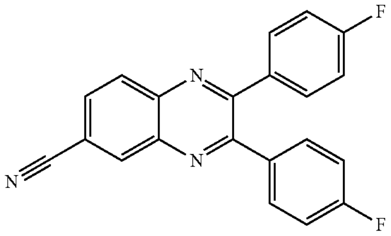 [SMILES: N#Cc1ccc2nc(-c3ccc(F)cc3)c(-c3ccc(F)cc3)nc2c1] | 76 |
| BC19194 | 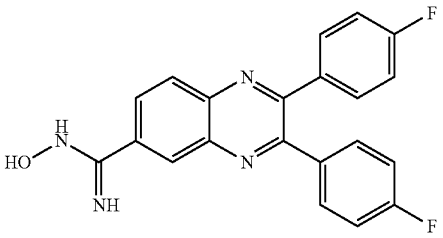 [SMILES: N=C(NO)c1ccc2nc(-c3ccc(F)cc3)c(-c3ccc(F)cc3)nc2c1] | 45 |
| BC19578 | 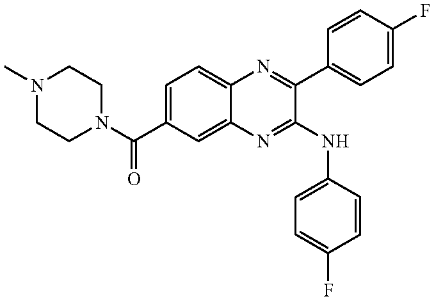 [SMILES: CN1CCN(C(=O)c2ccc3nc(-c4ccc(F)cc4)c(Nc4ccc(F)cc4)nc3c2)CC1] | 89 |
TABLE 2a-continued
| BC No. | Structure | C |
|---|---|---|
| BC19668 | 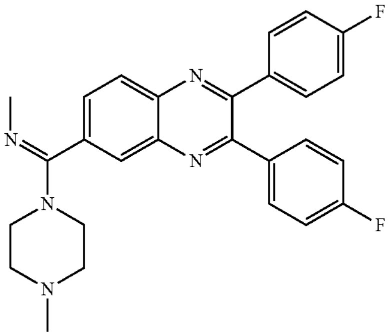 [SMILES: C/N=C(\c1ccc2nc(-c3ccc(F)cc3)c(-c3ccc(F)cc3)nc2c1)N1CCN(C)CC1] | 31 |
| BC19577 | 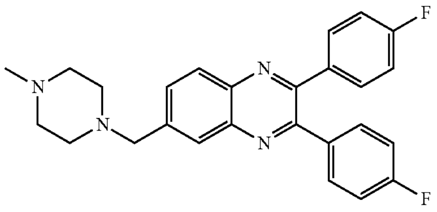 [SMILES: CN1CCN(Cc2ccc3nc(-c4ccc(F)cc4)c(-c4ccc(F)cc4)nc3c2)CC1] | 41 |
TABLE 2b
| BC No. | Structure | C |
|---|---|---|
| BC19154 | 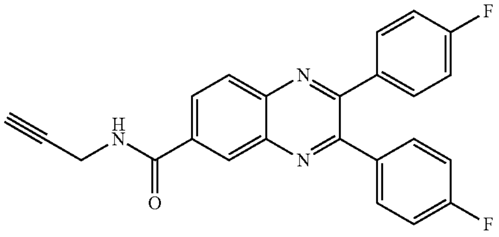 [SMILES: C#CCNC(=O)c1ccc2nc(-c3ccc(F)cc3)c(-c3ccc(F)cc3)nc2c1] | 73 |

TABLE 2b-continued
| BC No. | Structure | C |
|---|---|---|
| BC19237 | 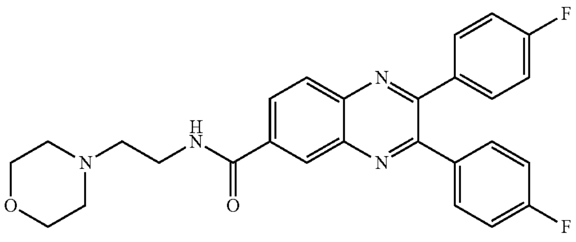 [SMILES: O=C(NCCN1CCOCC1)c1ccc2nc(-c3ccc(F)cc3)c(-c3ccc(F)cc3)nc2c1] | 24 |
| BC19317 | 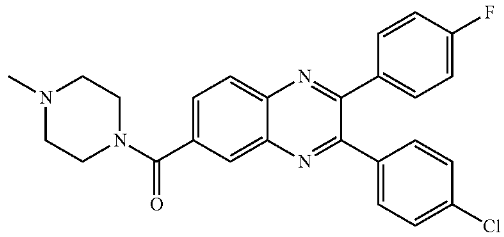 [SMILES: CN1CCN(C(=O)c2ccc3nc(-c4ccc(F)cc4)c(-c4ccc(Cl)cc4)nc3c2)CC1] | 42 |
| BC19318 | 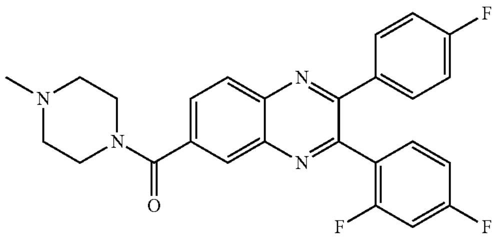 [SMILES: CN1CCN(C(=O)c2ccc3nc(-c4ccc(F)cc4)c(-c4ccc(F)cc4F)nc3c2)CC1] | 67 |
| BC19319 | 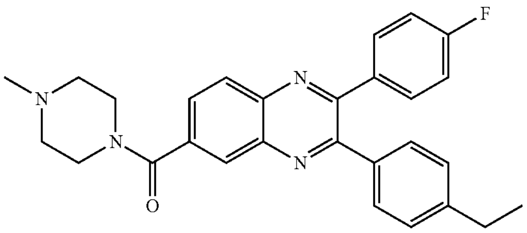 [SMILES: CCc1ccc(-c2nc3cc(C(=O)N4CCN(C)CC4)ccc3nc2-c2ccc(F)cc2)cc1] | 95 |
| BC19398 | 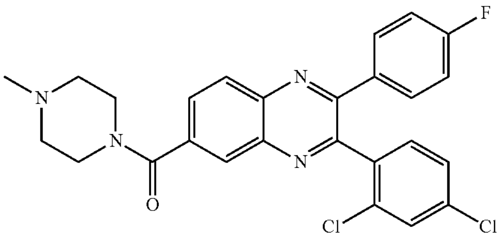 [SMILES: CN1CCN(C(=O)c2ccc3nc(-c4ccc(F)cc4)c(-c4ccc(Cl)cc4Cl)nc3c2)CC1] | 94 |
| BC19399 | 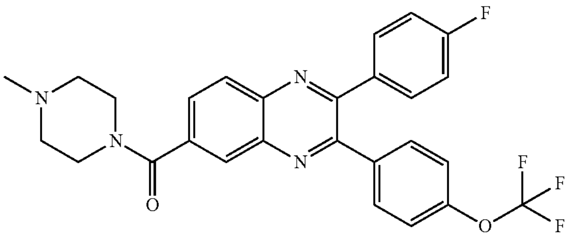 [SMILES: CN1CCN(C(=O)c2ccc3nc(-c4ccc(F)cc4)c(-c4ccc(OC(F)(F)F)cc4)nc3c2)CC1] | 92 |

TABLE 2b-continued
| BC No. | Structure | C |
|---|---|---|
| BC19405 | 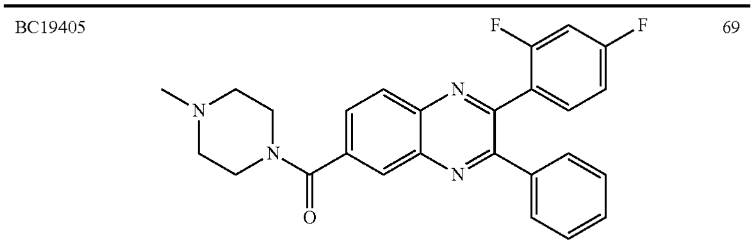 | 69 |
| BC19406 | 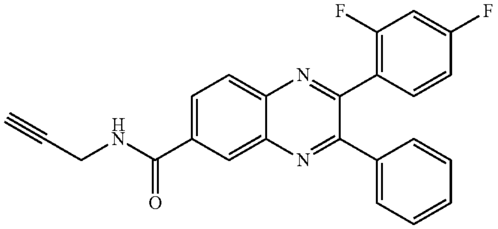 [SMILES: C#CCNC(=O)c1ccc2nc(-c3ccc(F)cc3F)c(-c3ccccc3)nc2c1] | 93 |
| BC19445 | 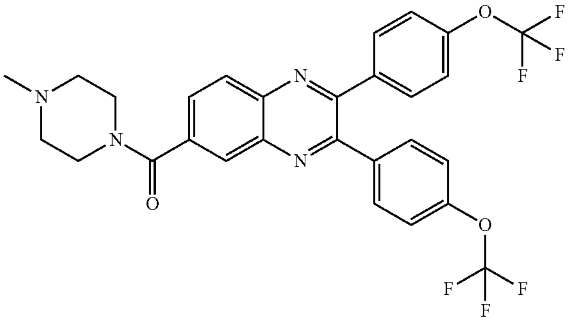 [SMILES: CN1CCN(C(=O)c2ccc3nc(-c4ccc(OC(F)(F)F)cc4)c(-c4ccc(OC(F)(F)F)cc4)nc3c2)CC1] | 14 |
| BC19447 | 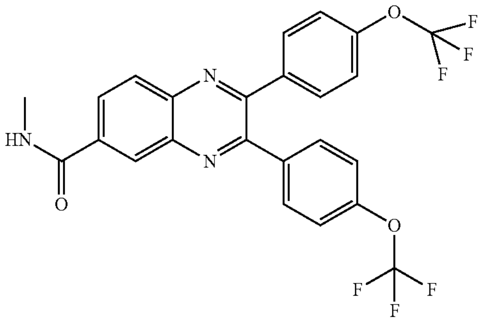 [SMILES: CNC(=O)c1ccc2nc(-c3ccc(OC(F)(F)F)cc3)c(-c3ccc(OC(F)(F)F)cc3)nc2c1] | 50 |
| BC19450 | 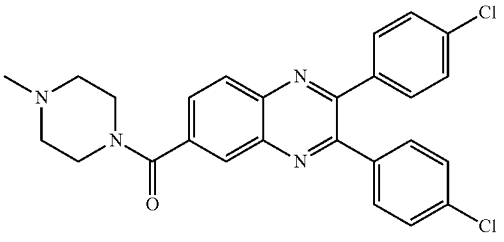 [SMILES: CN1CCN(C(=O)c2ccc3nc(-c4ccc(Cl)cc4)c(-c4ccc(Cl)cc4)nc3c2)CC1] | 78 |

TABLE 2b-continued
| BC No. | Structure | C |
|---|---|---|
| BC19451 | 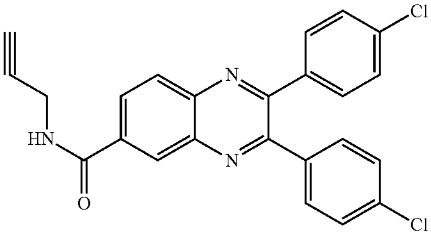 [SMILES: C#CCNC(=O)c1ccc2nc(-c3ccc(Cl)cc3)c(-c3ccc(Cl)cc3)nc2c1] | 57 |
| BC19453 | 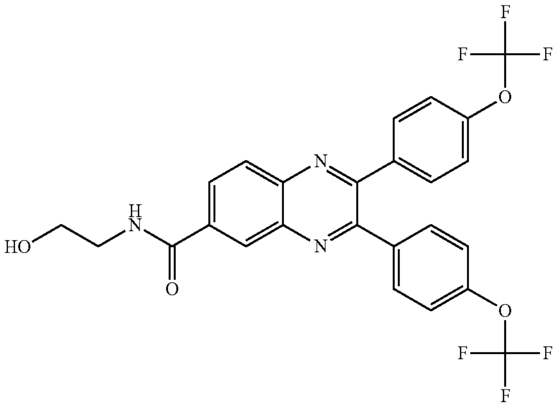 [SMILES: O=C(NCCO)c1ccc2nc(-c3ccc(OC(F)(F)F)cc3)c(-c3ccc(OC(F)(F)F)cc3)nc2c1] | 88 |
| BC19497 | 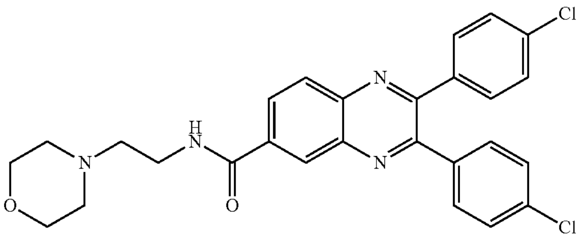 [SMILES: O=C(NCCN1CCOCC1)c1ccc2nc(-c3ccc(Cl)cc3)c(-c3ccc(Cl)cc3)nc2c1] | 49 |
| BC19498 | 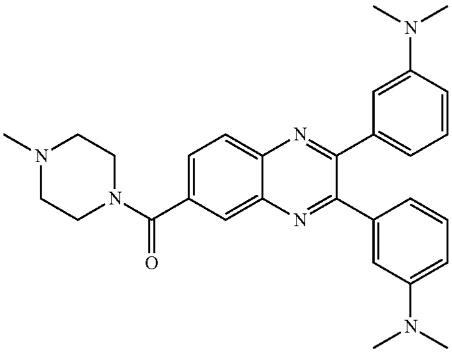 | 66 |

TABLE 2b-continued
| BC No. | Structure | C |
|---|---|---|
| BC19503 | 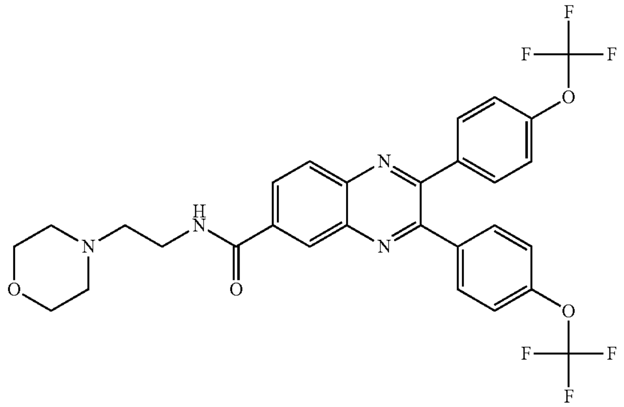 [SMILES: O=C(NCCN1CCOCC1)c1ccc2nc(-c3ccc(OC(F)(F)F)cc3)c(-c3ccc(OC(F)(F)F)cc3)nc2c1] | 43 |
| BC19513 | 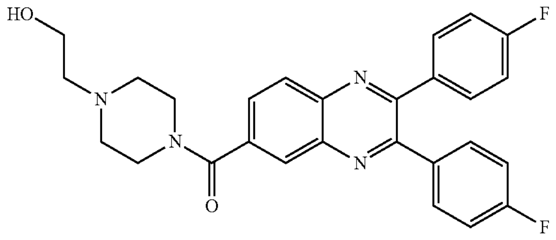 [SMILES: O=C(c1ccc2nc(-c3ccc(F)cc3)c(-c3ccc(F)cc3)nc2c1)N1CCN(CCO)CC1] | 49 |
| BC19514 | 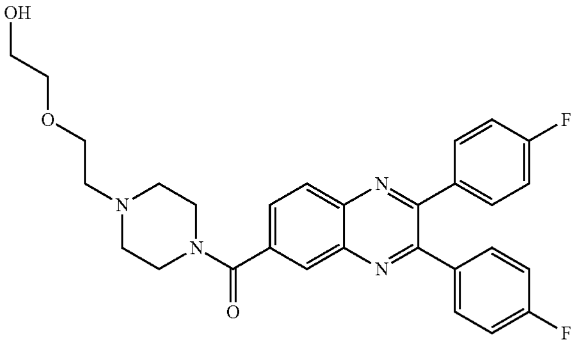 [SMILES: O=C(c1ccc2nc(-c3ccc(F)cc3)c(-c3ccc(F)cc3)nc2c1)N1CCN(CCOCCO)CC1] | 73 |
| BC19185 | 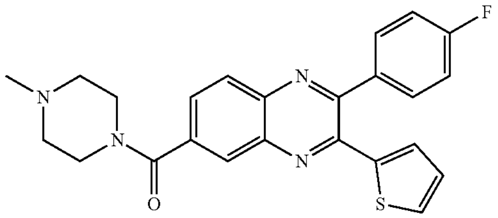 [SMILES: CN1CCN(C(=O)c2ccc3nc(-c4ccc(F)cc4)c(-c4cccs4)nc3c2)CC1] | 94 |
| BC19120 | 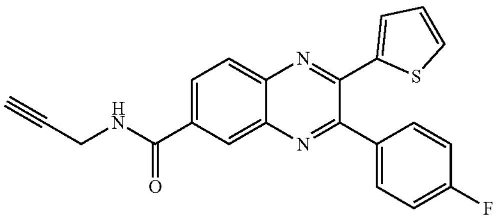 [SMILES: C#CCNC(=O)c1ccc2nc(-c3cccs3)c(-c3ccc(F)cc3)nc2c1] | 84 |

TABLE 3
| BC No. | Structure | C |
| --- | --- | --- |
| BC19403 | 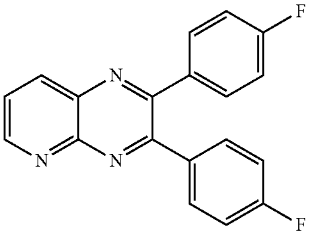 [SMILES: Fc1ccc(-c2nc3cccnc3nc2-c2ccc(F)cc2)cc1] | 68 |
| BC19408 | 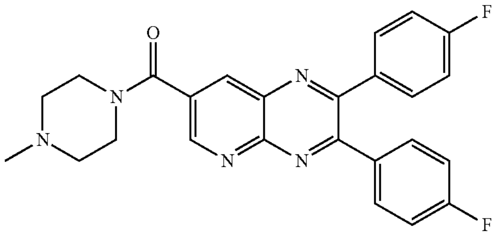 [SMILES: CN1CCN(C(=O)c2cnc3nc(-c4ccc(F)cc4)c(-c4ccc(F)cc4)nc3c2)CC1] | 95 |
| BC19512 | 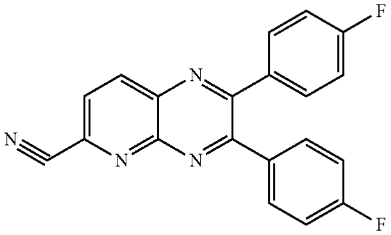 [SMILES: N#Cc1ccc2nc(-c3ccc(F)cc3)c(-c3ccc(F)cc3)nc2n1] | 85 |
| BC19448 | 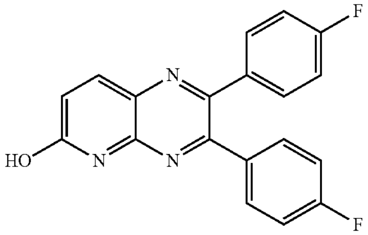 [SMILES: Oc1ccc2nc(-c3ccc(F)cc3)c(-c3ccc(F)cc3)nc2n1] | 78 |
| BC19666 | 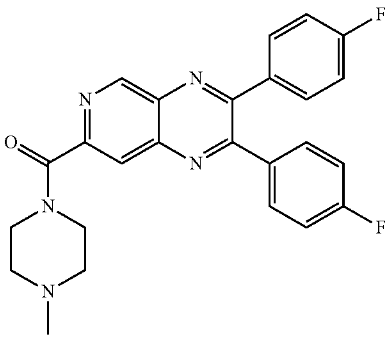 [SMILES: CN1CCN(C(=O)c2cc3nc(-c4ccc(F)cc4)c(-c4ccc(F)cc4)nc3cn2)CC1] | 70 |

TABLE 4
| BC No. | Structure | C |
|---|---|---|
| BC19101 | 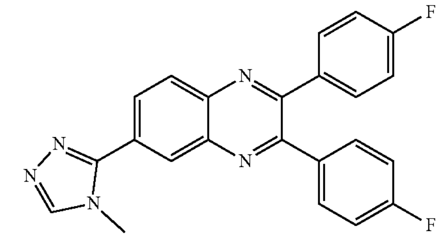 [SMILES: Cn1cnnc1-c1ccc2nc(-c3ccc(F)cc3)c(-c3ccc(F)cc3)nc2c1] | 53 |
| BC19139 | 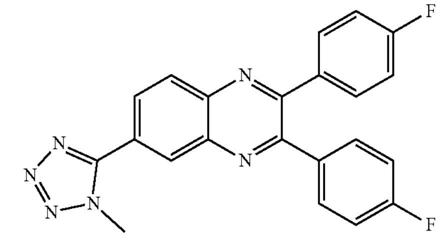 [SMILES: Cn1nnnc1-c1ccc2nc(-c3ccc(F)cc3)c(-c3ccc(F)cc3)nc2c1] | 29 |
| BC19140 | 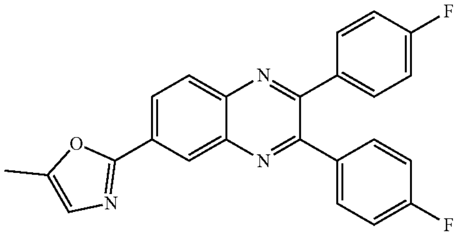 [SMILES: Cc1cnc(-c2ccc3nc(-c4ccc(F)cc4)c(-c4ccc(F)cc4)nc3c2)o1] | 90 |
| BC19141 | 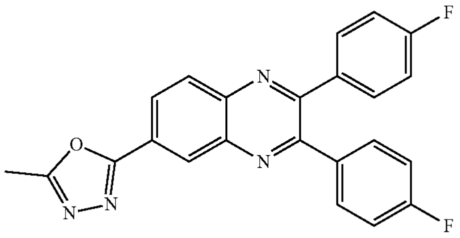 [SMILES: Cc1nnc(-c2ccc3nc(-c4ccc(F)cc4)c(-c4ccc(F)cc4)nc3c2)o1] | 62 |
| BC19143 | 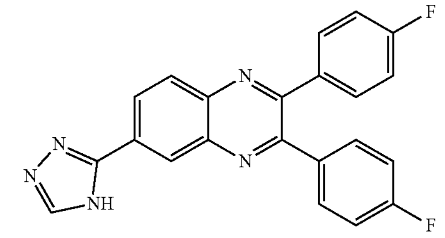 | 80 |
| BC19148 | 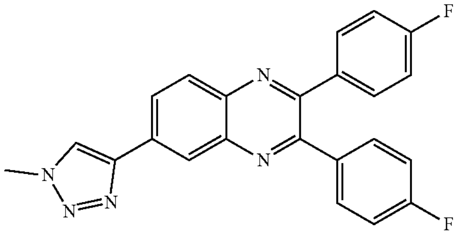 | 80 |

TABLE 4-continued
| BC No. | Structure | C |
|---|---|---|
| BC19150 | 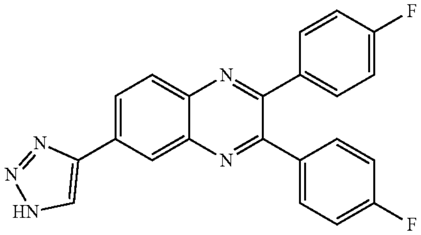 [SMILES: Fc1ccc(-c2nc3ccc(-c4c[nH]nn4)cc3nc2-c2ccc(F)cc2)cc1] | 89 |
| BC19238 | 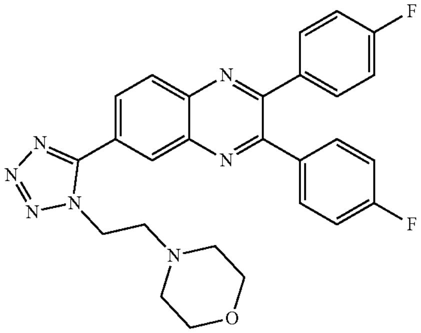 [SMILES: Fc1ccc(-c2nc3ccc(-c4nnnn4CCN4CCOCC4)cc3nc2-c2ccc(F)cc2)cc1] | 68 |
| BC19240 | 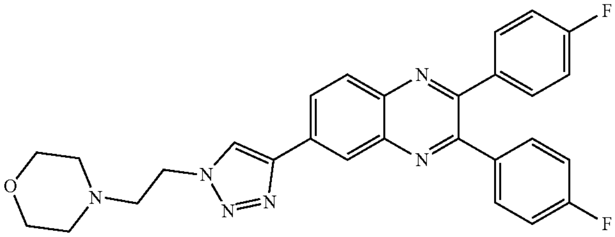 [SMILES: Fc1ccc(-c2nc3ccc(-c4cn(CCN5CCOCC5)nn4)cc3nc2-c2ccc(F)cc2)cc1] | 27 |
| BC19241 | 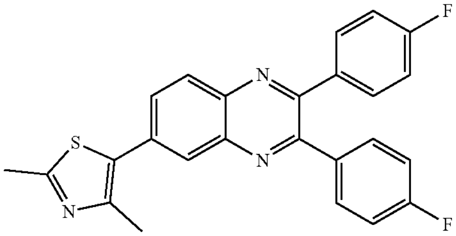 [SMILES: Cc1nc(C)c(-c2ccc3nc(-c4ccc(F)cc4)c(-c4ccc(F)cc4)nc3c2)s1] | 79 |
| BC19242 | 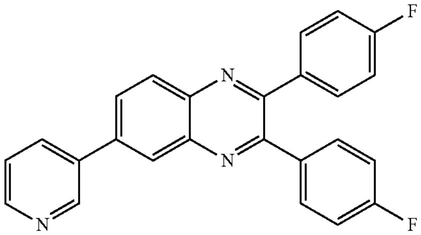 [SMILES: Fc1ccc(-c2nc3ccc(-c4cccnc4)cc3nc2-c2ccc(F)cc2)cc1] | 72 |
| BC19243 | 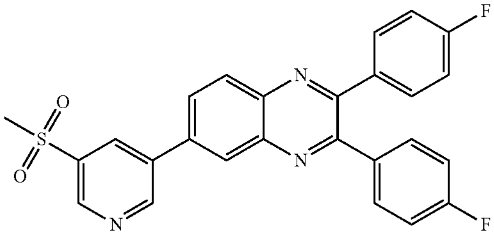 [SMILES: CS(=O)(=O)c1cncc(-c2ccc3nc(-c4ccc(F)cc4)c(-c4ccc(F)cc4)nc3c2)c1] | 64 |

TABLE 4-continued
| BC No. | Structure | C |
|---|---|---|
| BC19244 | 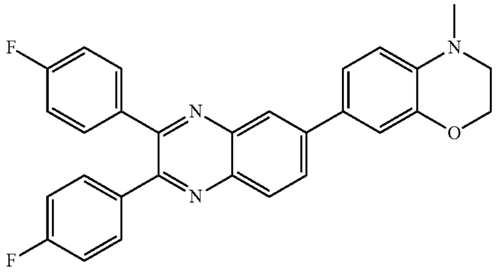 [SMILES: CN1CCOc2cc(-c3ccc4nc(-c5ccc(F)cc5)c(-c5ccc(F)cc5)nc4c3)ccc21] | 86 |
| BC19245 | 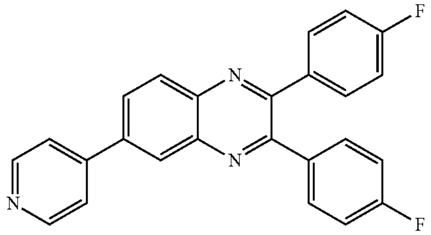 [SMILES: Fc1ccc(-c2nc3ccc(-c4ccncc4)cc3nc2-c2ccc(F)cc2)cc1] | 67 |
| BC19246 | 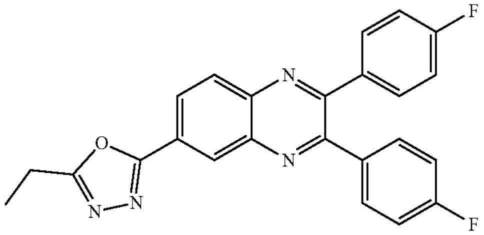 [SMILES: CCc1nnc(-c2ccc3nc(-c4ccc(F)cc4)c(-c4ccc(F)cc4)nc3c2)o1] | 58 |
| BC19247 | 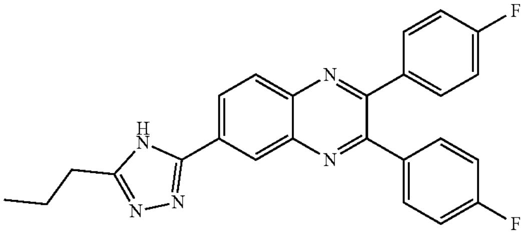 [SMILES: CCCc1nnc(-c2ccc3nc(-c4ccc(F)cc4)c(-c4ccc(F)cc4)nc3c2)[nH]1] | 94 |
| BC19250 | 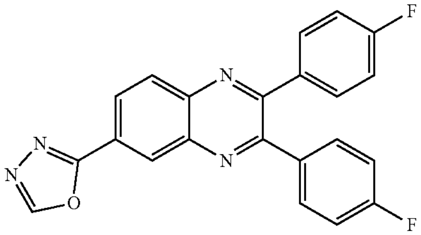 [SMILES: Fc1ccc(-c2nc3ccc(-c4nnco4)cc3nc2-c2ccc(F)cc2)cc1] | 13 |
| BC19301 | 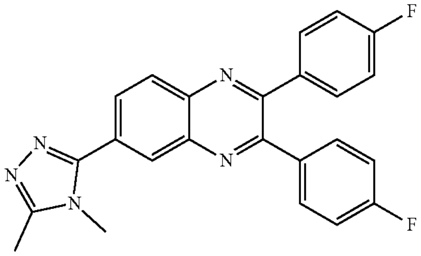 [SMILES: Cc1nnc(-c2ccc3nc(-c4ccc(F)cc4)c(-c4ccc(F)cc4)nc3c2)n1C] | 57 |

TABLE 4-continued
| BC No. | Structure | C |
| --- | --- | --- |
| BC19302 | 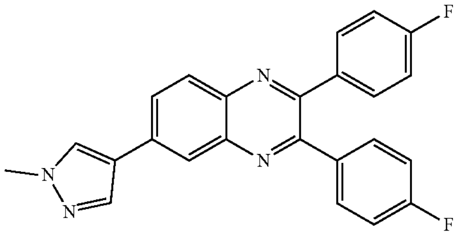 [SMILES: Cn1cc(-c2ccc3nc(-c4ccc(F)cc4)c(-c4ccc(F)cc4)nc3c2)cn1] | 58 |
| BC19304 | 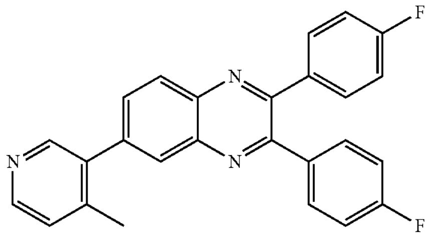 [SMILES: Cc1ccncc1-c1ccc2nc(-c3ccc(F)cc3)c(-c3ccc(F)cc3)nc2c1] | 69 |
| BC19305 | 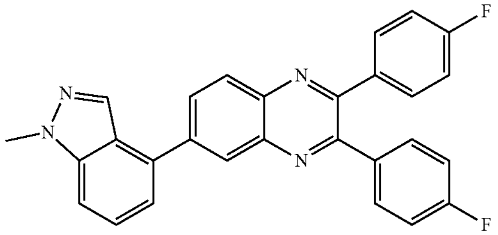 [SMILES: Cn1ncc2c(-c3ccc4nc(-c5ccc(F)cc5)c(-c5ccc(F)cc5)nc4c3)cccc21] | 93 |
| BC19306 | 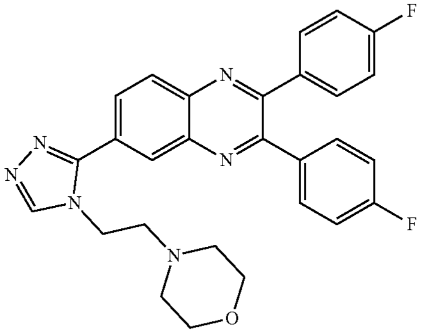 [SMILES: Fc1ccc(-c2nc3ccc(-c4nncn4CCN4CCOCC4)cc3nc2-c2ccc(F)cc2)cc1] | 76 |
| BC19396 | 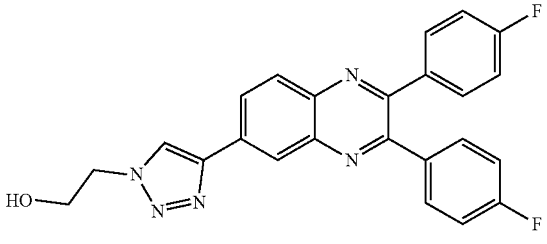 [SMILES: OCCn1cc(-c2ccc3nc(-c4ccc(F)cc4)c(-c4ccc(F)cc4)nc3c2)nn1] | 60 |
| BC19404 | 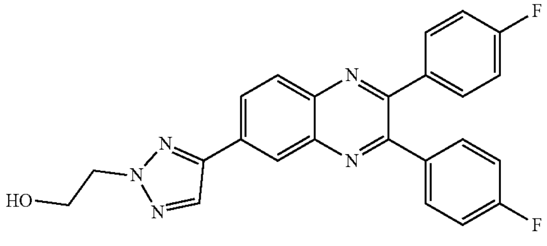 [SMILES: OCCn1ncc(-c2ccc3nc(-c4ccc(F)cc4)c(-c4ccc(F)cc4)nc3c2)n1] | 65 |

TABLE 4-continued
| BC No. | Structure | C |
| --- | --- | --- |
| BC19112 | 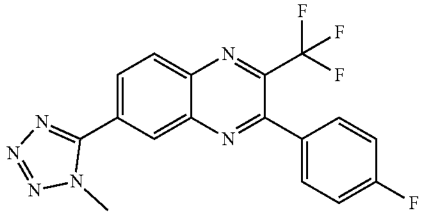 [SMILES: Cn1nnnc1-c1ccc2nc(C(F)(F)F)c(-c3ccc(F)cc3)nc2c1] | 86 |
| BC19152 | 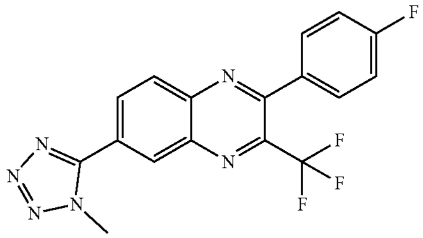 [SMILES: Cn1nnnc1-c1ccc2nc(-c3ccc(F)cc3)c(C(F)(F)F)nc2c1] | 93 |
| BC19159 | 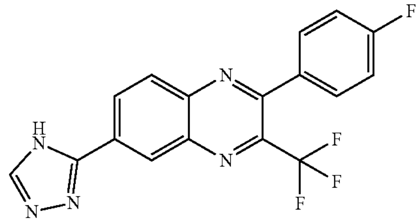 [SMILES: Fc1ccc(-c2nc3ccc(-c4nnc[nH]4)cc3nc2C(F)(F)F)cc1] | 92 |
| BC19401 | 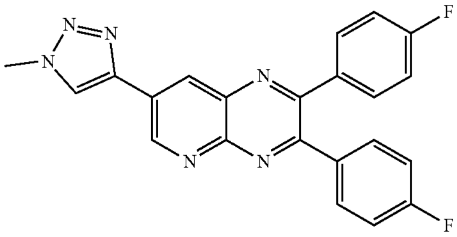 [SMILES: Cn1cc(-c2cnc3nc(-c4ccc(F)cc4)c(-c4ccc(F)cc4)nc3c2)nn1] | 55 |
| BC19402 | 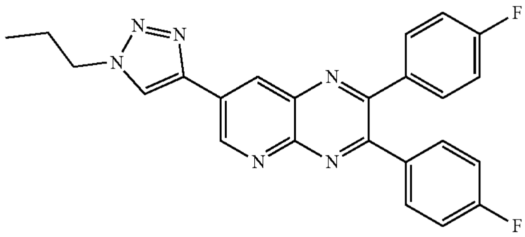 [SMILES: CCCn1cc(-c2cnc3nc(-c4ccc(F)cc4)c(-c4ccc(F)cc4)nc3c2)nn1] | 64 |
| BC19619 | 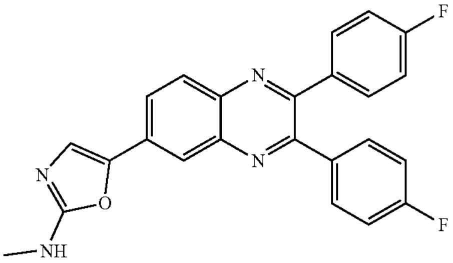 [SMILES: CNc1ncc(-c2ccc3nc(-c4ccc(F)cc4)c(-c4ccc(F)cc4)nc3c2)o1] | 55 |

TABLE 4-continued
| BC No. | Structure | C |
|---|---|---|
| BC19664 | 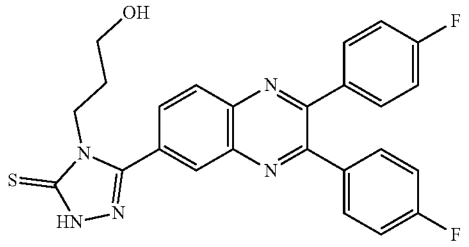 [SMILES: OCCCn1c(-c2ccc3nc(-c4ccc(F)cc4)c(-c4ccc(F)cc4)nc3c2)n[nH]c1=S] | 70 |
| BC19665 | 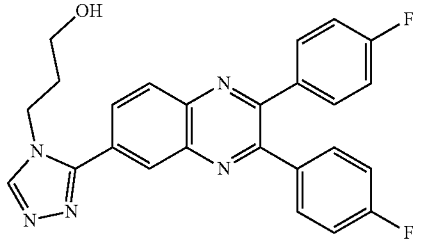 [SMILES: OCCCn1cnnc1-c1ccc2nc(-c3ccc(F)cc3)c(-c3ccc(F)cc3)nc2c1] | 58 |
| BC19667 | 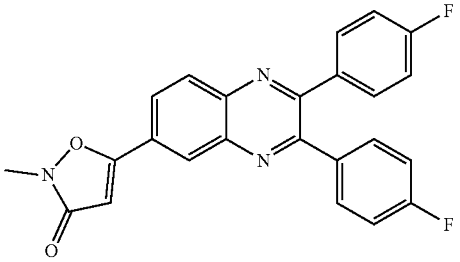 [SMILES: Cn1oc(-c2ccc3nc(-c4ccc(F)cc4)c(-c4ccc(F)cc4)nc3c2)cc1=O] | 38 |
| BC19496 | 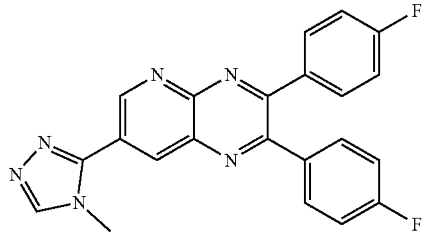 | 95 |
TABLE 5
| BC No. | Structure | C |
|---|---|---|
| BC19103 | 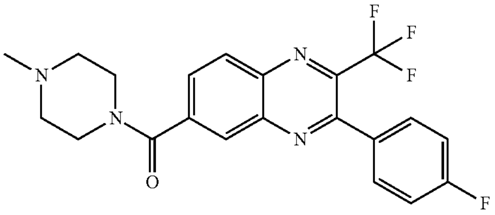 [SMILES: CN1CCN(C(=O)c2ccc3nc(C(F)(F)F)c(-c4ccc(F)cc4)nc3c2)CC1] | 92 |
| BC19142 | 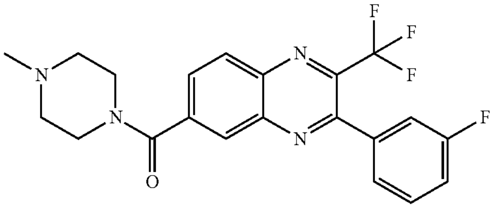 [SMILES: CN1CCN(C(=O)c2ccc3nc(C(F)(F)F)c(-c4cccc(F)c4)nc3c2)CC1] | 94 |

TABLE 5-continued
| BC No. | Structure | C |
|---|---|---|
| BC19307 | 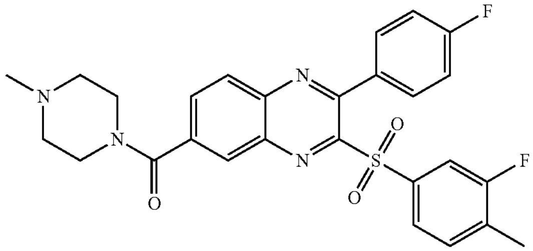 | 31 |
| BC19308 | 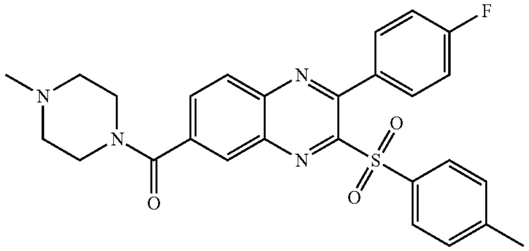 | 48 |
| BC19395 | 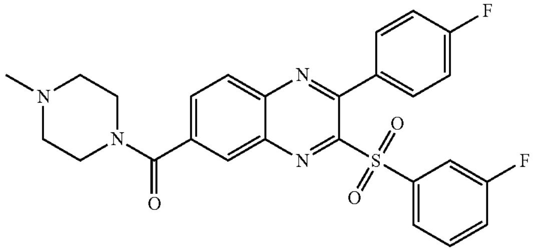 [SMILES: CN1CCN(C(=O)c2ccc3nc(-c4ccc(F)cc4)c(S(=O)(=O)c4cccc(F)c4)nc3c2)CC1] | 71 |
TABLE 6
| BC No. | Structure | C |
|---|---|---|
| BC19321 | 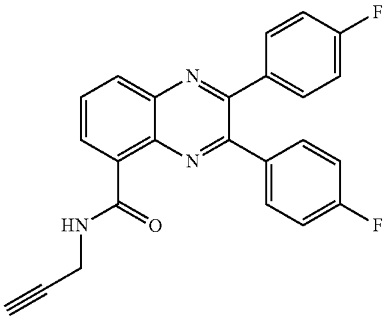 [SMILES: C#CCNC(=O)c1cccc2nc(-c3ccc(F)cc3)c(-c3ccc(F)cc3)nc12] | 72 |
TABLE 6-continued
| BC No. | Structure | C |
|---|---|---|
| BC19400 | 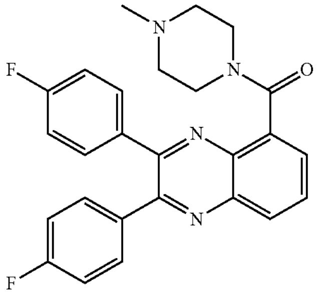 [SMILES: CN1CCN(C(=O)c2cccc3nc(-c4ccc(F)cc4)c(-c4ccc(F)cc4)nc23)CC1] | 76 |
TABLE 7
| BC No. | Structure | C |
|---|---|---|
| BC19195 | 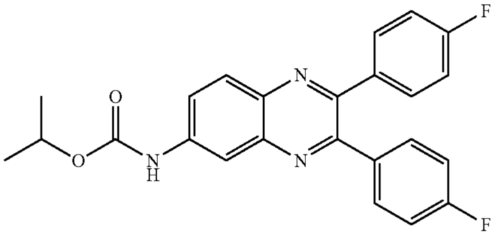 [SMILES: CC(C)OC(=O)Nc1ccc2nc(-c3ccc(F)cc3)c(-c3ccc(F)cc3)nc2c1] | 90 |

TABLE 7-continued
| BC No. | Structure | C |
|---|---|---|
| BC19239 | 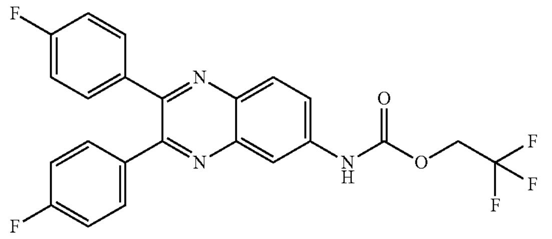 [SMILES: O=C(Nc1ccc2nc(-c3ccc(F)cc3)c(-c3ccc(F)cc3)nc2c1)OCC(F)(F)F] | 66 |
| BC19251 | 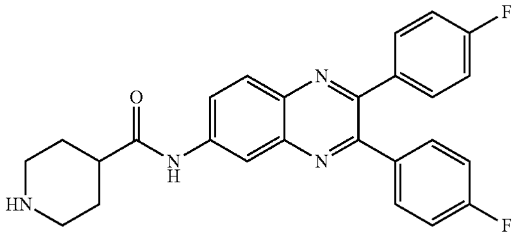 [SMILES: O=C(Nc1ccc2nc(-c3ccc(F)cc3)c(-c3ccc(F)cc3)nc2c1)C1CCNCC1] | 0 |
| BC19309 | 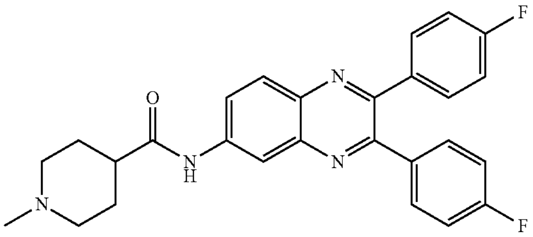 [SMILES: CN1CCC(C(=O)Nc2ccc3nc(-c4ccc(F)cc4)c(-c4ccc(F)cc4)nc3c2)CC1] | 18 |
| BC19310 | 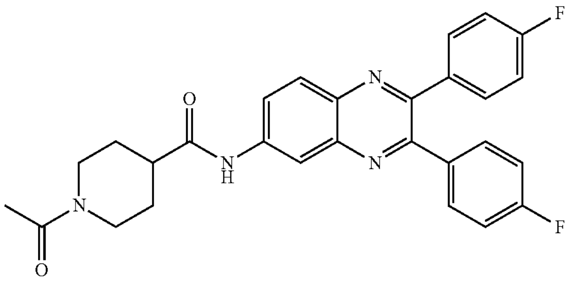 [SMILES: CC(=O)N1CCC(C(=O)Nc2ccc3nc(-c4ccc(F)cc4)c(-c4ccc(F)cc4)nc3c2)CC1] | 52 |
| BC19311 | 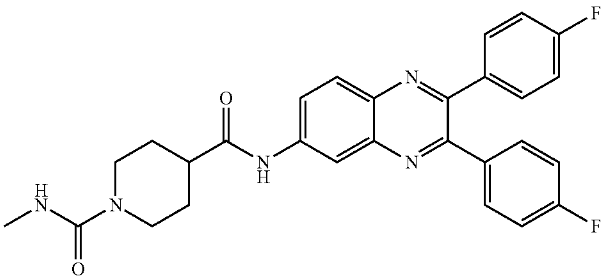 [SMILES: CNC(=O)N1CCC(C(=O)Nc2ccc3nc(-c4ccc(F)cc4)c(-c4ccc(F)cc4)nc3c2)CC1] | 63 |
| BC19312 | 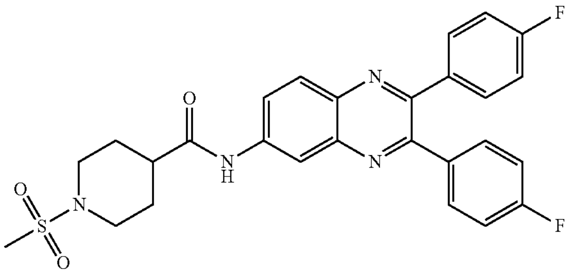 [SMILES: CS(=O)(=O)N1CCC(C(=O)Nc2ccc3nc(-c4ccc(F)cc4)c(-c4ccc(F)cc4)nc3c2)CC1] | 54 |

TABLE 7-continued
| BC No. | Structure | C |
|---|---|---|
| BC19313 | 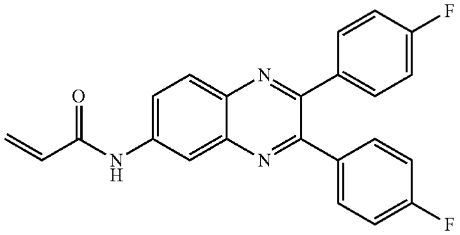 [SMILES: C=CC(=O)Nc1ccc2nc(-c3ccc(F)cc3)c(-c3ccc(F)cc3)nc2c1] | 91 |
| BC19314 | 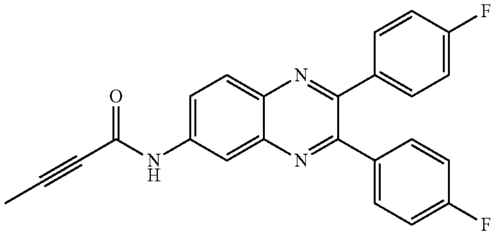 [SMILES: CC#CC(=O)Nc1ccc2nc(-c3ccc(F)cc3)c(-c3ccc(F)cc3)nc2c1] | 33 |
| BC19315 | 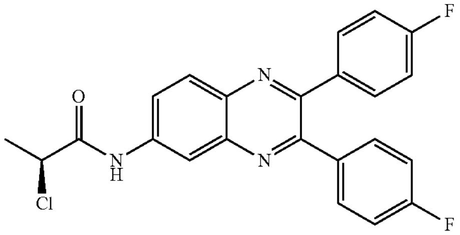 [SMILES: C[C@H](Cl)C(=O)Nc1ccc2nc(-c3ccc(F)cc3)c(-c3ccc(F)cc3)nc2c1] | 89 |
| BC19397 | 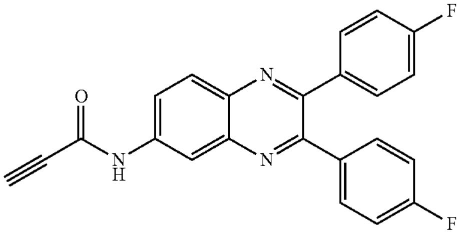 [SMILES: C#CC(=O)Nc1ccc2nc(-c3ccc(F)cc3)c(-c3ccc(F)cc3)nc2c1] | 65 |
| BC19494 | 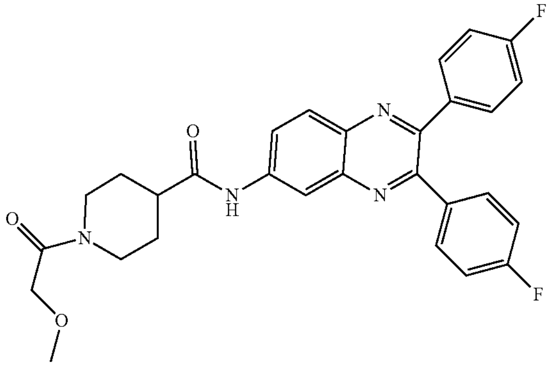 [SMILES: COCC(=O)N1CCC(C(=O)Nc2ccc3nc(-c4ccc(F)cc4)c(-c4ccc(F)cc4)nc3c2)CC1] | 52 |
| BC19510 | 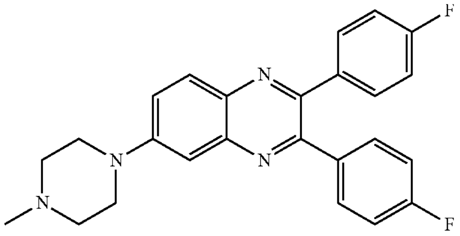 [SMILES: CN1CCN(c2ccc3nc(-c4ccc(F)cc4)c(-c4ccc(F)cc4)nc3c2)CC1] | 41 |

TABLE 7-continued
| BC No. | Structure | C |
| --- | --- | --- |
| BC19511 | 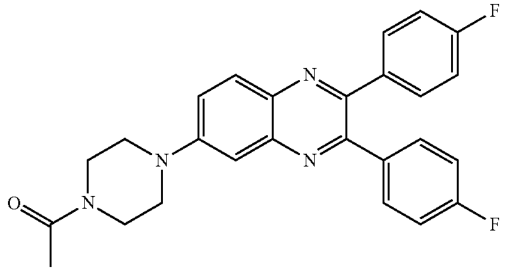 [SMILES: CC(=O)N1CCN(c2ccc3nc(-c4ccc(F)cc4)c(-c4ccc(F)cc4)nc3c2)CC1] | 26 |
| BC19563 | 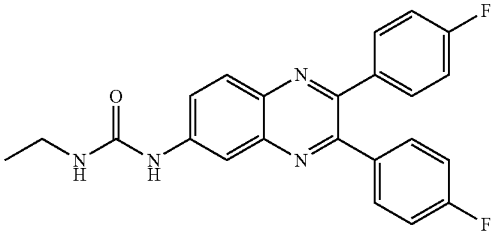 [SMILES: CCNC(=O)Nc1ccc2nc(-c3ccc(F)cc3)c(-c3ccc(F)cc3)nc2c1] | 90 |
| BC19564 | 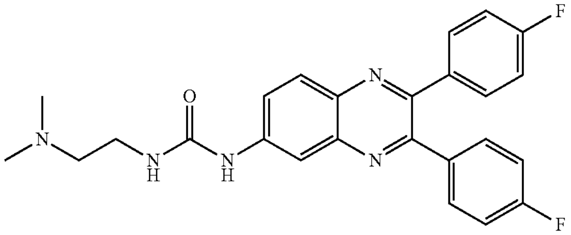 [SMILES: CN(C)CCNC(=O)Nc1ccc2nc(-c3ccc(F)cc3)c(-c3ccc(F)cc3)nc2c1] | 5 |
| BC19565 | 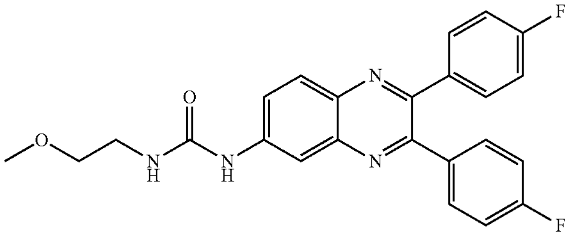 [SMILES: COCCNC(=O)Nc1ccc2nc(-c3ccc(F)cc3)c(-c3ccc(F)cc3)nc2c1] | 65 |
| BC19566 | 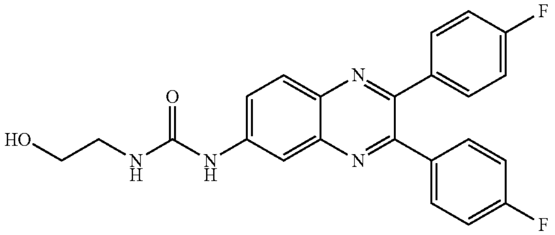 [SMILES: O=C(NCCO)Nc1ccc2nc(-c3ccc(F)cc3)c(-c3ccc(F)cc3)nc2c1] | 77 |
| BC19567 | 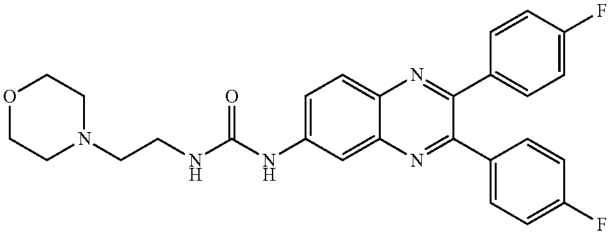 [SMILES: O=C(NCCN1CCOCC1)Nc1ccc2nc(-c3ccc(F)cc3)c(-c3ccc(F)cc3)nc2c1] | 46 |

TABLE 7-continued
| BC No. | Structure | C |
|---|---|---|
| BC19568 | 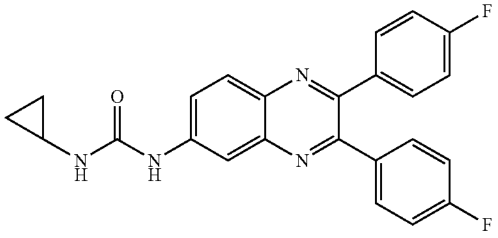 [SMILES: O=C(Nc1ccc2nc(-c3ccc(F)cc3)c(-c3ccc(F)cc3)nc2c1)NC1CC1] | 81 |
| BC19569 | 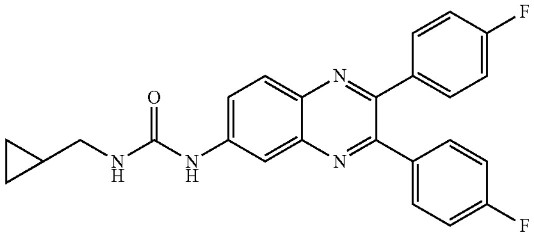 [SMILES: O=C(NCC1CC1)Nc1ccc2nc(-c3ccc(F)cc3)c(-c3ccc(F)cc3)nc2c1] | 57 |
| BC19570 | 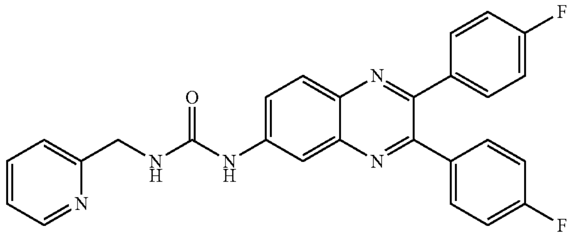 [SMILES: O=C(NCc1ccccn1)Nc1ccc2nc(-c3ccc(F)cc3)c(-c3ccc(F)cc3)nc2c1] | 29 |
| BC19571 | 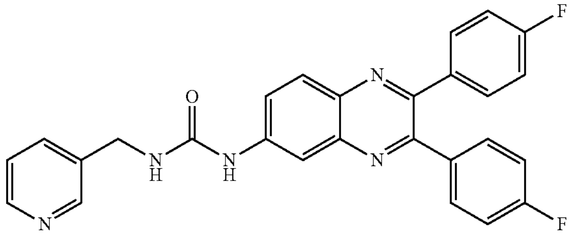 [SMILES: O=C(NCc1cccnc1)Nc1ccc2nc(-c3ccc(F)cc3)c(-c3ccc(F)cc3)nc2c1] | 10 |
| BC19572 | 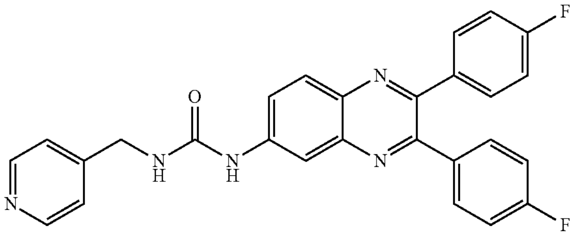 [SMILES: O=C(NCc1ccncc1)Nc1ccc2nc(-c3ccc(F)cc3)c(-c3ccc(F)cc3)nc2c1] | 26 |
| BC19573 | 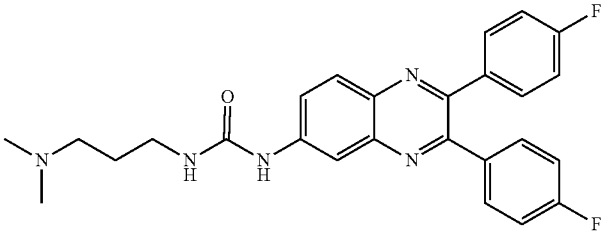 [SMILES: CN(C)CCCNC(=O)Nc1ccc2nc(-c3ccc(F)cc3)c(-c3ccc(F)cc3)nc2c1] | 11 |

TABLE 7-continued
| BC No. | Structure | C |
|---|---|---|
| BC19574 | 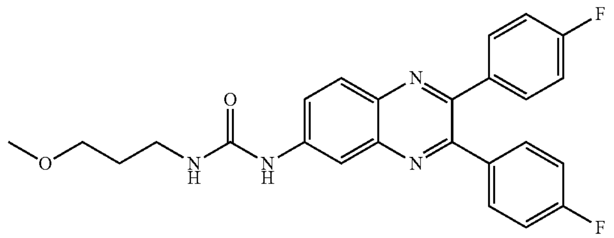 | 61 |
| BC19575 | 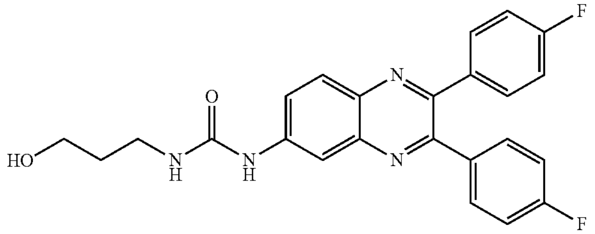 [SMILES: O=C(NCCCO)Nc1ccc2nc(-c3ccc(F)cc3)c(-c3ccc(F)cc3)nc2c1] | 78 |
| BC19576 | 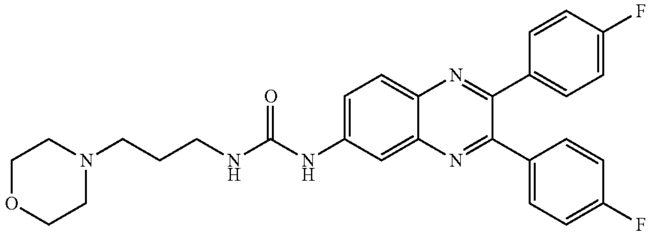 [SMILES: O=C(NCCCN1CCOCC1)Nc1ccc2nc(-c3ccc(F)cc3)c(-c3ccc(F)cc3)nc2c1] | 61 |
| BC19616 | 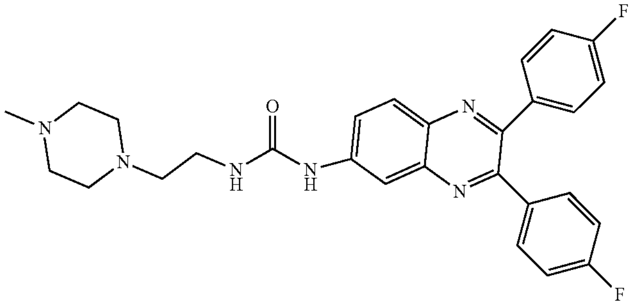 [SMILES: CN1CCN(CCNC(=O)Nc2ccc3nc(-c4ccc(F)cc4)c(-c4ccc(F)cc4)nc3c2)CC1] | 31 |
| BC19617 | 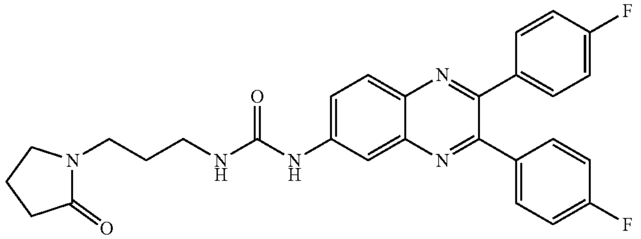 [SMILES: O=C(NCCCN1CCCC1=O)Nc1ccc2nc(-c3ccc(F)cc3)c(-c3ccc(F)cc3)nc2c1] | 58 |

TABLE 8
| BCNo. | Structure | A | B |
| --- | --- | --- | --- |
| BC20317 | 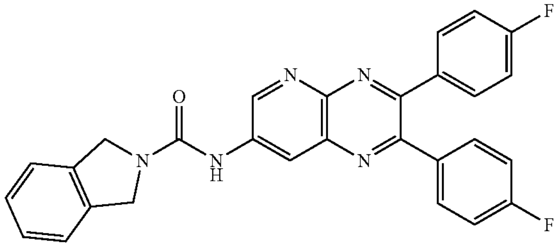 [SMILES: O=C(Nc1cnc2nc(-c3ccc(F)cc3)c(-c3ccc(F)cc3)nc2c1)N1Cc2ccccc2C1] | +++ | +++ |
| BC20321 | 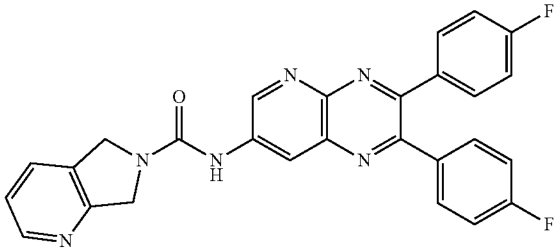 [SMILES: O=C(Nc1cnc2nc(-c3ccc(F)cc3)c(-c3ccc(F)cc3)nc2c1)N1Cc2cccnc2C1] | +++ | +++ |
| BC20330 | 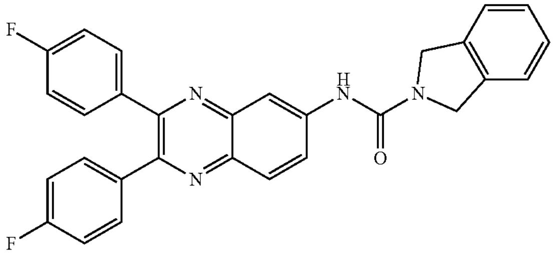 [SMILES: O=C(Nc1ccc2nc(-c3ccc(F)cc3)c(-c3ccc(F)cc3)nc2c1)N1Cc2ccccc2C1] | +++ | +++ |
| BC20333 | 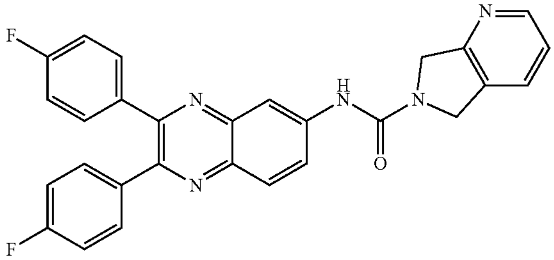 [SMILES: O=C(Nc1ccc2nc(-c3ccc(F)cc3)c(-c3ccc(F)cc3)nc2c1)N1Cc2cccnc2C1] | +++ | +++ |
| BC20334 | 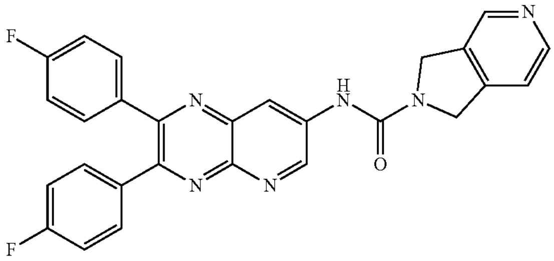 [SMILES: O=C(Nc1cnc2nc(-c3ccc(F)cc3)c(-c3ccc(F)cc3)nc2c1)N1Cc2ccncc2C1] | +++ | +++ |
| ZE18-0567 | 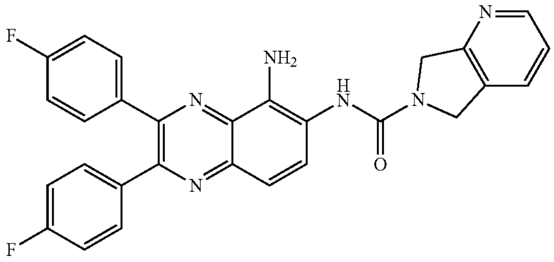 [SMILES: Nc1c(NC(=O)N2Cc3cccnc3C2)ccc2nc(-c3ccc(F)cc3)c(-c3ccc(F)cc3)nc12] | | |

TABLE 8-continued
| BCNo. | Structure | A | B |
|---|---|---|---|
| BC20218 | 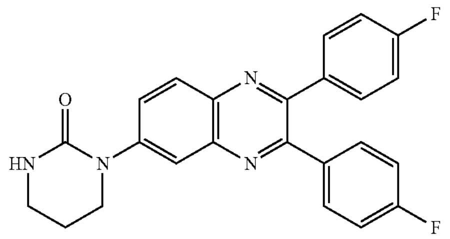 [SMILES: O=C1NCCCN1c1ccc2nc(-c3ccc(F)cc3)c(-c3ccc(F)cc3)nc2c1] | + | |
| BC20219 | 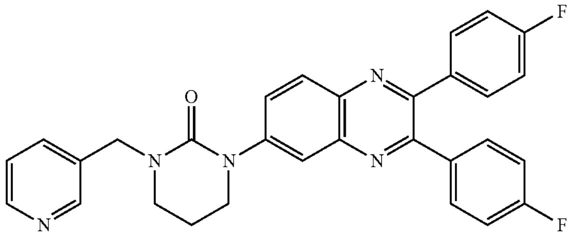 [SMILES: O=C1N(Cc2cccnc2)CCCN1c1ccc2nc(-c3ccc(F)cc3)c(-c3ccc(F)cc3)nc2c1] | + | |
| BC20226 | 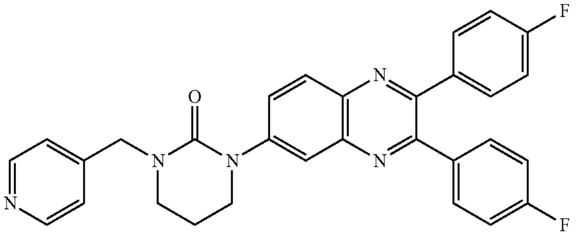 [SMILES: O=C1N(Cc2ccncc2)CCCN1c1ccc2nc(-c3ccc(F)cc3)c(-c3ccc(F)cc3)nc2c1] | ++ | |
| BC20277 | 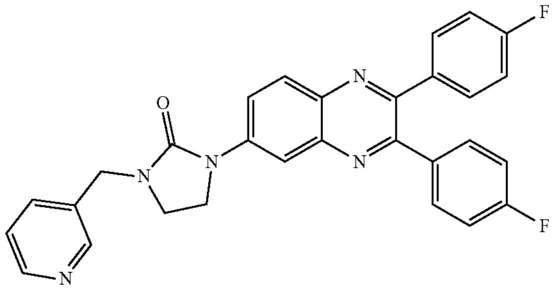 [SMILES: O=C1N(Cc2cccnc2)CCN1c1ccc2nc(-c3ccc(F)cc3)c(-c3ccc(F)cc3)nc2c1] | ++ | |
| BC20291 | 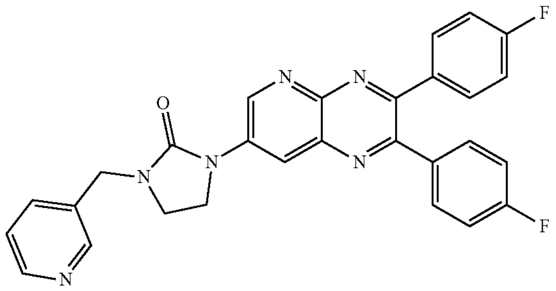 [SMILES: O=C1N(Cc2cccnc2)CCN1c1cnc2nc(-c3ccc(F)cc3)c(-c3ccc(F)cc3)nc2c1] | + | |
| BC20297 | 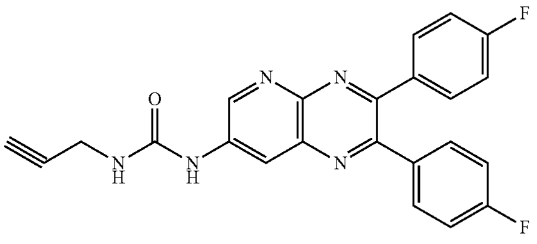 [SMILES: C#CCNC(=O)Nc1cnc2nc(-c3ccc(F)cc3)c(-c3ccc(F)cc3)nc2c1] | + | |

TABLE 8-continued
| BCNo. | Structure | A | B |
|---|---|---|---|
| BC20312 | 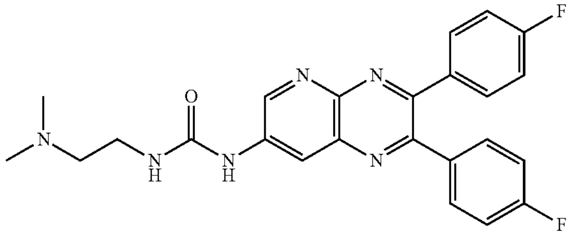 | + | |
| BC20298 | 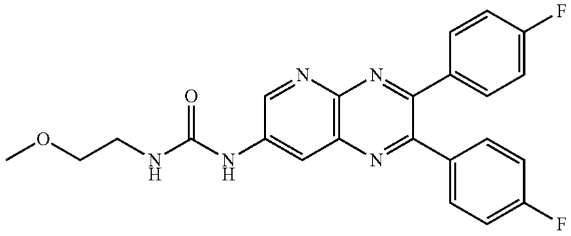 [SMILES: COCCNC(=O)Nc1cnc2nc(-c3ccc(F)cc3)c(-c3ccc(F)cc3)nc2c1] | + | |
| BC20299 | 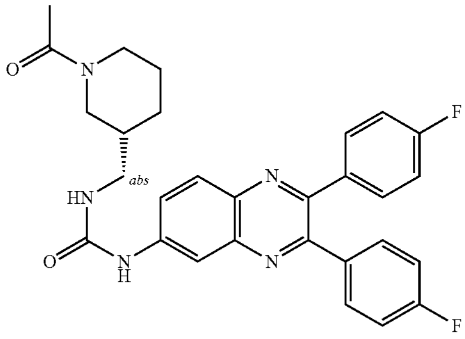 | ++ | |
| BC20300 | 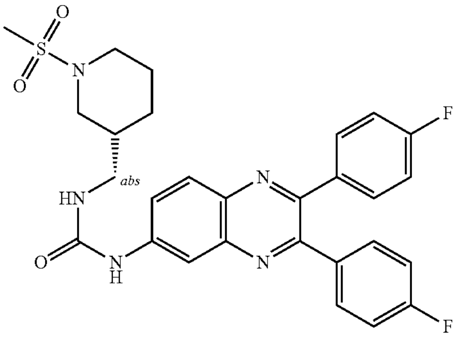 | ++ | |
| BC20217 | 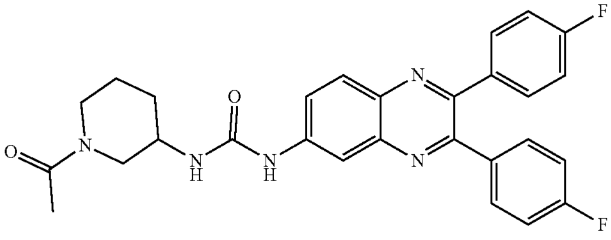 [SMILES: CC(=O)N1CCCC(NC(=O)Nc2ccc3nc(-c4ccc(F)cc4)c(-c4ccc(F)cc4)nc3c2)C1] | ++ | |

TABLE 8-continued
| BCNo. | Structure | A | B |
|---|---|---|---|
| BC20225 | 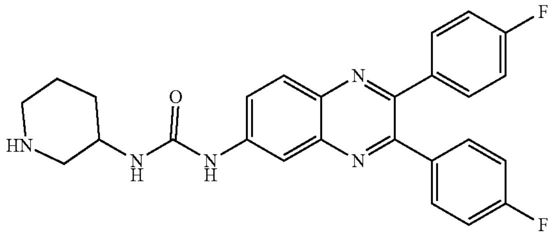 [SMILES: O=C(Nc1ccc2nc(-c3ccc(F)cc3)c(-c3ccc(F)cc3)nc2c1)NC1CCCNC1] | + | |
| BC20237 | 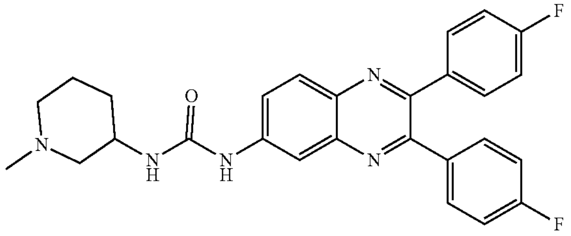 [SMILES: CN1CCCC(NC(=O)Nc2ccc3nc(-c4ccc(F)cc4)c(-c4ccc(F)cc4)nc3c2)C1] | + | |
| BC20238 | 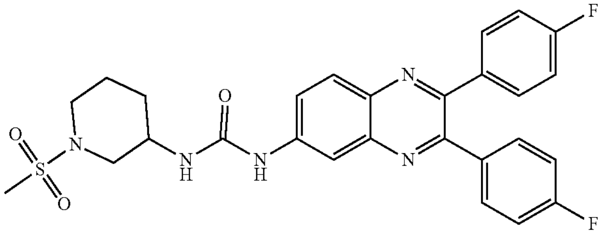 [SMILES: CS(=O)(=O)N1CCCC(NC(=O)Nc2ccc3nc(-c4ccc(F)cc4)c(-c4ccc(F)cc4)nc3c2)C1] | ++ | |
| BC20239 | 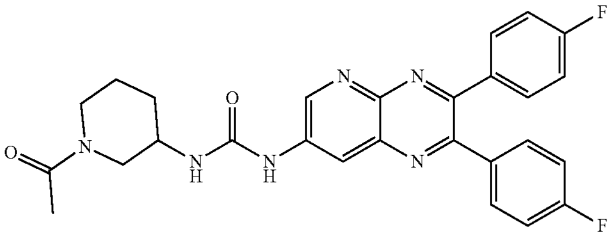 [SMILES: CC(=O)N1CCCC(NC(=O)Nc2cnc3nc(-c4ccc(F)cc4)c(-c4ccc(F)cc4)nc3c2)C1] | + | |
| BC20255 | 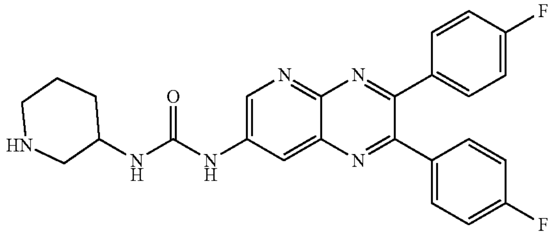 [SMILES: O=C(Nc1cnc2nc(-c3ccc(F)cc3)c(-c3ccc(F)cc3)nc2c1)NC1CCCNC1] | + | |
| BC20256 | 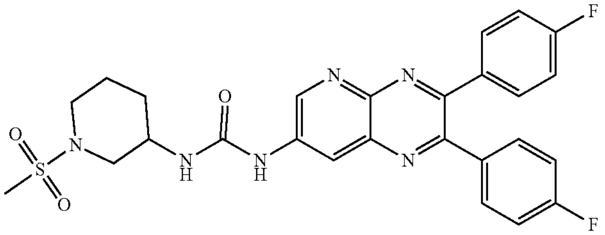 [SMILES: CS(=O)(=O)N1CCCC(NC(=O)Nc2cnc3nc(-c4ccc(F)cc4)c(-c4ccc(F)cc4)nc3c2)C1] | ++ | |

TABLE 8-continued
| BCNo. | Structure | A | B |
|---|---|---|---|
| BC20269 | 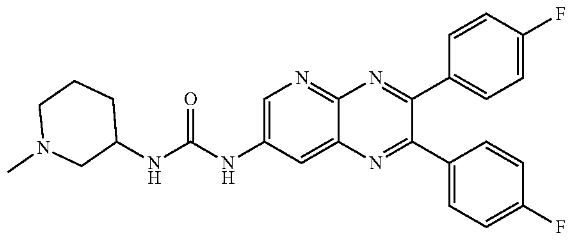 [SMILES: CN1CCCC(NC(=O)Nc2cnc3nc(-c4ccc(F)cc4)c(-c4ccc(F)cc4)nc3c2)C1] | + | |
| BC20293 | 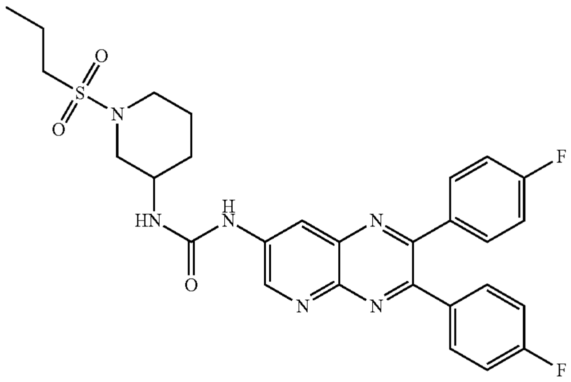 [SMILES: CCCS(=O)(=O)N1CCCC(NC(=O)Nc2cnc3nc(-c4ccc(F)cc4)c(-c4ccc(F)cc4)nc3c2)C1] | + | |
| BC20207 | 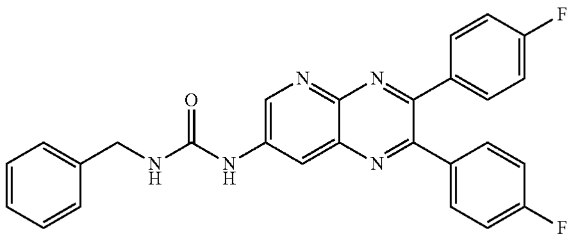 [SMILES: O=C(NCc1ccccc1)Nc1cnc2nc(-c3ccc(F)cc3)c(-c3ccc(F)cc3)nc2c1] | + | |
| BC20310 | 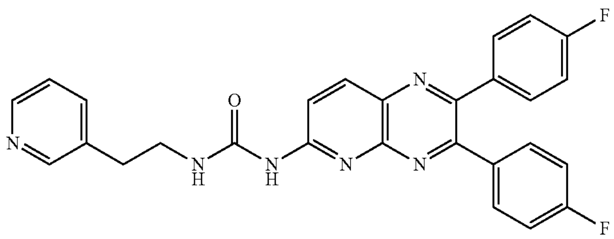 [SMILES: O=C(NCCc1cccnc1)Nc1ccc2nc(-c3ccc(F)cc3)c(-c3ccc(F)cc3)nc2n1] | +++ | |
| BC20311 | 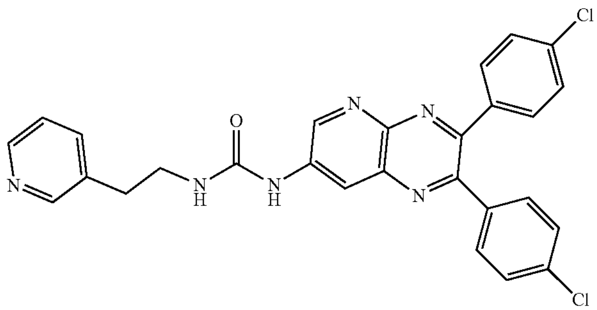 [SMILES: O=C(NCCc1cccnc1)Nc1cnc2nc(-c3ccc(Cl)cc3)c(-c3ccc(Cl)cc3)nc2c1] | +++ | +++ |

TABLE 8-continued
| BCNo. | Structure | A | B |
|---|---|---|---|
| BC20224 | 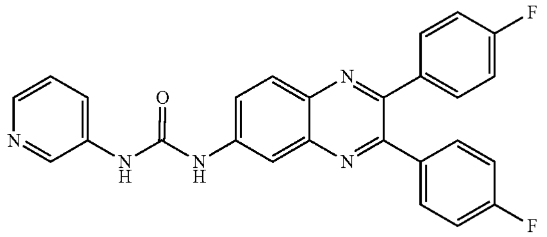 [SMILES: O=C(Nc1cccnc1)Nc1ccc2nc(-c3ccc(F)cc3)c(-c3ccc(F)cc3)nc2c1] | +++ | +++ |
| BC20254 | 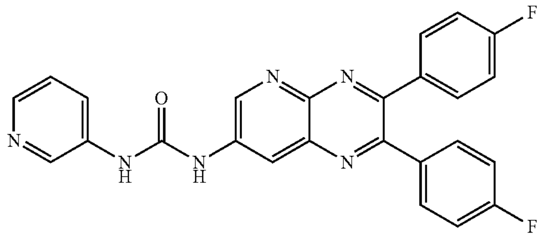 [SMILES: O=C(Nc1cccnc1)Nc1cnc2nc(-c3ccc(F)cc3)c(-c3ccc(F)cc3)nc2c1] | +++ | +++ |
| BC20213 | 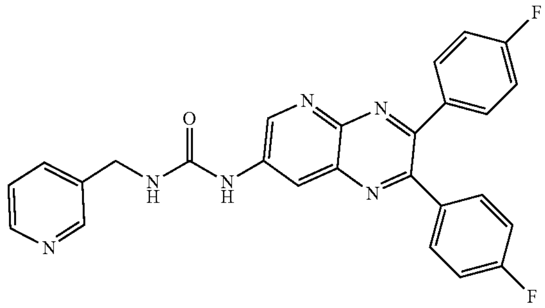 [SMILES: O=C(NCc1cccnc1)Nc1cnc2nc(-c3ccc(F)cc3)c(-c3ccc(F)cc3)nc2c1] | +++ | +++ |
| BC20316 | 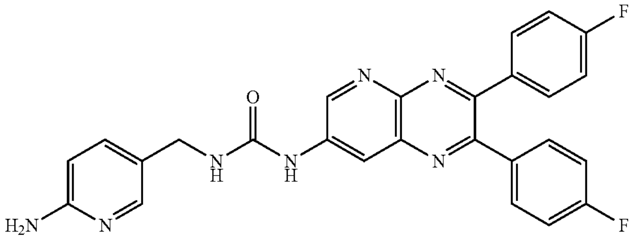 [SMILES: Nc1ccc(CNC(=O)Nc2cnc3nc(-c4ccc(F)cc4)c(-c4ccc(F)cc4)nc3c2)cn1] | +++ | +++ |
| BC20216 | 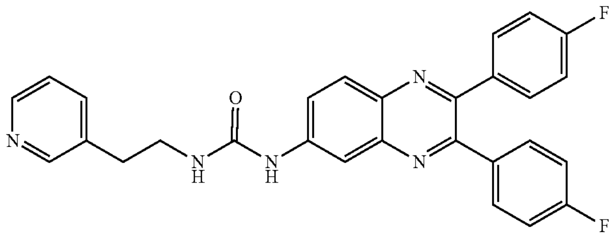 [SMILES: O=C(NCCc1cccnc1)Nc1ccc2nc(-c3ccc(F)cc3)c(-c3ccc(F)cc3)nc2c1] | +++ | +++ |
| BC20268 | 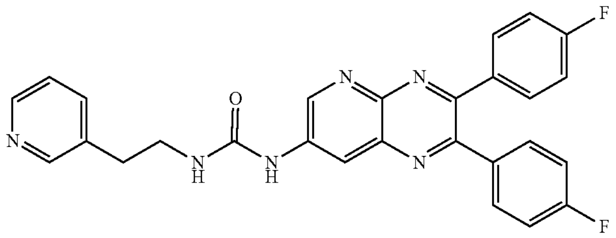 [SMILES: O=C(NCCc1cccnc1)Nc1cnc2nc(-c3ccc(F)cc3)c(-c3ccc(F)cc3)nc2c1] | +++ | +++ |

TABLE 8-continued
| BCNo. | Structure | A | B |
| --- | --- | --- | --- |
| BC20314 | 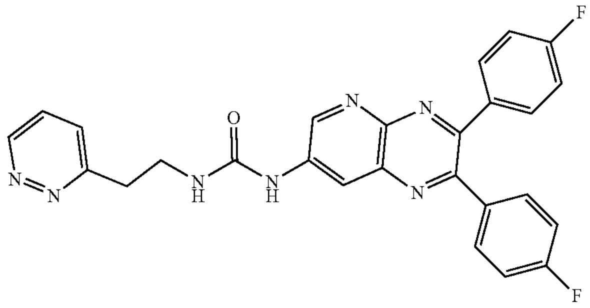 [SMILES: O=C(NCCc1cccnn1)Nc1cnc2nc(-c3ccc(F)cc3)c(-c3ccc(F)cc3)nc2c1] | +++ | +++ |
| BC20315 | 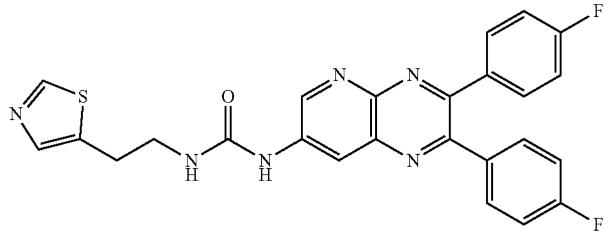 [SMILES: O=C(NCCc1cncs1)Nc1cnc2nc(-c3ccc(F)cc3)c(-c3ccc(F)cc3)nc2c1] | +++ | +++ |
| BC20318 | 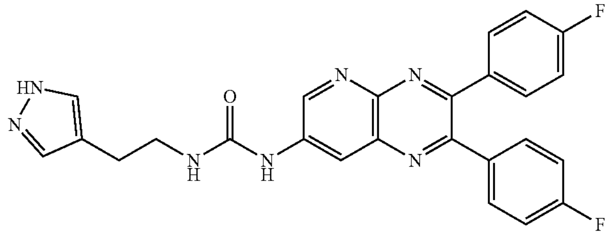 [SMILES: O=C(NCCc1cn[nH]c1)Nc1cnc2nc(-c3ccc(F)cc3)c(-c3ccc(F)cc3)nc2c1] | +++ | +++ |
| BC20320 | 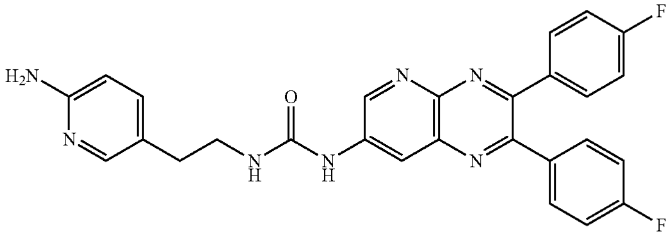 [SMILES: Nc1ccc(CCNC(=O)Nc2cnc3nc(-c4ccc(F)cc4)c(-c4ccc(F)cc4)nc3c2)cn1] | +++ | +++ |
| BC20331 | 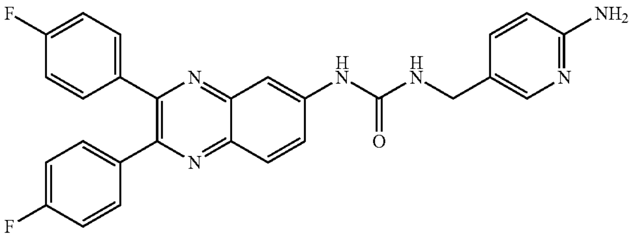 [SMILES: Nc1ccc(CNC(=O)Nc2ccc3nc(-c4ccc(F)cc4)c(-c4ccc(F)cc4)nc3c2)cn1] | +++ | +++ |
| BC20319 | 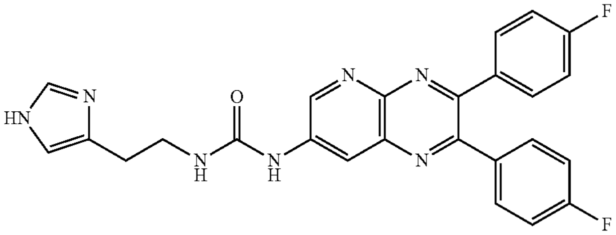 [SMILES: O=C(NCCc1c[nH]cn1)Nc1cnc2nc(-c3ccc(F)cc3)c(-c3ccc(F)cc3)nc2c1] | +++ | +++ |

TABLE 9
| BC No. | Structure | C |
|---|---|---|
| BC19504 | 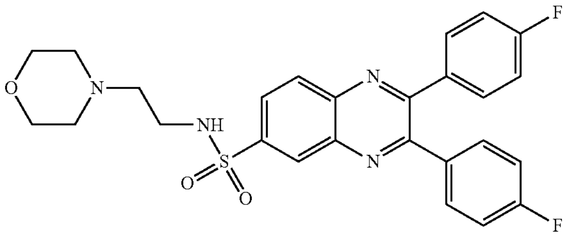 [SMILES: O=S(=O)(NCCN1CCOCC1)c1ccc2nc(-c3ccc(F)cc3)c(-c3ccc(F)cc3)nc2c1] | 58 |
| BC19505 | 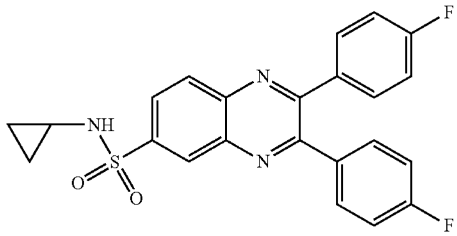 [SMILES: O=S(=O)(NC1CC1)c1ccc2nc(-c3ccc(F)cc3)c(-c3ccc(F)cc3)nc2c1] | 30 |
| BC19506 | 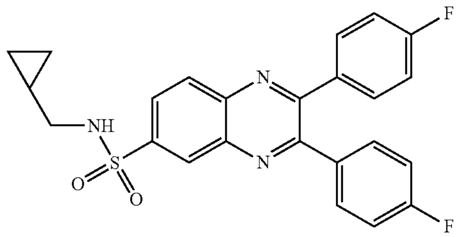 [SMILES: O=S(=O)(NCC1CC1)c1ccc2nc(-c3ccc(F)cc3)c(-c3ccc(F)cc3)nc2c1] | 66 |
| BC19507 | 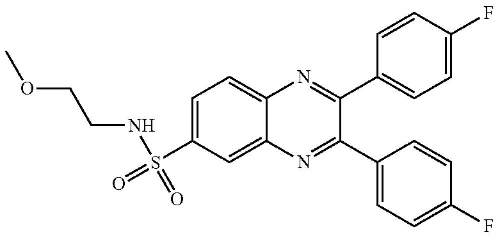 [SMILES: COCCNS(=O)(=O)c1ccc2nc(-c3ccc(F)cc3)c(-c3ccc(F)cc3)nc2c1] | 53 |
| BC19508 | 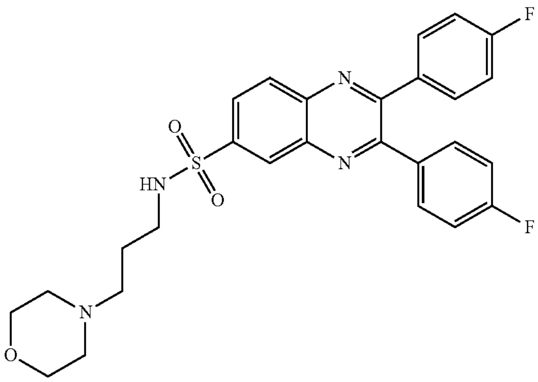 [SMILES: O=S(=O)(NCCCN1CCOCC1)c1ccc2nc(-c3ccc(F)cc3)c(-c3ccc(F)cc3)nc2c1] | 28 |

TABLE 9-continued
| BC No. | Structure | C |
|---|---|---|
| BC19509 | 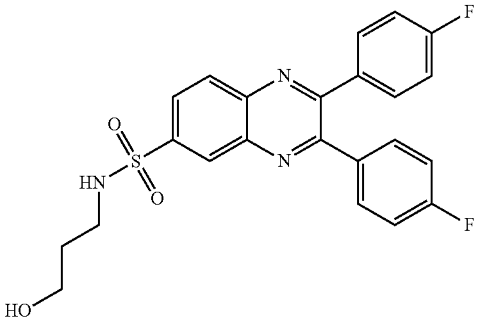 [SMILES: O=S(=O)(NCCCO)c1ccc2nc(-c3ccc(F)cc3)c(-c3ccc(F)cc3)nc2c1] | 66 |
| BC19554 | 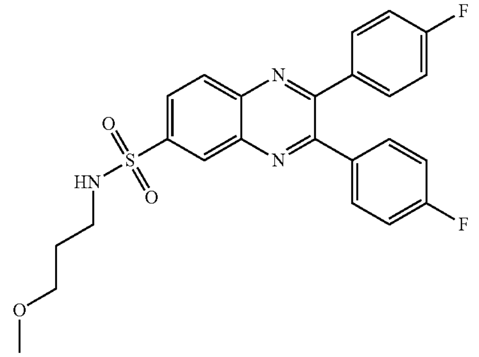 [SMILES: COCCCNS(=O)(=O)c1ccc2nc(-c3ccc(F)cc3)c(-c3ccc(F)cc3)nc2c1] | 52 |
| BC19555 | 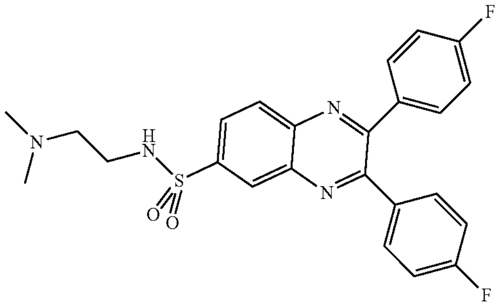 [SMILES: CN(C)CCNS(=O)(=O)c1ccc2nc(-c3ccc(F)cc3)c(-c3ccc(F)cc3)nc2c1] | 1 |
| BC19556 | 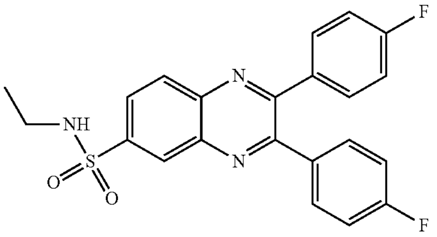 [SMILES: CCNS(=O)(=O)c1ccc2nc(-c3ccc(F)cc3)c(-c3ccc(F)cc3)nc2c1] | 44 |
| BC19557 | 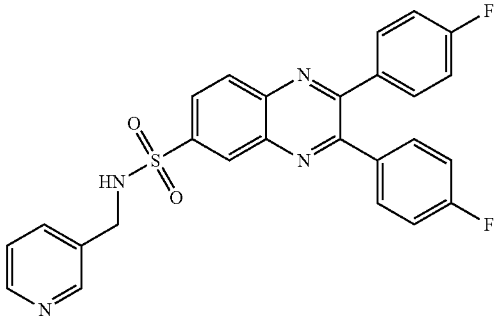 [SMILES: O=S(=O)(NCc1cccnc1)c1ccc2nc(-c3ccc(F)cc3)c(-c3ccc(F)cc3)nc2c1] | 63 |

TABLE 9-continued
| BC No. | Structure | C |
|---|---|---|
| BC19559 | 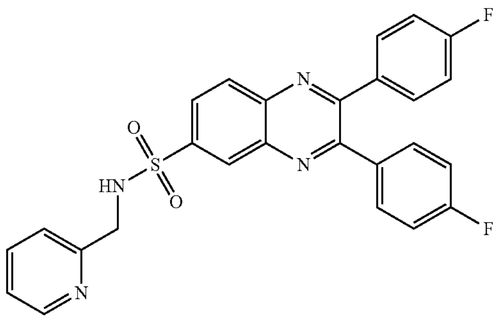 [SMILES: O=S(=O)(NCc1ccccn1)c1ccc2nc(-c3ccc(F)cc3)c(-c3ccc(F)cc3)nc2c1] | 42 |
| BC19560 | 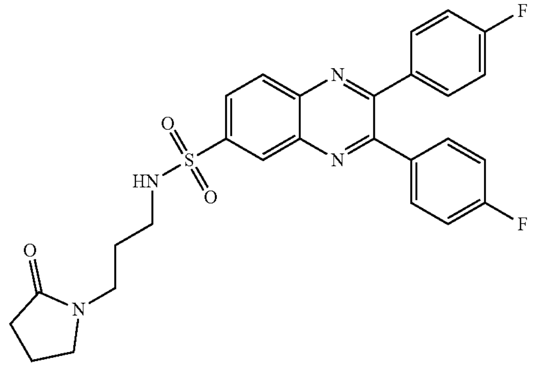 [SMILES: O=C1CCCN1CCCNS(=O)(=O)c1ccc2nc(-c3ccc(F)cc3)c(-c3ccc(F)cc3)nc2c1] | 51 |
| BC19561 | 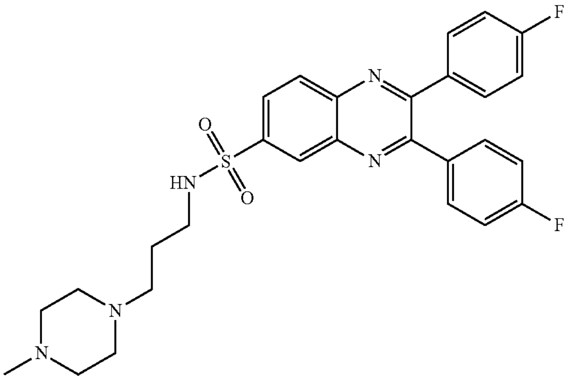 [SMILES: CN1CCN(CCCNS(=O)(=O)c2ccc3nc(-c4ccc(F)cc4)c(-c4ccc(F)cc4)nc3c2)CC1] | 24 |
| BC19562 | 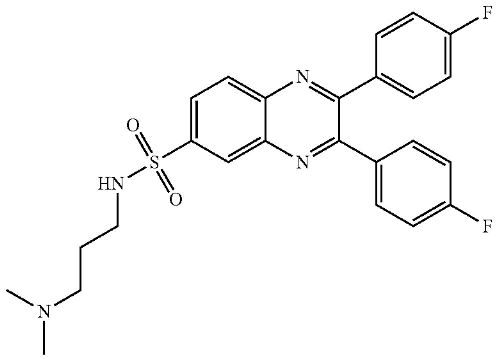 [SMILES: CN(C)CCCNS(=O)(=O)c1ccc2nc(-c3ccc(F)cc3)c(-c3ccc(F)cc3)nc2c1] | 1 |

TABLE 10
| BC No. | Structure | C |
|---|---|---|
| BC19663 | 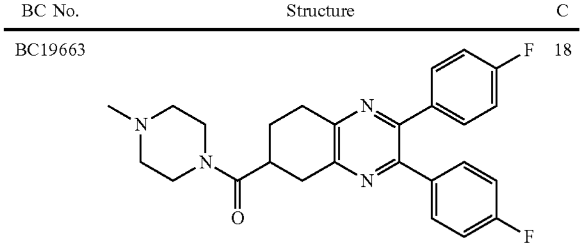 | 18 |
| BC19723 | 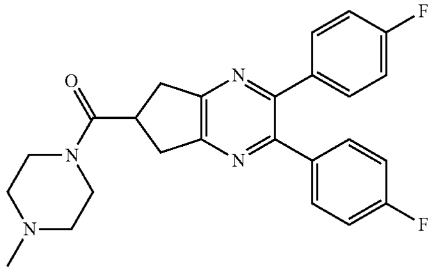 [SMILES: CN1CCN(C(=O)C2Cc3nc(-c4ccc(F)cc4)c(-c4ccc(F)cc4)nc3C2)CC1] | 54 |
TABLE 11
| BCNo. | Structure | A | B |
|---|---|---|---|
| BC20202 | 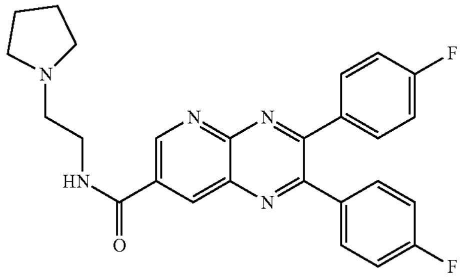 [SMILES: O=C(NCCN1CCCC1)c1cnc2nc(-c3ccc(F)cc3)c(-c3ccc(F)cc3)nc2c1] | + | |
| BC20203 | 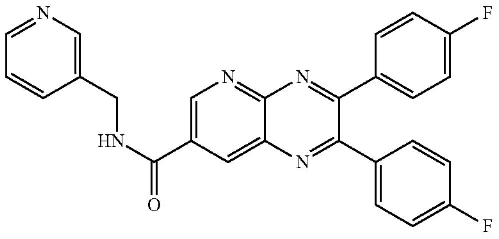 [SMILES: O=C(NCc1cccnc1)c1cnc2nc(-c3ccc(F)cc3)c(-c3ccc(F)cc3)nc2c1] | ++ | |
| BC20204 | 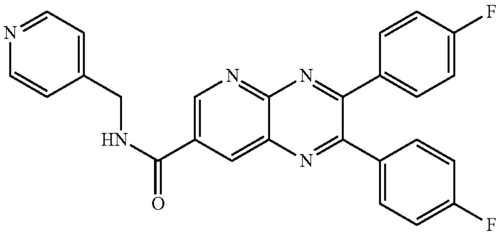 [SMILES: O=C(NCc1ccncc1)c1cnc2nc(-c3ccc(F)cc3)c(-c3ccc(F)cc3)nc2c1] | + | |

TABLE 11-continued
| BCNo. | Structure | A | B |
| --- | --- | --- | --- |
| BC20205 | 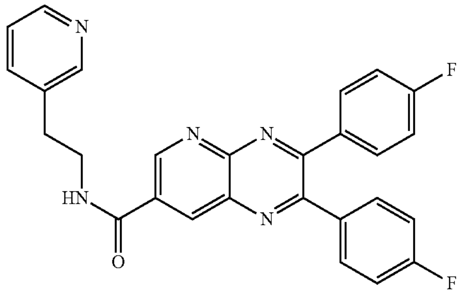 [SMILES: O=C(NCCc1cccnc1)c1cnc2nc(-c3ccc(F)cc3)c(-c3ccc(F)cc3)nc2c1] | +++ | +++ |
| BC20206 | 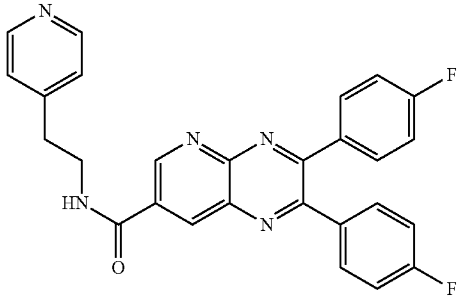 [SMILES: O=C(NCCc1ccncc1)c1cnc2nc(-c3ccc(F)cc3)c(-c3ccc(F)cc3)nc2c1] | +++ | |
TABLE 12
| BCNo. | Structure | A |
| --- | --- | --- |
| BC20208 | 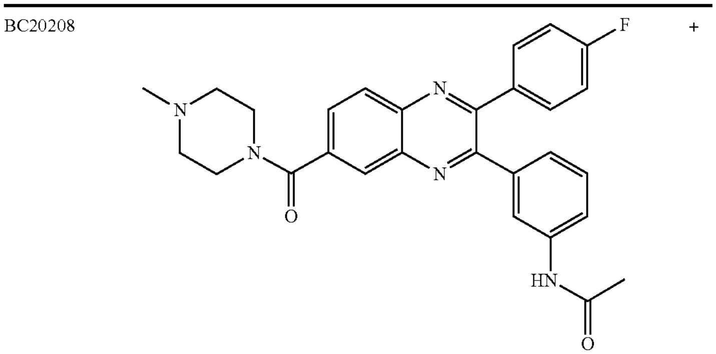 | + |
| BC20209 | 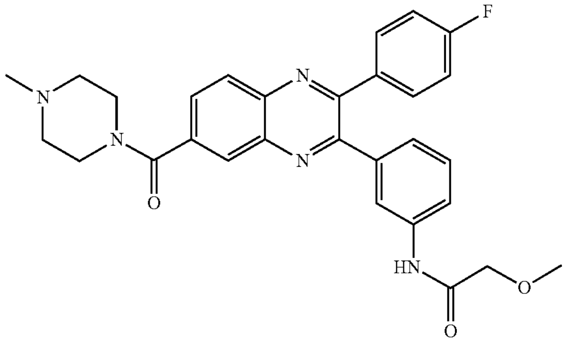 | + |

TABLE 12-continued
| BCNo. | Structure | A |
|---|---|---|
| BC20210 | 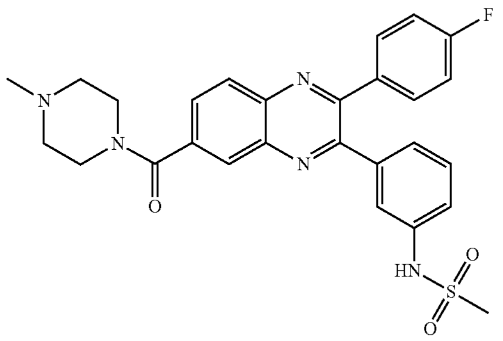 | + |
| BC20211 | 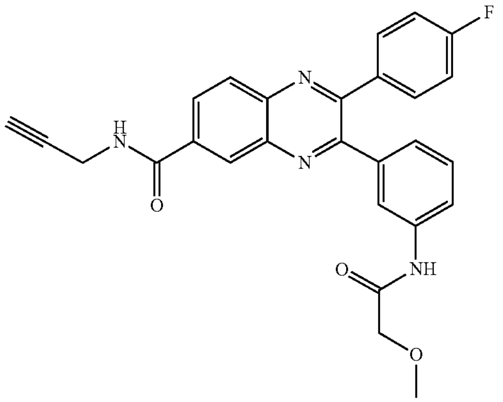 [SMILES: C#CCNC(=O)c1ccc2nc(-c3ccc(F)cc3)c(-c3cccc(NC(=O)COC)c3)nc2c1] | + |
| BC20212 | 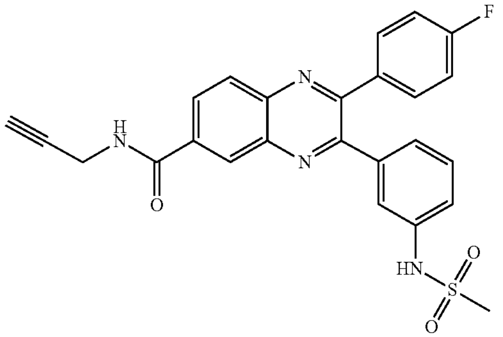 [SMILES: C#CCNC(=O)c1ccc2nc(-c3ccc(F)cc3)c(-c3cccc(NS(C)(=O)=O)c3)nc2c1] | + |
| BC20214 | 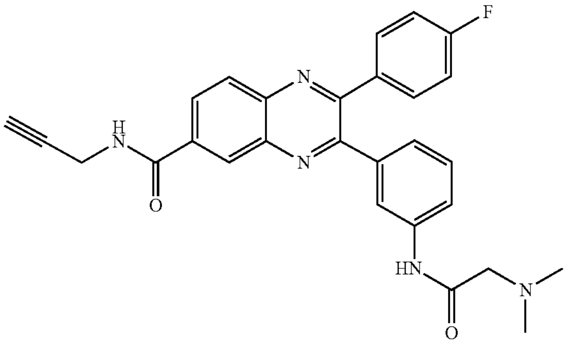 [SMILES: C#CCNC(=O)c1ccc2nc(-c3ccc(F)cc3)c(-c3cccc(NC(=O)CN(C)C)c3)nc2c1] | + |

TABLE 12-continued
| BCNo. | Structure | A |
|---|---|---|
| BC20215 | 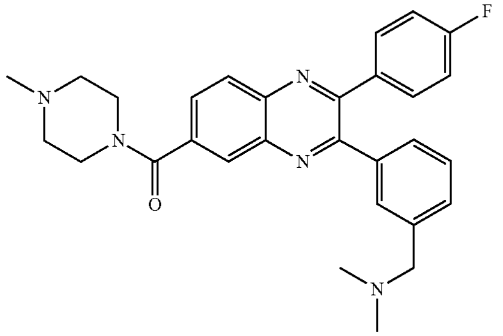 [SMILES: CN(C)Cc1cccc(-c2nc3cc(C(=O)N4CCN(C)CC4)ccc3nc2-c2ccc(F)cc2)c1] | + |
| BC20220 | 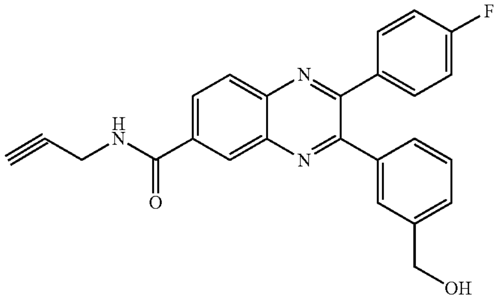 [SMILES: C#CCNC(=O)c1ccc2nc(-c3ccc(F)cc3)c(-c3cccc(CO)c3)nc2c1] | + |
| BC20221 | 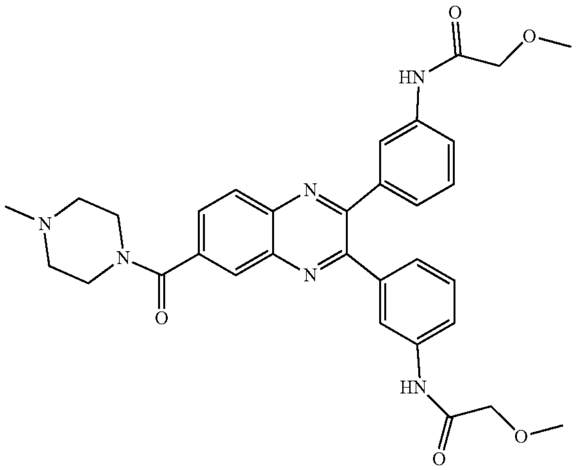 | + |
| BC20222 | 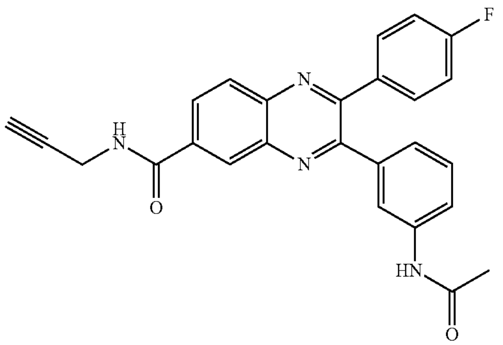 [SMILES: C#CCNC(=O)c1ccc2nc(-c3ccc(F)cc3)c(-c3cccc(NC(C)=O)c3)nc2c1] | + |

TABLE 12-continued
| BCNo. | Structure | A |
|---|---|---|
| BC20223 | 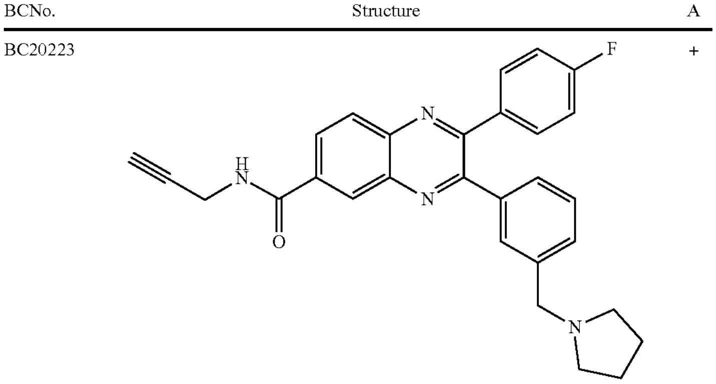 | + |
| BC20227 | 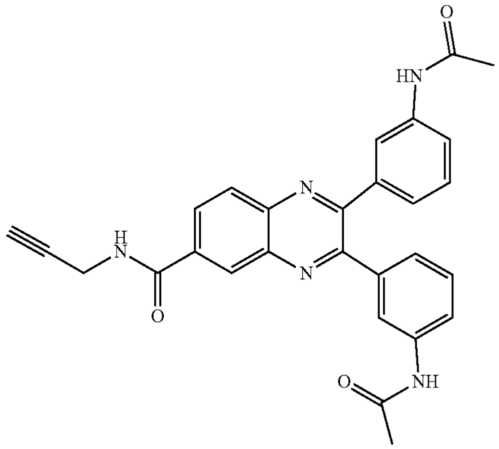 [SMILES: C#CCNC(=O)c1ccc2nc(-c3cccc(NC(C)=O)c3)c(-c3cccc(NC(C)=O)c3)nc2c1] | + |
| BC20228 | 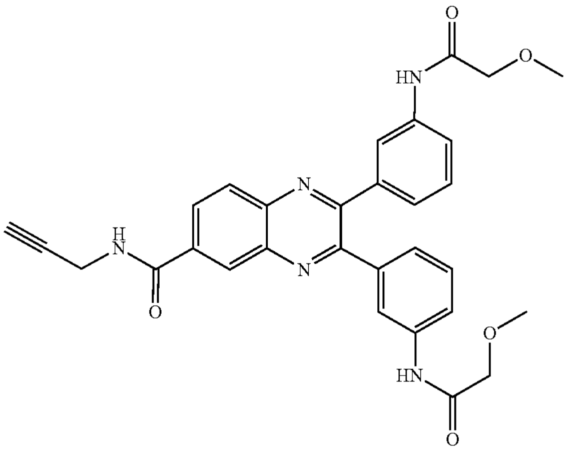 [SMILES: C#CCNC(=O)c1ccc2nc(-c3cccc(NC(=O)COC)c3)c(-c3cccc(NC(=O)COC)c3)nc2c1] | + |
| BC20229 | 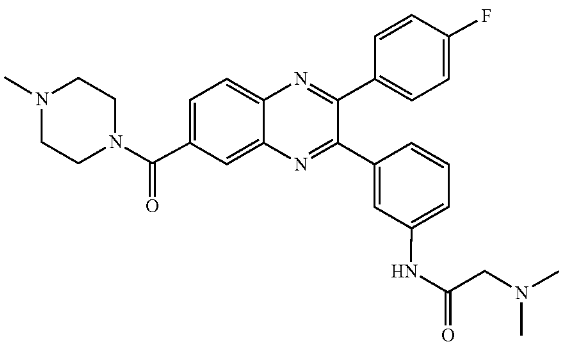 | + |

TABLE 12-continued
| BCNo. | Structure | A |
| --- | --- | --- |
| BC20230 | 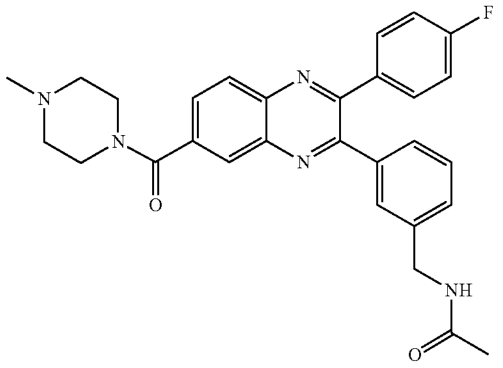 [SMILES: CC(=O)NCc1cccc(-c2nc3cc(C(=O)N4CCN(C)CC4)ccc3nc2-c2ccc(F)cc2)c1] | + |
| BC20231 | 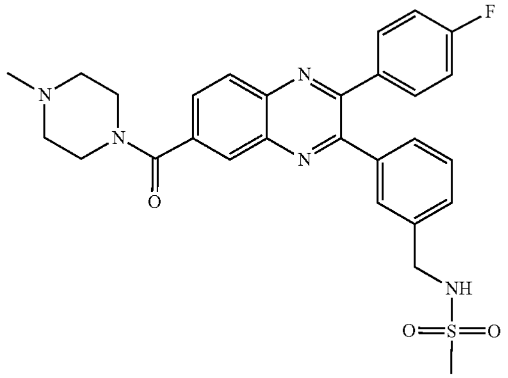 [SMILES: CN1CCN(C(=O)c2ccc3nc(-c4ccc(F)cc4)c(-c4cccc(CNS(C)(=O)=O)c4)nc3c2)CC1] | + |
| BC20232 | 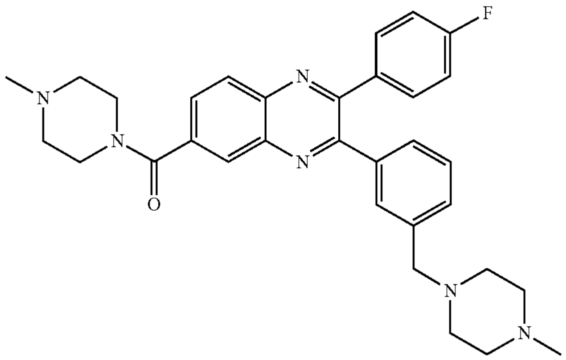 | + |
| BC20233 | 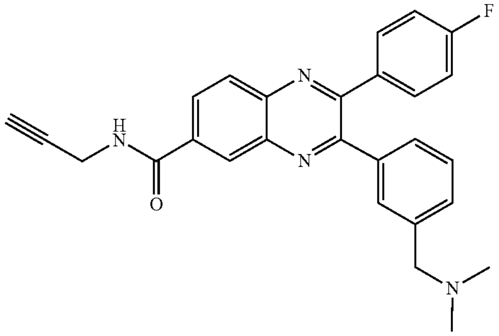 [SMILES: C#CCNC(=O)c1ccc2nc(-c3ccc(F)cc3)c(-c3cccc(CN(C)C)c3)nc2c1] | + |

TABLE 12-continued
| BCNo. | Structure | A |
| --- | --- | --- |
| BC20234 | 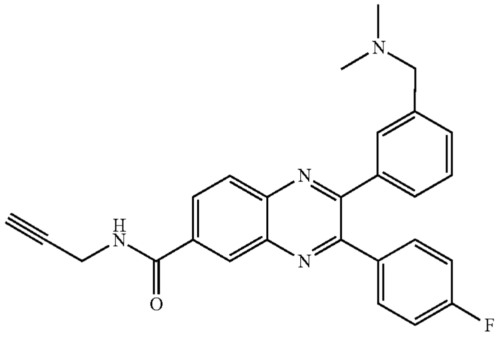 [SMILES: C#CCNC(=O)c1ccc2nc(-c3cccc(CN(C)C)c3)c(-c3ccc(F)cc3)nc2c1] | + |
| BC20240 | 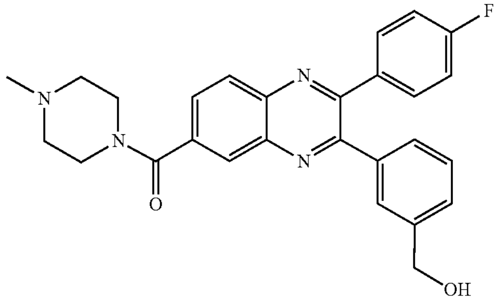 [SMILES: CN1CCN(C(=O)c2ccc3nc(-c4ccc(F)cc4)c(-c4cccc(CO)c4)nc3c2)CC1] | + |
| BC20241 | 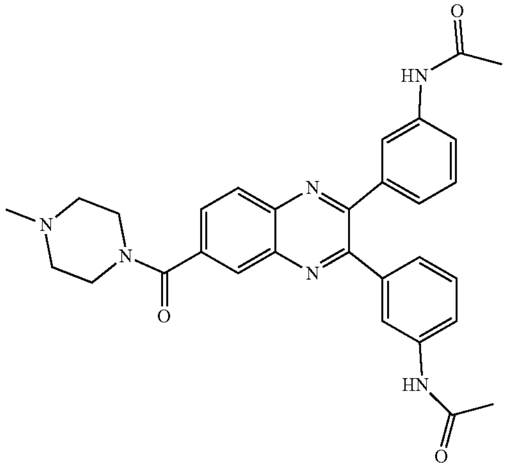 [SMILES: CC(=O)Nc1cccc(-c2nc3ccc(C(=O)N4CCN(C)CC4)cc3nc2-c2cccc(NC(C)=O)c2)c1] | + |
| BC20242 | 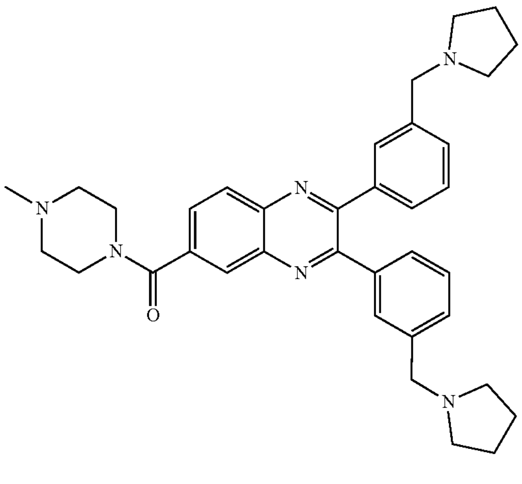 [SMILES: CN1CCN(C(=O)c2ccc3nc(-c4cccc(CN5CCCC5)c4)c(-c4cccc(CN5CCCC5)c4)nc3c2)CC1] | + |

TABLE 12-continued
| BCNo. | Structure | A |
| --- | --- | --- |
| BC20243 | 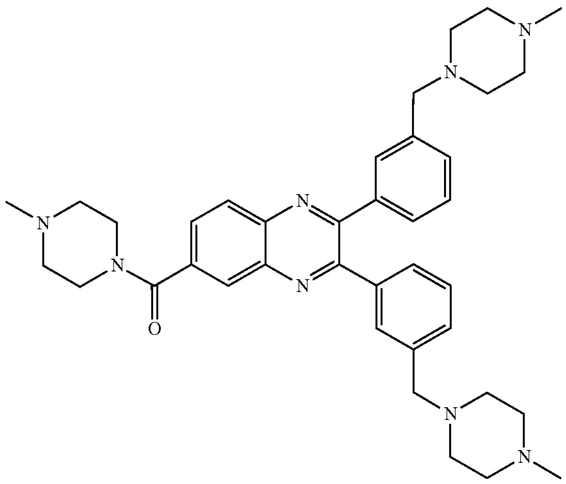 | + |
| BC20244 | 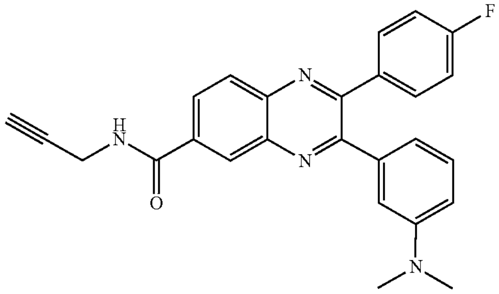 [SMILES: C#CCNC(=O)c1ccc2nc(-c3ccc(F)cc3)c(-c3cccc(N(C)C)c3)nc2c1] | + |
| BC20245 | 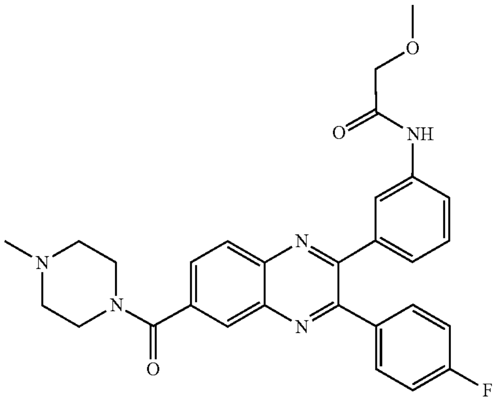 [SMILES: COCC(=O)Nc1cccc(-c2nc3ccc(C(=O)N4CCN(C)CC4)cc3nc2-c2ccc(F)cc2)c1] | + |
| BC20246 | 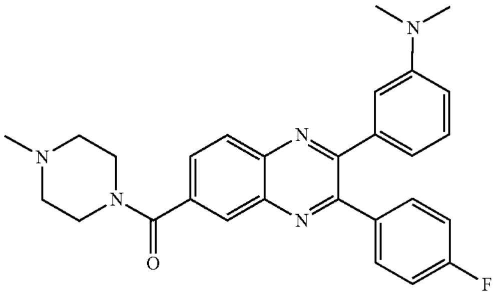 [SMILES: CN1CCN(C(=O)c2ccc3nc(-c4cccc(N(C)C)c4)c(-c4ccc(F)cc4)nc3c2)CC1] | + |

TABLE 12-continued
| BCNo. | Structure | A |
| --- | --- | --- |
| BC20247 | 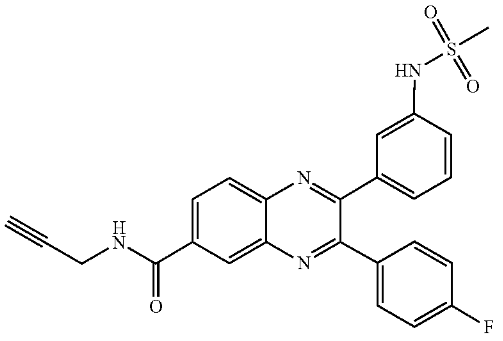 [SMILES: C#CCNC(=O)c1ccc2nc(-c3cccc(NS(C)(=O)=O)c3)c(-c3ccc(F)cc3)nc2c1] | ++ |
| BC20248 | 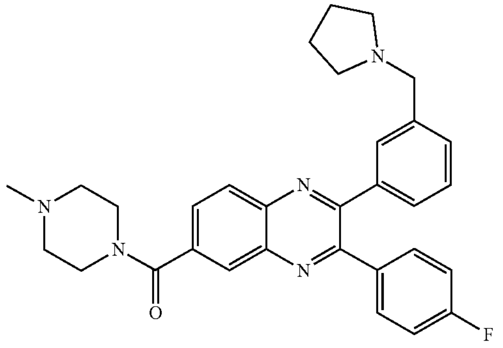 [SMILES: CN1CCN(C(=O)c2ccc3nc(-c4cccc(CN5CCCC5)c4)c(-c4ccc(F)cc4)nc3c2)CC1] | + |
| BC20249 | 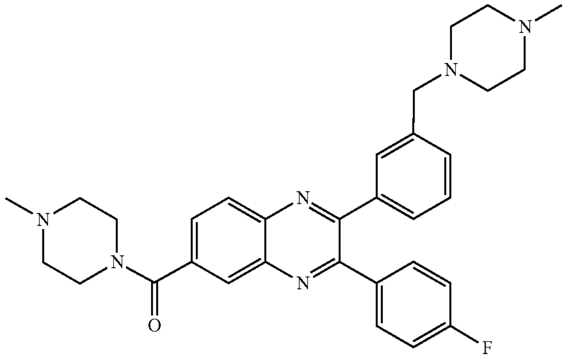 | + |
| BC20258 | 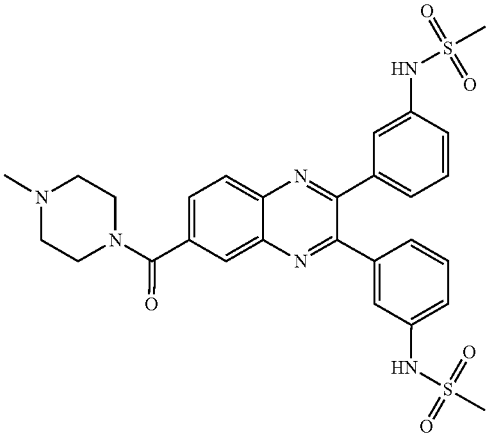 | + |

TABLE 12-continued
| BCNo. | Structure | A |
|---|---|---|
| BC20259 | 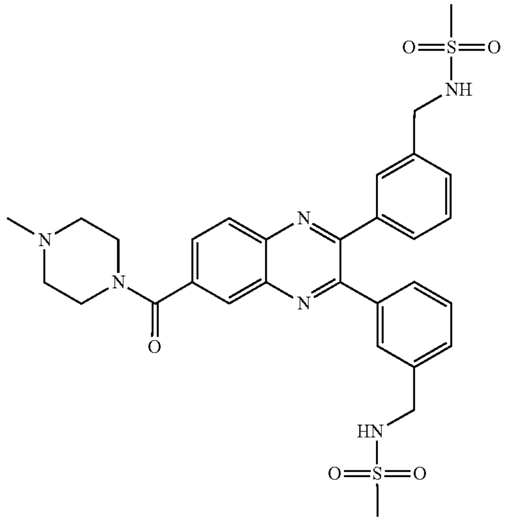 [SMILES: CN1CCN(C(=O)c2ccc3nc(-c4cccc(CNS(C)(=O)=O)c4)c(-c4cccc(CNS(C)(=O)=O)c4)nc3c2)CC1] | + |
| BC20260 | 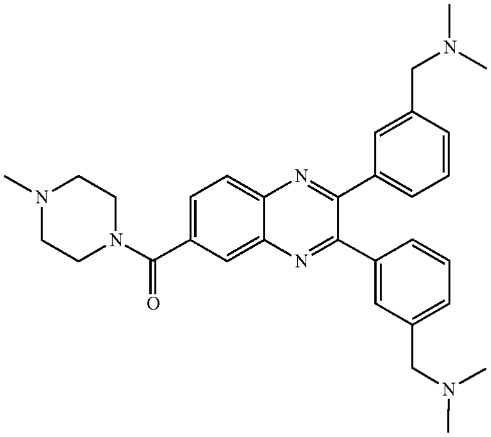 | + |
| BC20261 | 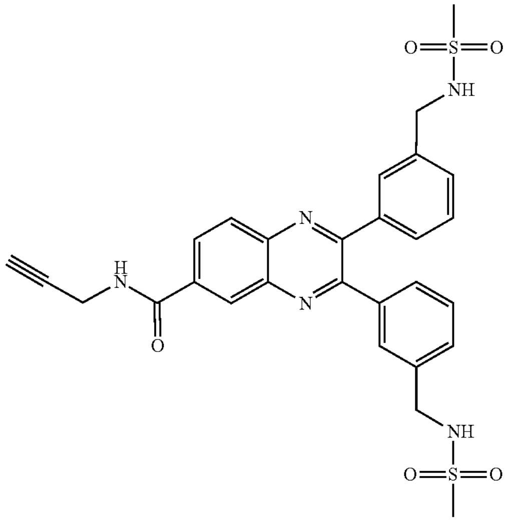 [SMILES: C#CCNC(=O)c1ccc2nc(-c3cccc(CNS(C)(=O)=O)c3)c(-c3cccc(CNS(C)(=O)=O)c3)nc2c1] | + |

TABLE 12-continued
| BCNo. | Structure | A |
|---|---|---|
| BC20262 | 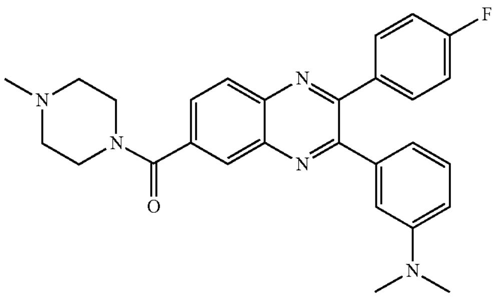 [SMILES: CN1CCN(C(=O)c2ccc3nc(-c4ccc(F)cc4)c(-c4cccc(N(C)C)c4)nc3c2)CC1] | + |
| BC20263 | 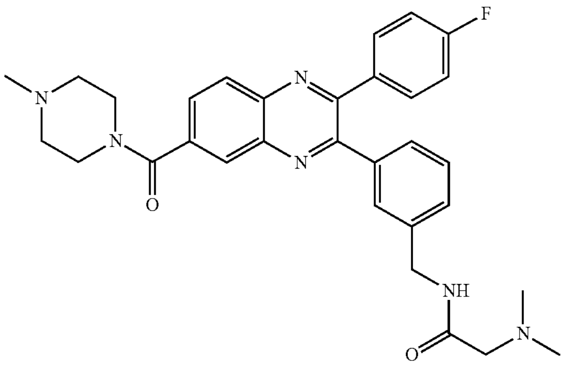 | + |
| BC20264 | 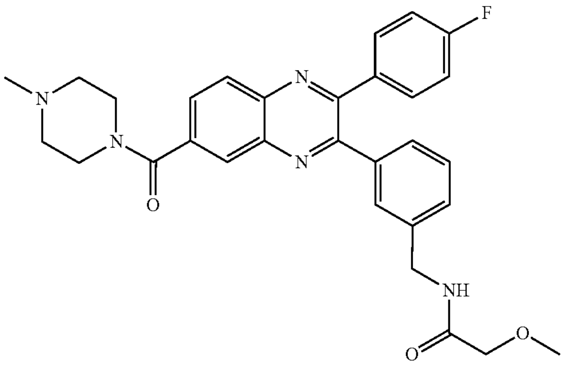 | + |
| BC20265 | 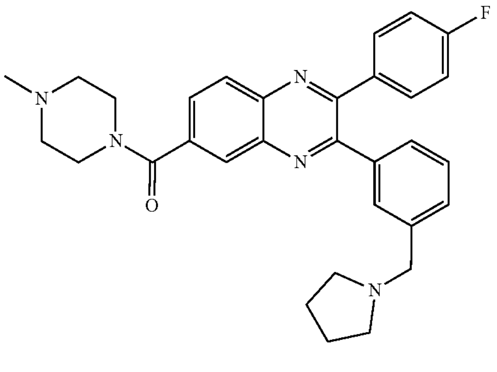 [SMILES: CN1CCN(C(=O)c2ccc3nc(-c4ccc(F)cc4)c(-c4cccc(CN5CCCC5)c4)nc3c2)CC1] | + |

TABLE 12-continued
| BCNo. | Structure | A |
|---|---|---|
| BC20266 | 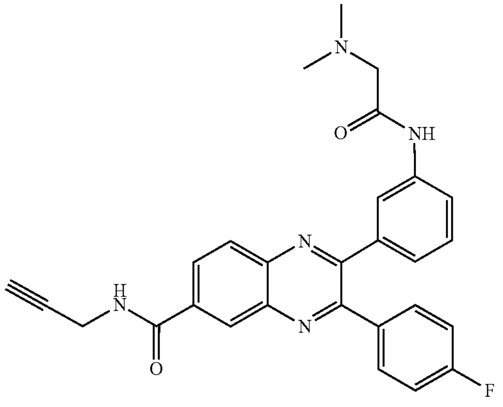 [SMILES: C#CCNC(=O)c1ccc2nc(-c3cccc(NC(=O)CN(C)C)c3)c(-c3ccc(F)cc3)nc2c1] | + |
| BC20272 | 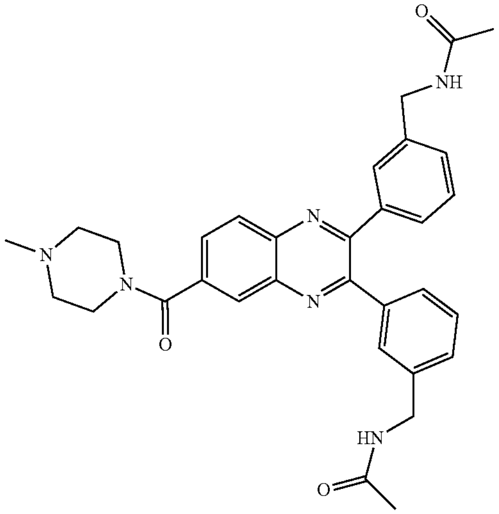 [SMILES: CC(=O)NCc1cccc(-c2nc3ccc(C(=O)N4CCN(C)CC4)cc3nc2-c2cccc(CNC(C)=O)c2)c1] | + |
| BC20273 | 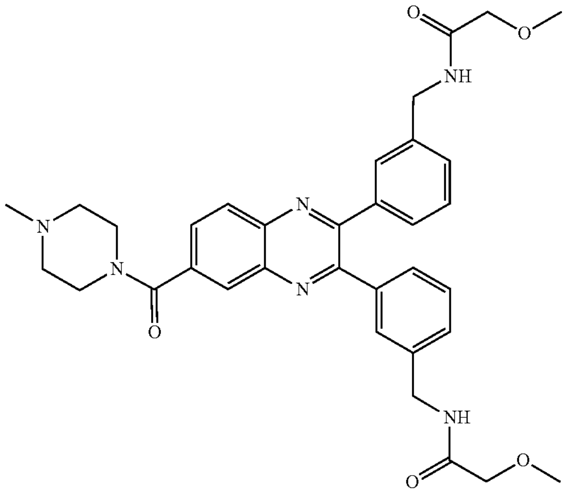 | + |

TABLE 12-continued
| BCNo. | Structure | A |
|---|---|---|
| BC20274 | 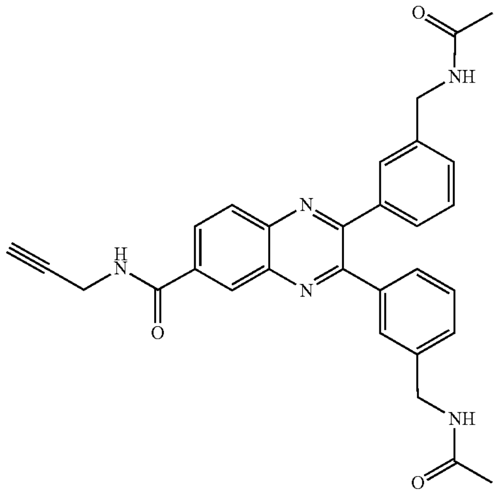 [SMILES: C#CCNC(=O)c1ccc2nc(-c3cccc(CNC(C)=O)c3)c(-c3cccc(CNC(C)=O)c3)nc2c1] | + |
| BC20275 | 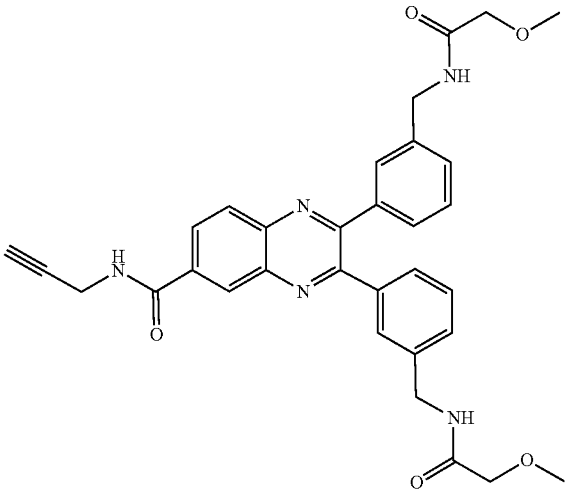 [SMILES: C#CCNC(=O)c1ccc2nc(-c3cccc(CNC(=O)COC)c3)c(-c3cccc(CNC(=O)COC)c3)nc2c1] | + |
| BC20276 | 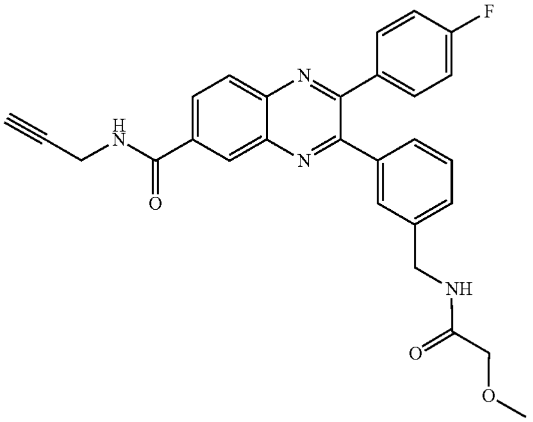 [SMILES: C#CCNC(=O)c1ccc2nc(-c3ccc(F)cc3)c(-c3cccc(CNC(=O)COC)c3)nc2c1] | + |

TABLE 12-continued
| BCNo. | Structure | A |
|---|---|---|
| BC20286 | 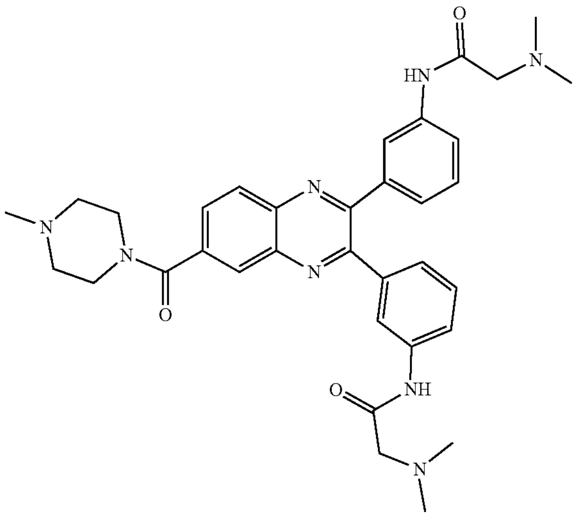 | + |
| BC20288 | 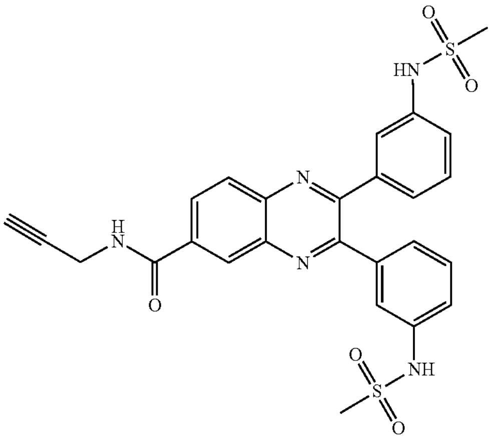 [SMILES: C#CCNC(=O)c1ccc2nc(-c3cccc(NS(C)(=O)=O)c3)c(-c3cccc(NS(C)(=O)=O)c3)nc2c1] | + |
| BC20289 | 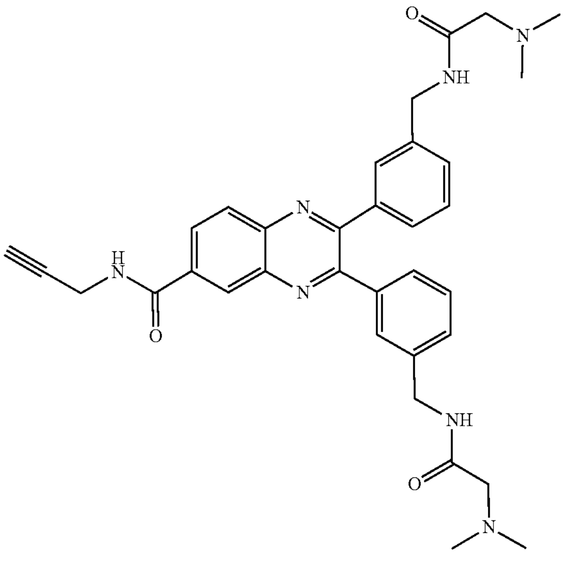 [SMILES: C#CCNC(=O)c1ccc2nc(-c3cccc(CNC(=O)CN(C)C)c3)c(-c3cccc(CNC(=O)CN(C)C)c3)nc2c1] | + |

TABLE 12-continued
| BCNo. | Structure | A |
| --- | --- | --- |
| BC20290 | 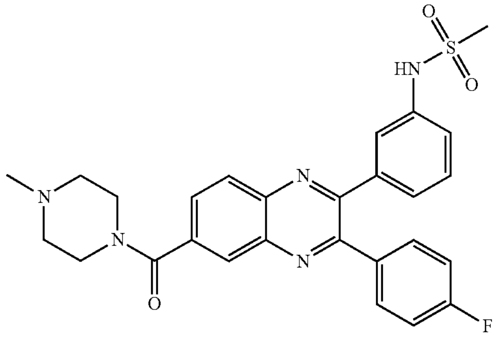 | + |
| BC20296 | 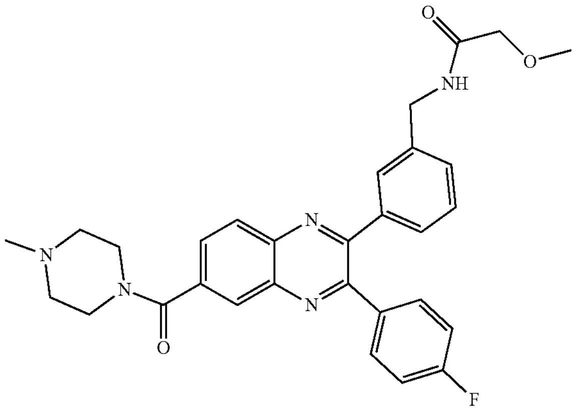 | + |
| BC20306 | 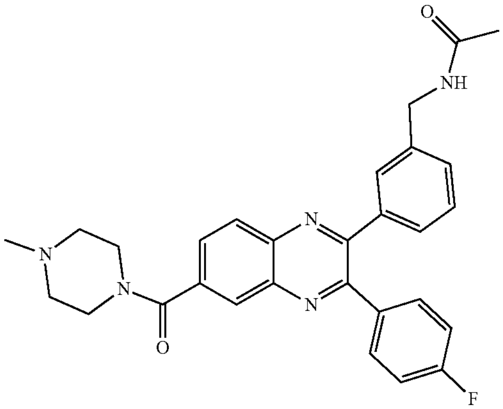 [SMILES: CC(=O)NCc1cccc(-c2nc3ccc(C(=O)N4CCN(C)CC4)cc3nc2-c2ccc(F)cc2)c1] | + |
| BC20307 | 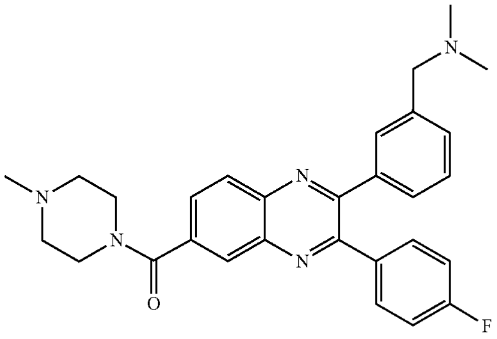 | + |

TABLE 13
| BCNo. | Structure | A | B |
| --- | --- | --- | --- |
| BC20235 | 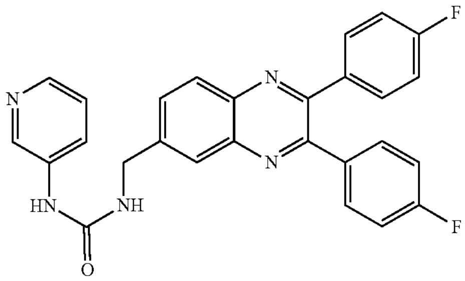 | +++ | +++ |
| BC20236 | 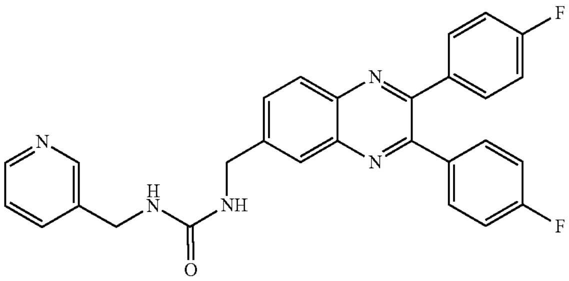 [SMILES: O=C(NCc1cccnc1)NCc1ccc2nc(-c3ccc(F)cc3)c(-c3ccc(F)cc3)nc2c1] | ++ | |
| BC20250 | 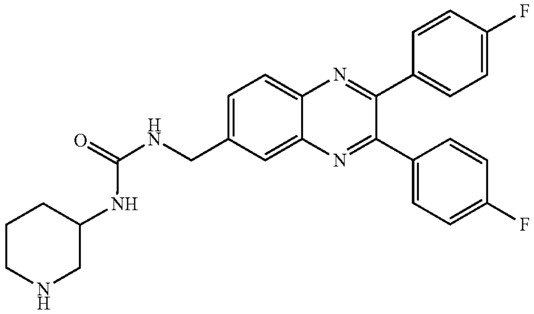 [SMILES: O=C(NCc1ccc2nc(-c3ccc(F)cc3)c(-c3ccc(F)cc3)nc2c1)NC1CCCNC1] | + | |
| BC20251 | 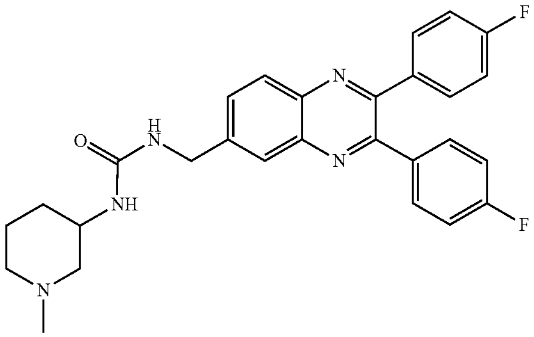 [SMILES: CN1CCCC(NC(=O)NCc2ccc3nc(-c4ccc(F)cc4)c(-c4ccc(F)cc4)nc3c2)C1] | + | |
| BC20252 | 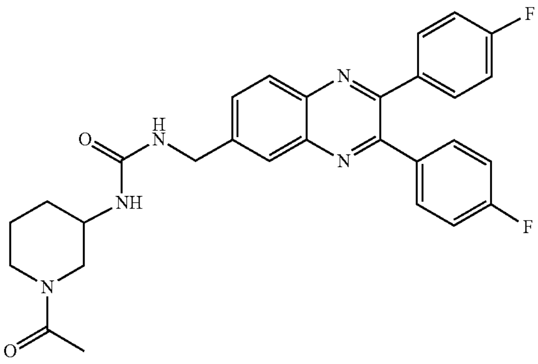 [SMILES: CC(=O)N1CCCC(NC(=O)NCc2ccc3nc(-c4ccc(F)cc4)c(-c4ccc(F)cc4)nc3c2)C1] | + | |

TABLE 13-continued
| BCNo. | Structure | A | B |
|---|---|---|---|
| BC20253 | 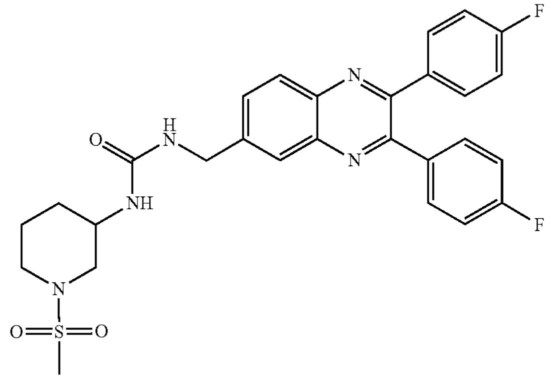 [SMILES: CS(=O)(=O)N1CCCC(NC(=O)NCc2ccc3nc(-c4ccc(F)cc4)c(-c4ccc(F)cc4)nc3c2)C1] | + | |
| BC20267 | 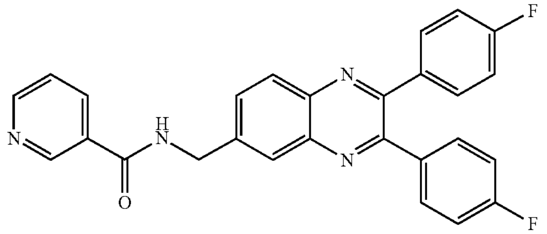 [SMILES: O=C(NCc1ccc2nc(-c3ccc(F)cc3)c(-c3ccc(F)cc3)nc2c1)c1cccnc1] | ++ | |
| BC20278 | 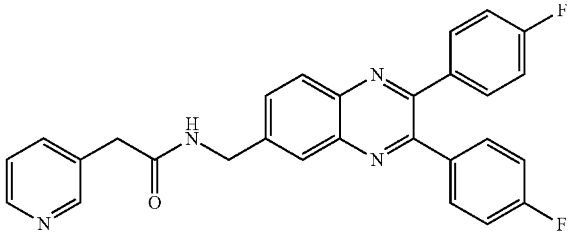 [SMILES: O=C(Cc1cccnc1)NCc1ccc2nc(-c3ccc(F)cc3)c(-c3ccc(F)cc3)nc2c1] | ++ | |
| BC20284 | 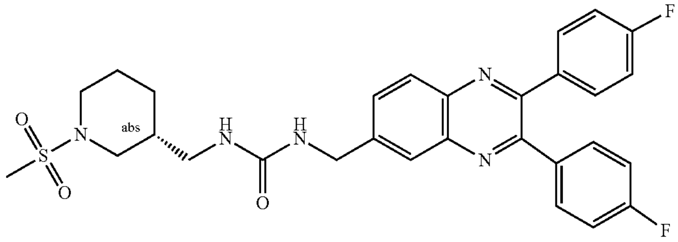 [SMILES: CS(=O)(=O)N1CCC[C@H](CNC(=O)NCc2ccc3nc(-c4ccc(F)cc4)c(-c4ccc(F)cc4)nc3c2)C1] | ++ | |
| BC20285 | 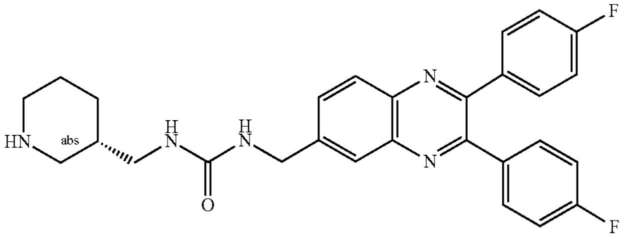 [SMILES: O=C(NCc1ccc2nc(-c3ccc(F)cc3)c(-c3ccc(F)cc3)nc2c1)NC[C@H]1CCCNC1] | ++ | |
| BC20294 | 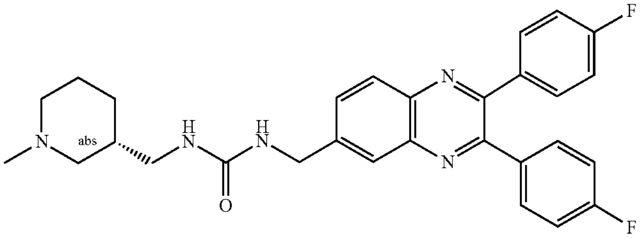 [SMILES: CN1CCC[C@H](CNC(=O)NCc2ccc3nc(-c4ccc(F)cc4)c(-c4ccc(F)cc4)nc3c2)C1] | + | |

TABLE 13-continued
| BCNo. | Structure | A | B |
|---|---|---|---|
| BC20301 | 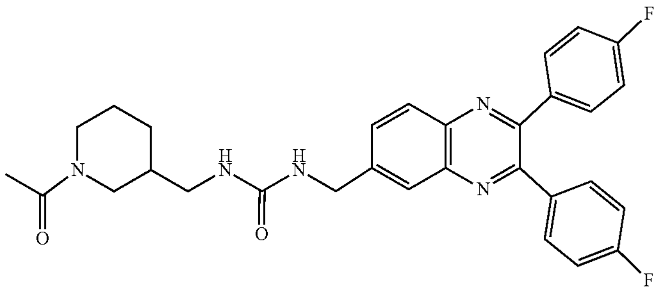 [SMILES: CC(=O)N1CCCC(CNC(=O)NCc2ccc3nc(-c4ccc(F)cc4)c(-c4ccc(F)cc4)nc3c2)C1] | ++ | |
| BC20325 | 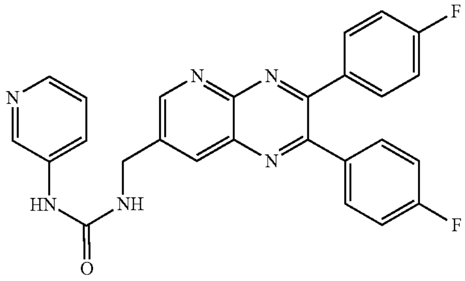 [SMILES: O=C(NCc1cnc2nc(-c3ccc(F)cc3)c(-c3ccc(F)cc3)nc2c1)Nc1cccnc1] | +++ | +++ |
| BC20326 | 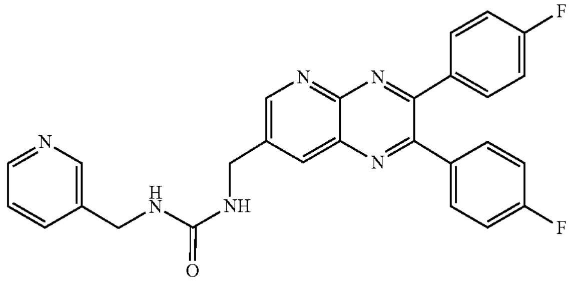 [SMILES: O=C(NCc1cccnc1)NCc1cnc2nc(-c3ccc(F)cc3)c(-c3ccc(F)cc3)nc2c1] | ++ | ++ |
| BC20327 | 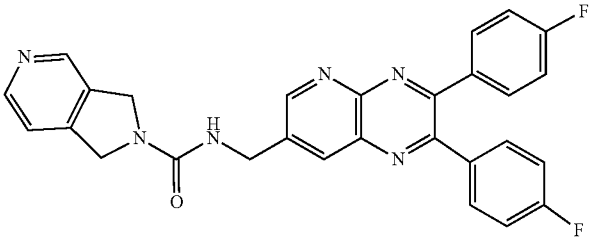 [SMILES: O=C(NCc1cnc2nc(-c3ccc(F)cc3)c(-c3ccc(F)cc3)nc2c1)N1Cc2ccncc2C1] | +++ | +++ |
| BC20328 | 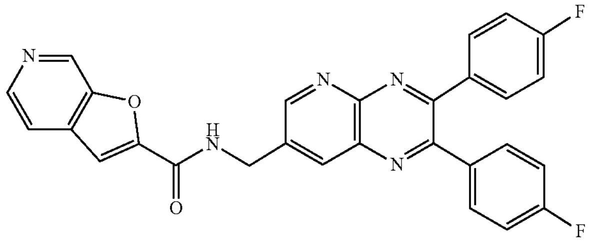 [SMILES: O=C(NCc1cnc2nc(-c3ccc(F)cc3)c(-c3ccc(F)cc3)nc2c1)c1cc2ccncc2o1] | +++ | +++ |

TABLE 13-continued
| BCNo. | Structure | A | B |
|---|---|---|---|
| BC20329 | 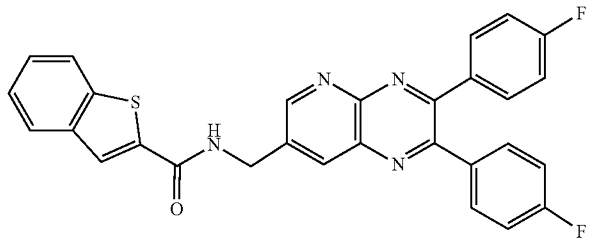 [SMILES: O=C(NCc1cnc2nc(-c3ccc(F)cc3)c(-c3ccc(F)cc3)nc2c1)c1cc2ccccc2s1] | + | ++ |
| BC20332 | 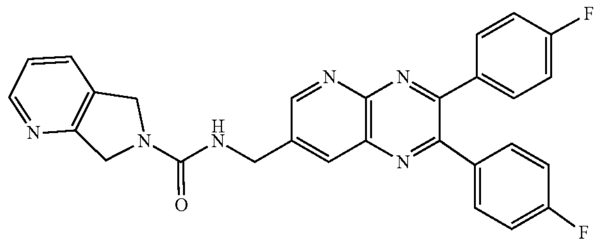 [SMILES: O=C(NCc1cnc2nc(-c3ccc(F)cc3)c(-c3ccc(F)cc3)nc2c1)N1Cc2cccnc2C1] | +++ | +++ |
TABLE 14
| BC No. | Structure | A |
|---|---|---|
| BC20270 | 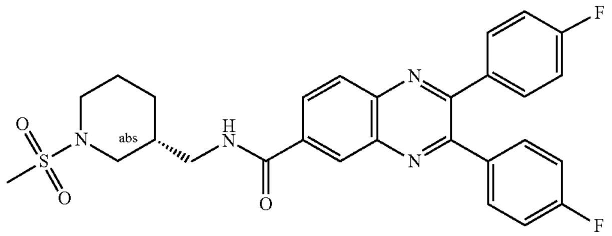 [SMILES: CS(=O)(=O)N1CCC[C@H](CNC(=O)c2ccc3nc(-c4ccc(F)cc4)c(-c4ccc(F)cc4)nc3c2)C1] | + |
| BC20271 | 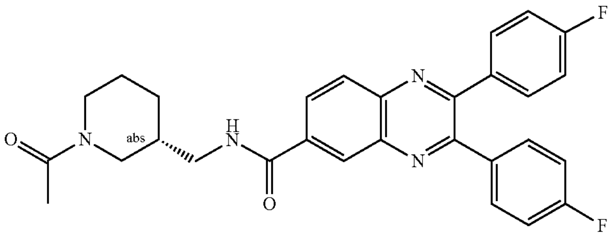 [SMILES: CC(=O)N1CCC[C@H](CNC(=O)c2ccc3nc(-c4ccc(F)cc4)c(-c4ccc(F)cc4)nc3c2)C1] | + |
| BC20279 | 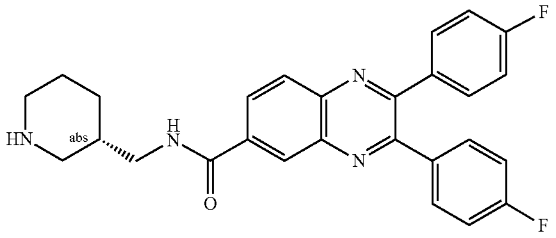 [SMILES: O=C(NC[C@H]1CCCNC1)c1ccc2nc(-c3ccc(F)cc3)c(-c3ccc(F)cc3)nc2c1] | + |
| BC20280 | 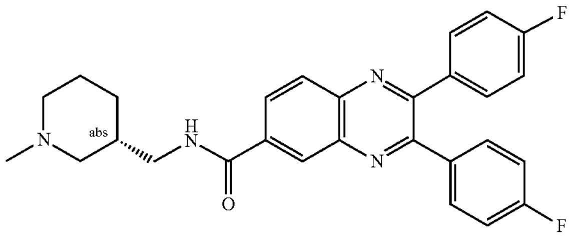 [SMILES: CN1CCC[C@H](CNC(=O)c2ccc3nc(-c4ccc(F)cc4)c(-c4ccc(F)cc4)nc3c2)C1] | ++ |

TABLE 14-continued
| BC No. | Structure | A |
| --- | --- | --- |
| BC20281 | 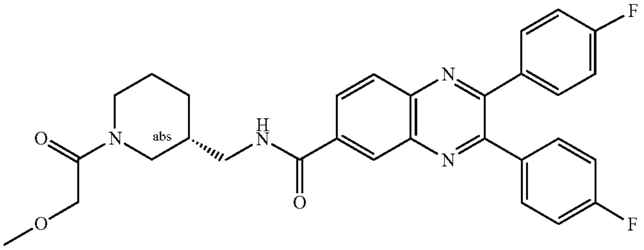 [SMILES: COCC(=O)N1CCC[C@H](CNC(=O)c2ccc3nc(-c4ccc(F)cc4)c(-c4ccc(F)cc4)nc3c2)C1] | + |
| BC20282 | 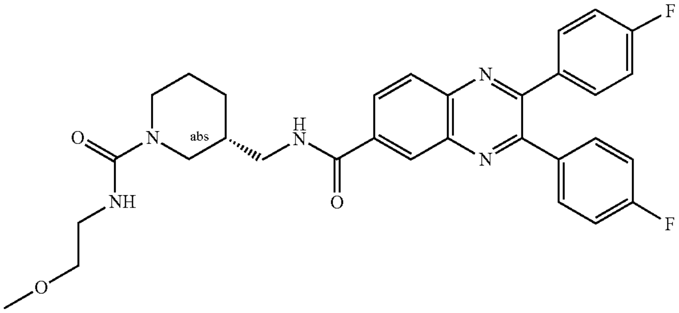 [SMILES: COCCNC(=O)N1CCC[C@H](CNC(=O)c2ccc3nc(-c4ccc(F)cc4)c(-c4ccc(F)cc4)nc3c2)C1] | + |
| BC20283 | 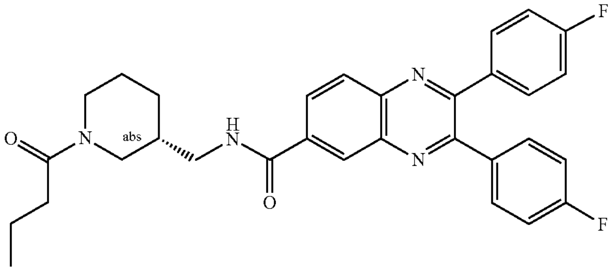 [SMILES: CCCC(=O)N1CCC[C@H](CNC(=O)c2ccc3nc(-c4ccc(F)cc4)c(-c4ccc(F)cc4)nc3c2)C1] | + |
| BC20292 | 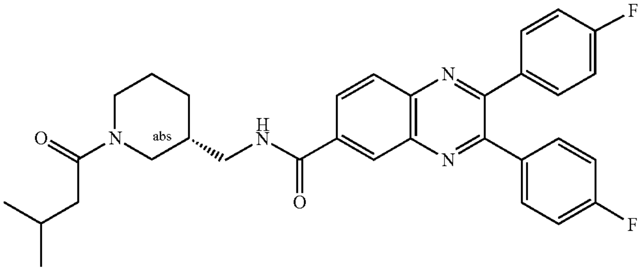 [SMILES: CC(C)CC(=O)N1CCC[C@H](CNC(=O)c2ccc3nc(-c4ccc(F)cc4)c(-c4ccc(F)cc4)nc3c2)C1] | + |
| BC20295 | 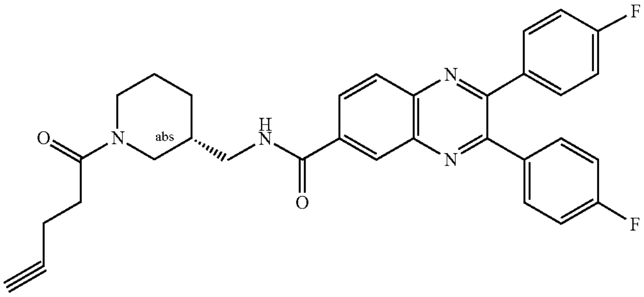 [SMILES: C#CCCC(=O)N1CCC[C@H](CNC(=O)c2ccc3nc(-c4ccc(F)cc4)c(-c4ccc(F)cc4)nc3c2)C1] | + |

TABLE 15a

| BCNo. | Structure | A | B |
|---|---|---|---|
| BC20309 | 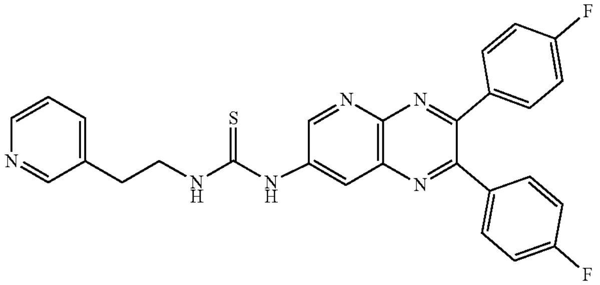 [SMILES: Fc1ccc(-c2nc3cc(NC(=S)NCCc4cccnc4)cnc3nc2-c2ccc(F)cc2)cc1] | +++ | +++ |
| BC20322 | 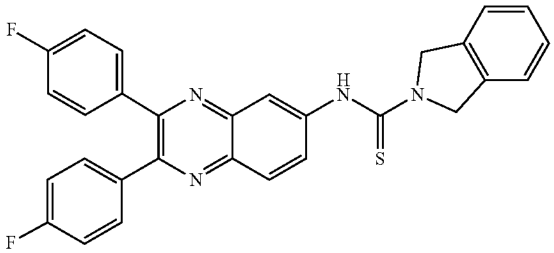 | +++ | +++ |
| BC20323 | 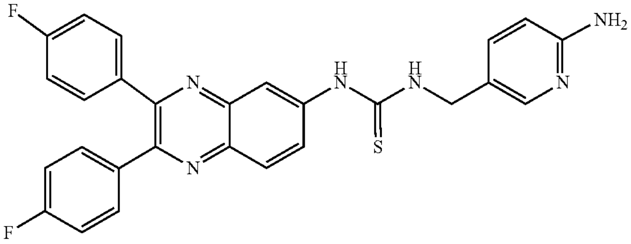 [SMILES: Nc1ccc(CNC(=S)Nc2ccc3nc(-c4ccc(F)cc4)c(-c4ccc(F)cc4)nc3c2)cn1] | +++ | +++ |
| BC20324 | 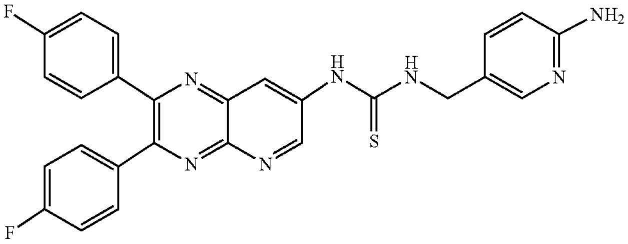 [SMILES: Nc1ccc(CNC(=S)Nc2cnc3nc(-c4ccc(F)cc4)c(-c4ccc(F)cc4)nc3c2)cn1] | +++ | +++ |

TABLE 15b

| BCNo. | Structure | A |
|---|---|---|
| BC20305 | 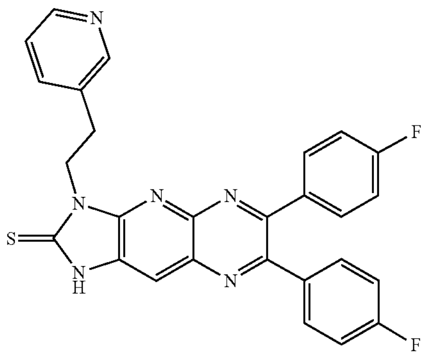 [SMILES: Fc1ccc(-c2nc3cc4[nH]c(=S)n(CCc5cccnc5)c4nc3nc2-c2ccc(F)cc2)cc1] | + |

Numbered Paragraphs

1. A method for inhibiting NAMPT activity within a mammal, wherein said method comprises administering, to said mammal, an effective amount of a compound of Formula (I):

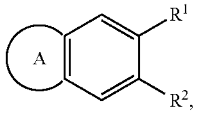

(I)

or a pharmaceutically acceptable salt thereof, wherein: ring A is selected from $C_{3-8}$ cycloalkyl, 4-10 membered heterocycloalkyl, $C_{6-10}$ aryl, and 5-10 membered heteroaryl, each of which is optionally substituted with 1, 2, or 3 substituents independently selected from $R^A$;

each $R^A$ is independently selected from $Cy^1$, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(NR^{e1})NR^{c1}R^{d1}$, $C(NR^{e1})NR^{c1}OR^{a1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}C(S)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$ $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^8$;

each $R^8$ is independently selected from $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, 3, 4, or 5 substituents independently selected from $R^g$;

$R^1$ is selected from $R^9$, $OR^9$, $N(R^N)R^9$, and $S(O)_2R^9$;

$R^2$ is selected from $R^9$, $OR^9$, $N(R^N)R^9$, and $S(O)_2R^9$;

$R^N$ is selected from H, $C_{1-4}$ alkyl, and $C_{1-4}$ haloalkyl;

each $R^9$ is independently selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$ $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{e1}$ is selected from H, $OR^{a1}$ $NR^{c1}R^{d1}$, and $C_{1-4}$ haloalkyl;

each $R^{a1}$, $R^{b1}$, $R^c$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy;

provided that if the compound of Formula (I) has formula (i):

(i)

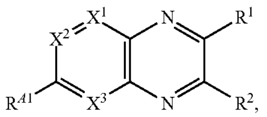

in which $X^1$, $X^2$, and $X^3$ are each independently selected from N, CH, and $CR^A$; and $R^{A1}$ is selected from $C(O)R^{b1}$ and $C(O)NR^{c1}R^{d1}$, then (i) at least one of $X^1$, $X^2$, and $X^3$ is N; or (ii) at least one of $R^1$ and $R^2$ is selected from $C_{1-6}$ haloalkyl and $S(O)_2R^9$.

2. The method of paragraph 1, wherein the compound of Formula (I) has Formula (Ia):

(Ia)

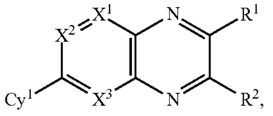

or a pharmaceutically acceptable salt thereof, wherein: $X^1$, $X^2$, and $X^3$ are each independently selected from N, CH, and $CR^A$.

3. The method of paragraph 2, wherein:
$X^1$ is selected from N, CH, and $CR^A$;
$X^2$ is selected from CH and $CR^A$; and
$X^3$ is selected from CH and $CR^A$.

4. The method of paragraph 3, wherein the compound of Formula (Ia) has formula:

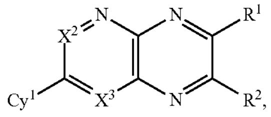

or a pharmaceutically acceptable salt thereof.

5. The method of any one of paragraphs 2-4, wherein each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy.

6. The method of any one of paragraphs 2-4, wherein each $R^A$ is independently selected from halo, $C_{1-6}$ alkyl, and $C_{1-6}$ alkoxy.

7. The method of any one of paragraphs 2-6, wherein $Cy^1$ is $C_{6-10}$ aryl, optionally substituted with 1, 2, or 3 substituents independently selected from $R^{Cy1}$.

8. The method of any one of paragraphs 2-6, wherein $Cy^1$ is $C_{3-10}$cycloalkyl, optionally substituted with 1, 2, or 3 substituents independently selected from $R^{Cy1}$.

9. The method of any one of paragraphs 2-6, wherein $Cy^1$ is 4-10 membered heterocycloalkyl, optionally substituted with 1, 2, or 3 substituents independently selected from $R^{Cy1}$.

10. The method of any one of paragraphs 2-6, wherein $Cy^1$ is 5-10 membered heteroaryl, optionally substituted with 1, 2, or 3 substituents independently selected from $R^{Cy1}$.

11. The method of any one of paragraphs 2-6, wherein $Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$.

12. The method of any one of paragraphs 2-11, wherein each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$.

13. The method of paragraph 12, wherein each $R^8$ is independently selected from $OR^{a1}$ and $NR^{c1}R^{d1}$.

14. The method of any one of paragraphs 2-13, wherein:
$R^1$ is $C_{6-10}$ aryl, optionally substituted with 1, 2, or 3 substituents independently selected from $R^{10}$; and
$R^2$ is $C_{6-10}$ aryl, optionally substituted with 1, 2, or 3 substituents independently selected from $R^{10}$.

15. The method of any one of paragraphs 2-13, wherein:
$R^1$ is $C_{1-6}$ haloalkyl; and
$R^2$ is $C_{6-10}$ aryl, optionally substituted with 1, 2, or 3 substituents independently selected from $R^{10}$.

16. The method of any one of paragraphs 2-13, wherein:
$R^1$ is $C_{6-10}$ aryl, optionally substituted with 1, 2, or 3 substituents independently selected from $R^{10}$; and
$R^2$ is $C_{1-6}$ haloalkyl.

17. The method of any one of paragraphs 2-13, wherein:
$R^1$ is 5-10 membered heteroaryl, optionally substituted with 1, 2, or 3 substituents independently selected from $R^{10}$; and
$R^2$ is $C_{6-10}$ aryl, optionally substituted with 1, 2, or 3 substituents independently selected from $R^{10}$.

18. The method of any one of paragraphs 2-13, wherein:
$R^1$ is $C_{6-10}$ aryl, optionally substituted with 1, 2, or 3 substituents independently selected from $R^{10}$; and
$R^2$ is 5-10 membered heteroaryl, optionally substituted with 1, 2, or 3 substituents independently selected from $R^{10}$.

19. The method of any one of paragraphs 2-18, wherein the 5-10 membered heteroaryl is thiophene.

20. The method of any one of paragraphs 2-18, wherein the $C_{6-10}$ aryl is phenyl.

21. The method of any one of paragraphs 2-20, wherein each $R^{10}$ is independently selected from halo and $S(O)_2R^{b1}$.

22. The method of paragraph 2, wherein:
each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;
$Cy^1$ is 5-10 membered heteroaryl, optionally substituted with 1, 2, or 3 substituents independently selected from $R^{Cy1}$;
each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;
each $R^8$ is independently selected from $OR^{a1}$ and $NR^{c1}R^{d1}$;
$R^1$ is $C_{6-10}$ aryl, optionally substituted with 1, 2, or 3 substituents independently selected from $R^{10}$;
$R^2$ is $C_{6-10}$ aryl, optionally substituted with 1, 2, or 3 substituents independently selected from $R^{10}$; and
each $R^{10}$ is independently selected from halo and $S(O)_2R^{b1}$.

23. The method of paragraph 2, wherein:
each $R^A$ is independently selected from H, halo, $C_{1-6}$ alkyl, and $C_{1-6}$ alkoxy;
$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;
each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;
each $R^8$ is independently selected from $OR^{a1}$ and $NR^{c1}R^{d1}$;

$R^1$ is phenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

24. The method of paragraph 2, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{1-6}$ haloalkyl;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

25. The method of paragraph 2, wherein:

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is trifluoromethyl;

$R^2$ is phenyl, optionally substituted with 1, 2, or 3 substituents independently selected from $R^{10}$; and each $R^{10}$ is independently selected from halo and $S(O)_2R^{b1}$.

26. The method of paragraph 2, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{6-10}$ aryl, optionally substituted with 1, 2, or 3 substituents independently selected from $R^{10}$; and $R^2$ is $C_{1-6}$ haloalkyl;

each $R^{10}$ is independently selected from halo and $S(O)_2R^{b1}$.

27. The method of paragraph 2, wherein:

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is phenyl, optionally substituted with 1, 2, or 3 substituents independently selected from $R^{10}$; and $R^2$ is trifluoromethyl;

each $R^{10}$ is independently selected from halo and $S(O)_2R^{b1}$.

28. The method of paragraph 2, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is 5-10 membered heteroaryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

29. The method of paragraph 2, wherein:

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is thiophenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

30. The method of paragraph 2, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is 5-10 membered heteroaryl, optionally substituted with 1, 2, or 3 substituents independently selected from $R^{10}$; and each $R^{10}$ is independently selected from halo and $S(O)_2R^{b1}$.

31. The method of paragraph 2, wherein:

each $R^A$ is independently selected from halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$;

each $R^8$ is independently selected from $OR^{a1}$ and $NR^{c1}R^{d1}$;

$R^1$ is phenyl, optionally substituted with 1, 2, or 3 substituents independently selected from $R^{10}$;

$R^2$ is thiophenyl, optionally substituted with 1, 2, or 3 substituents independently selected from $R^{10}$; and each $R^{10}$ is independently selected from halo and $S(O)_2R^{b1}$.

32. The method of paragraph 1, wherein the compound of Formula (I) has Formula (Ib):

(Ib)

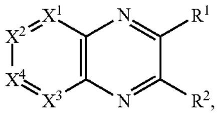

or a pharmaceutically acceptable salt thereof, wherein:

$X^1$, $X^2$, $X^3$, and $X^4$ are each independently selected from N, CH, and $CR^A$;

$R^1$ is selected from $C_{1-6}$ haloalkyl and $S(O)_2R^9$; and $R^2$ is $R^9$.

33. The method of paragraph 32, wherein the compound of Formula (Ib) has formula:

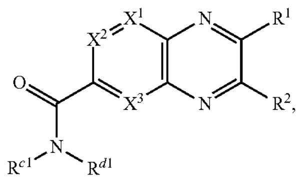

or a pharmaceutically acceptable salt thereof, wherein:

$X^1$ is selected from N, CH, and $CR^A$;

$X^2$ is selected from CH and $CR^A$; and $X^3$ is selected from CH and $CR^A$.

34. The method of paragraph 32, wherein the compound of Formula (Ib) has formula:

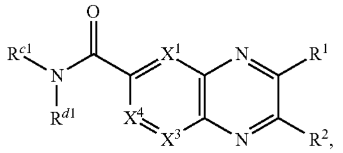

or a pharmaceutically acceptable salt thereof, wherein:

$X^1$ is selected from N, CH, and $CR^A$;

$X^4$ is selected from CH and $CR^A$; and $X^3$ is selected from N, CH and $CR^A$.

35. The method of paragraph 33 or 34, wherein:

$R^1$ is $C_{1-6}$ haloalkyl; and $R^2$ is $C_{6-10}$ aryl, optionally substituted with 1, 2, or 3 independently selected $R^{10}$.

36. The method of paragraph 33 or 34, wherein:

$R^1$ is $C_{1-6}$ haloalkyl; and $R^2$ is 5-10 membered heteroaryl, optionally substituted with 1, 2, or 3 independently selected $R^{10}$.

37. The method of paragraph 32, wherein the compound of Formula (Ib) has formula:

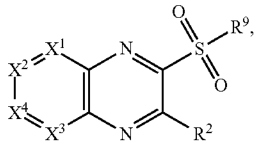

or a pharmaceutically acceptable salt thereof.

38. The method of paragraph 37, wherein the compound has formula:

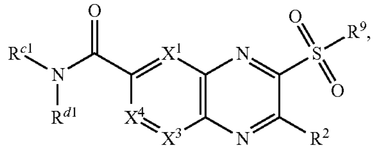

or a pharmaceutically acceptable salt thereof, wherein:

$X^1$ is selected from N, CH, and $CR^A$;

$X^4$ is selected from CH and $CR^A$; and $X^3$ is selected from N, CH and $CR^A$.

39. The method of paragraph 37 or 38, wherein $R^9$ is $C_{6-10}$ aryl, optionally substituted with 1, 2, or 3 independently selected $R^{10}$.

40. The method of paragraph 39, wherein each $R^{10}$ is independently selected from halo and $C_{1-6}$ alkyl.

41. The method of paragraph 33 or 34, wherein:

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$;

or any $R^{c1}$ and $R^{d1}$ together with the N atom to which they are attached form a 4-7 membered heterocycloalkyl, which is optionally substituted with 1 or 2 substituents independently selected from $R^g$;

each $R^9$ is independently selected from $C_{6-10}$ aryl and 5-10 membered heteroaryl, each of which is optionally substituted with 1, 2, or 3 independently selected $R^{10}$;

each $R^{10}$ is independently selected from halo and $C_{1-6}$ alkyl.

42. The method of paragraph 1, wherein the compound of Formula (I) has Formula (Ic):

(Ic)

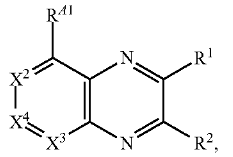

or a pharmaceutically acceptable salt thereof, wherein:

$X^2$, $X^3$, and $X^4$ are each independently selected from N, CH, and $CR^A$; and $R^{A1}$ is selected from $C(O)NR^{c1}R^{d1}$ and $C(O)OR^{a1}$.

43. The method of paragraph 42, wherein:

$X^3$ is selected from N, CH, and $CR^A$;

$X^2$ is selected from CH and $CR^A$; and $X^4$ is selected from CH and $CR^A$.

44. The method of paragraph 42 or 43, wherein each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy.

45. The method of paragraph 44, wherein each $R^A$ is independently selected from halo, $C_{1-6}$ alkyl, and $C_{1-6}$ alkoxy.

46. The method of any one of paragraphs 42-45, wherein $R^{A1}$ is $C(O)OR^{a1}$.

47. The method of any one of paragraphs 42-45, wherein $R^{A1}$ is $C(O)NR^{c1}R^{d1}$.

48. The method of paragraph 47, wherein $R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^9$.

49. The method of paragraph 47, wherein $R^{c1}$ and $R^{d1}$ together with the N atom to which they are attached form a 4-7 membered heterocycloalkyl, which is optionally substituted with 1 or 2 substituents independently selected from $R^9$.

50. The method of any one of paragraphs 42-49, wherein $R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

51. The method of paragraph 50, wherein each $R^{10}$ is independently selected from halo and $C_{1-6}$ alkyl.

52. The method of paragraph 42, wherein:

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$; or $R^{c1}$ and $R^{d1}$ together with the N atom to which they are attached form a 4-7 membered heterocycloalkyl, which is optionally substituted with 1 or 2 substituents independently selected from $R^g$;

$R^1$ and $R^2$ are each independently an $C_{6-10}$ aryl, optionally substituted with 1, 2, or 3 independently selected $R^{10}$; and each $R^{10}$ is independently selected from halo and $C_{1-6}$ alkyl.

53. A method of paragraph 1, wherein the compound of Formula (I) has Formula (Id):

(Id)

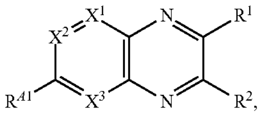

or a pharmaceutically acceptable salt thereof, wherein:

$X^1$, $X^2$, and $X^3$ are each independently selected from N, CH, and $CR^A$; and $R^{A1}$ is selected from $NR^{c1}R^{d1}$, $NR^{c1}C(O)R^{b1}$, $NR^{c1}C(O)OR^{a1}$, and $NR^{c1}C(O)NR^{c1}R^{d1}$.

54. The method of paragraph 53, wherein $X^1$ is selected from N, CH, and $CR^A$;

$X^3$ is selected from N, CH, and $CR^A$; and $X^2$ is selected from CH and $CR^A$.

55. The method of paragraph 53, wherein each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

56. The method of paragraph 55, wherein each $R^A$ is independently selected from H, halo, $C_{1-6}$ alkyl, and $C_{1-6}$ alkoxy.

57. The method of paragraph 53, wherein $R^{A1}$ is $NR^{c1}C(O)OR^{a1}$.

58. The method of paragraph 57, wherein $R^{a1}$ is selected from $C_{1-6}$ alkyl, $C_{1-4}$ haloalkyl, $C_{2-6}$ alkenyl, and $C_{2-6}$ alkynyl, each of which is optionally substituted with 1 or 2 $R^g$.

59. The method of paragraph 53, wherein $R^{A1}$ is $NR^{c1}C(O)R^b$.

60. The method of paragraph 59, wherein $R^{b1}$ is selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1 or 2 $R^g$.

61. The method of paragraph 53, wherein $R^{A1}$ is selected from $NR^{c1}R^{d1}$ and $NR^{c1}C(O)NR^{c1}R^{d1}$ 62. The method of paragraph 61, wherein each $R^{c1}$ and $R^{d1}$ is independently selected from H, $C_{1-6}$ alkyl, $C_{2-6}$ alkynyl, $C_{3-10}$ cycloalkyl, 4-10 membered heterocycloalkyl, 5-10 membered heteroaryl, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1 or 2 independently selected $R^g$.

63. The method of paragraph 61, wherein $R^{c1}$ and $R^{d1}$ together with the N atom to which they are attached form a 4-7 membered heterocycloalkyl, which is optionally substituted with 1 or 2 substituents independently selected from $R^g$.

64. The method of any one of paragraphs 53-63, wherein $R^1$ and $R^2$ are each independently an $C_{6-10}$ aryl, optionally substituted with 1, 2, or 3 independently selected $R^{10}$.
65. The method of paragraph 64, wherein each $R^{10}$ is independently selected from halo and $C_{1-6}$ alkyl.
66. The method of paragraph 53, wherein:
    each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;
    $R^{a1}$ is selected from $C_{1-6}$ alkyl, $C_{1-4}$ haloalkyl, $C_{2-6}$ alkenyl, and $C_{2-6}$ alkynyl, each of which is optionally substituted with 1 or 2 $R^g$;
    $R^{b1}$ is selected from $C_{1-6}$ alkyl, $C_{1-4}$ haloalkyl, $C_{2-6}$ alkenyl, $C_{2-6}$ alkynyl, and 4-membered heterocycloalkyl, each of which is optionally substituted with 1 or 2 $R^g$;
    each $R^{c1}$ and $R^{d1}$ is independently selected from H, $C_{1-6}$ alkyl, $C_{2-6}$ alkynyl, $C_{3-10}$ cycloalkyl, 4-10 membered heterocycloalkyl, 5-10 membered heteroaryl, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1 or 2 independently selected $R^g$; or
    $R^{c1}$ and $R^{d1}$ together with the N atom to which they are attached form a 4-7 membered heterocycloalkyl, which is optionally substituted with 1 or 2 substituents independently selected from $R^g$;
    $R^1$ and $R^2$ are each independently an $C_{6-10}$ aryl, optionally substituted with 1, 2, or 3 independently selected $R^{10}$; and
    each $R^{10}$ is independently selected from halo and $C_{1-6}$ alkyl.
67. The method of paragraph 1, wherein the compound of Formula (I) has Formula (Ie):

(Ie)

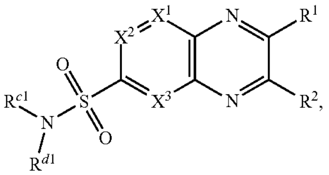

or a pharmaceutically acceptable salt thereof, wherein $X^1$, $X^2$, and $X^3$ are each independently selected from N, CH, and $CR^A$.

68. The method of paragraph 67, wherein:
    $X^1$ is selected from N, CH, and $CR^A$;
    $X^3$ is selected from N, CH, and $CR^A$; and
    $X^2$ is selected from CH and $CR^A$.
69. The method of paragraph 67, wherein each $R^A$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.
70. The method of paragraph 67, wherein $R^{c1}$ and $R^{d1}$ are each independently selected from $C_{1-6}$ alkyl, $C_{3-10}$ cycloalkyl, (4-10 membered heterocycloalkyl)-$C_{1-4}$ alkylene, and (5-10 membered heteroaryl)-$C_{1-4}$ alkylene, each of which is optionally substituted with 1 or 2 $R^g$.
71. The method of paragraph 67, wherein $R^1$ and $R^2$ are each independently an $C_{6-10}$ aryl, optionally substituted with 1 or 2 independently selected $R^{10}$.
72. The method of paragraph 71, wherein each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.
73. The method of paragraph 67, wherein:
    each $R^A$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;
    $R^{c1}$ and $R^{d1}$ are each independently selected from $C_{1-6}$ alkyl, $C_{3-10}$ cycloalkyl, (4-10 membered heterocycloalkyl)-$C_{1-4}$ alkylene, and (5-10 membered heteroaryl)-$C_{1-4}$ alkylene, each of which is optionally substituted with 1 or 2 $R^g$;
    $R^1$ and $R^2$ are each independently an $C_{6-10}$ aryl, optionally substituted with 1 or 2 independently selected $R^{10}$; and
    each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.
74. The method of paragraph 1, wherein ring A is $C_{3-8}$ cycloalkyl.
75. The method of paragraph 74, wherein the compound of Formula (I) has Formula (If):

(If)

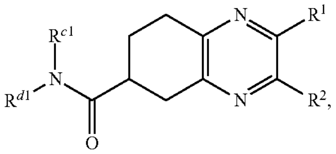

or a pharmaceutically acceptable salt thereof.

76. The method of paragraph 74, wherein the compound of Formula (I) has Formula (Ig):

(Ig)

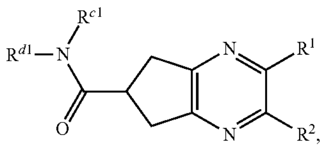

or a pharmaceutically acceptable salt thereof.

77. The method of paragraph 75 or 76, wherein:
    $R^{c1}$ and $R^{d1}$ together with the N atom to which they are attached form a 4-7 membered heterocycloalkyl, which is optionally substituted with 1, 2, or 3 substituents independently selected from $R^g$;
    $R^1$ and $R^2$ are each independently an $C_{6-10}$ aryl, optionally substituted with 1, 2, or 3 substituents independently selected from $R^{10}$; and
    each $R^{10}$ is independently a halo.
78. The method of paragraph 1, wherein the compound of Formula (I) is selected from any one of the compounds listed in Table 2a, Table 3, Table 4, Table 5, Table 6, Table 7, Table 8, Table 9, Table 10, Table 11, Table 12, Table 13, Table 14, and Table 15a, or a pharmaceutically acceptable salt thereof.

79. A method for inhibiting NAMPT activity within a mammal, wherein said method comprises administering, to said mammal, an effective amount of a compound listed in Table 1 and Table 2b, or a pharmaceutically acceptable salt thereof.

80. A compound selected from any one of the compounds listed in Table 8, or a pharmaceutically acceptable salt thereof.

81. A pharmaceutical composition comprising a compound of paragraph 80, or a pharmaceutically acceptable salt thereof, and a pharmaceutically acceptable carrier.

82. A compound of Formula (II):

(II)

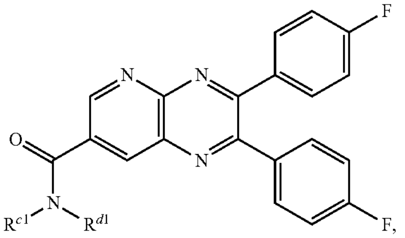

or a pharmaceutically acceptable salt thereof, wherein:

$R^{c1}$ and $R^{d1}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

83. The compound of paragraph 82, wherein the compound of Formula (II) is not:

(BC19408)

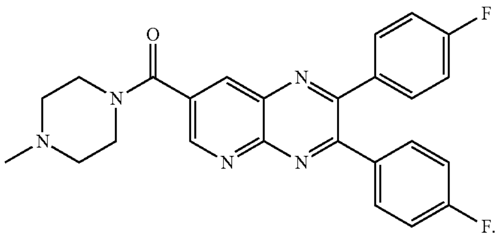

84. The compound of paragraph 82, wherein each $R^{c1}$ and $R^{d1}$ is independently selected from H, $C_{1-6}$ alkyl, alkenyl, $C_{2-6}$ alkynyl, (5-10 membered heteroaryl)-$C_{1-4}$ alkylene, and (4-10 membered heterocycloalkyl)-$C_{1-4}$ alkylene, each of which is optionally substituted with 1 or 2 $R^9$.

85. The compound of paragraph 82, wherein each $R^9$ is independently selected from $C_{1-6}$ alkoxy, OH, amino, $C_{1-6}$ alkylamino, and di($C_{1-6}$ alkyl)amino.

86. The compound of paragraph 82, selected from any one of the compounds listed in Table 11, or a pharmaceutically acceptable salt thereof.

87. A pharmaceutical composition comprising a compound of paragraph 82, or a pharmaceutically acceptable salt thereof, and a pharmaceutically acceptable carrier.

88. A method for inhibiting NAMPT activity within a mammal, wherein said method comprises administering, to said mammal, an effective amount of a compound of paragraph 82, or a pharmaceutically acceptable salt thereof.

89. A compound of Formula (III):

(III)

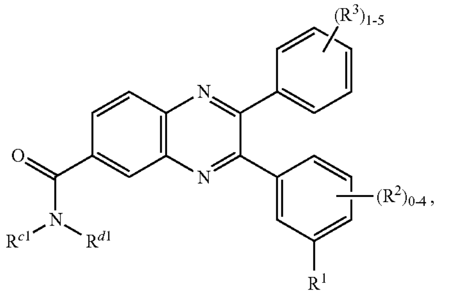

or a pharmaceutically acceptable salt thereof, wherein:

$R^1$ is selected from $C_{1-6}$ alkyl, $NR^{c1}R^{d1}$, $NR^{c1}C(O)R^{b1}$, and $NR^{c1}S(O)_2R^{b1}$, wherein said $C_{1-6}$ alkyl is substituted with a substituent selected from $OR^{a1}$, $NR^{c1}R^{d1}$, $NR^{c1}C(O)R^{b1}$, and $NR^{c1}S(O)_2R^{b1}$;

$R^2$ and $R^3$ are each independently selected from halo, CN, $NO_2$, $C_{1-6}$ alkyl, $C_{1-6}$ haloalkyl, $C(O)NR^{c1}R^{d1}$, $C(O)OR^{a1}$, $NR^{c1}R^{d1}$, $NR^{c1}C(O)R^{b1}$, $NR^{c1}C(O)$ $OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with a substituent selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy, provided that if $R^1$ is $NR^{c1}R^{d1}$ then at least one $R^3$ is selected from halo, CN, $NO_2$, $C_{1-6}$ alkyl, $C_{1-6}$ haloalkyl, $C(O)NR^{c1}R^{d1}$, $C(O)OR^{a1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with a substituent selected from halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

90. The compound of paragraph 89, wherein $R^3$ is selected from halo, $C_{1-6}$ alkyl, $NR^{c1}R^{d1}$, $NR^{c1}C(O)R^{b1}$, and $NR^{c1}S(O)_2R^{b1}$, wherein said $C_{1-6}$ alkyl is substituted with a substituent selected from $OR^{a1}$, $NR^{c1}R^{d1}$, $NR^{c1}C(O)R^{b1}$, and $NR^{c1}S(O)_2R^{b1}$ 91. The compound of paragraph 89, wherein $R^{a1}$, $R^{b1}$, $R^c$, and $R^{d1}$ is each independently selected from H, $C_{1-6}$ alkyl, and $C_{2-6}$ alkynyl, each of which is optionally substituted with 1 or 2 $R^9$.

92. The compound of paragraph 89, wherein $R^{c1}$ and $R^{d1}$ together with the N atom to which they are attached form a 4-7 membered heterocycloalkyl, which is optionally substituted with 1 or 2 substituents independently selected from $R^9$.

93. The compound of paragraph 89, wherein each $R^9$ is independently selected from $C_{1-6}$ alkyl, OH, $C_{1-6}$ alkoxy, amino, $C_{1-6}$ alkylamino, and di($C_{1-6}$ alkyl)amino.

94. The compound of paragraph 89, wherein the compound of Formula (III) is selected from any one of the compounds listed in Table 12, or a pharmaceutically acceptable salt thereof.

95. A pharmaceutical composition comprising a compound of paragraph 89, or a pharmaceutically acceptable salt thereof, and a pharmaceutically acceptable carrier.

96. A method for inhibiting NAMPT activity within a mammal, wherein said method comprises administering, to said mammal, an effective amount of a compound of paragraph 89, or a pharmaceutically acceptable salt thereof.

97. A compound of Formula (IV):

(IV)

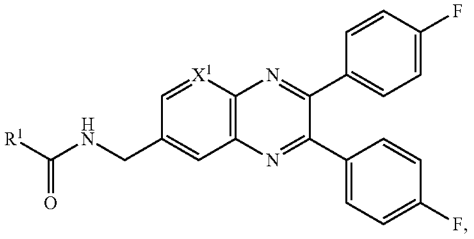

or a pharmaceutically acceptable salt thereof, wherein:

$X^1$ is selected from N and CH;

$R^1$ is selected from $R^{b1}$ and $NR^{c1}R^{d1}$ each $R^{b1}$, R, and $R^{11}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^9$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

98. The compound of paragraph 97, wherein each $R^{b1}$ and $R^{c1}$ is independently selected from 5-10 membered heteroaryl, 4-10 membered heterocycloalkyl, (5-10 membered heteroaryl)-$C_{1-4}$ alkylene, and (4-10 membered heterocycloalkyl)-$C_{1-4}$ alkylene, each of which is optionally substituted with 1 or 2 $R^9$, and $R^{d1}$ is H.

99. The compound of paragraph 97, wherein the compound of Formula (IV) is selected from any one of the compounds listed in Table 13, or a pharmaceutically acceptable salt thereof.

100. A pharmaceutical composition comprising a compound of paragraph 97, or a pharmaceutically acceptable salt thereof, and a pharmaceutically acceptable carrier.

101. A method for inhibiting NAMPT activity within a mammal, wherein said method comprises administering, to said mammal, an effective amount of a compound of paragraph 97, or a pharmaceutically acceptable salt thereof.

102. A compound of Formula (V):

(V)

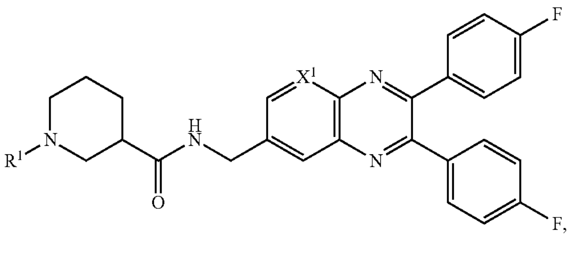

or a pharmaceutically acceptable salt thereof, wherein:

$X^1$ is selected from N and CH;

$R^1$ is selected from H, $S(O)_2R^{b1}$, and $C(O)R^{b1}$;

$R^{b1}$ is selected from $C_{1-6}$ alkyl and $C_{2-6}$ alkynyl, each of which is optionally substituted with a substituent selected from OH, halo, $C_{1-6}$ alkoxy, $C_{1-6}$ haloalkoxy, amino, $C_{1-6}$ alkylamino, and di($C_{1-6}$ alkyl)amino.

103. The compound of paragraph 102, wherein the compound of Formula (V) is selected from any one of the compounds listed in Table 14, or a pharmaceutically acceptable salt thereof.

104. A pharmaceutical composition comprising a compound of paragraph 102, or a pharmaceutically acceptable salt thereof, and a pharmaceutically acceptable carrier.

105. A method for inhibiting NAMPT activity within a mammal, wherein said method comprises administering, to said mammal, an effective amount of a compound of paragraph 102, or a pharmaceutically acceptable salt thereof.

106. A compound of Formula (VI):

(VI)

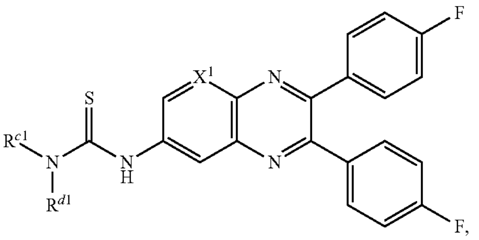

or a pharmaceutically acceptable salt thereof, wherein:

$X^1$ is selected from N and CH;

$R^{c1}$ and $R^{d1}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkenylcarbonyl, $C_{1-6}$ alkynylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

107. The compound of paragraph 106, wherein $R^{d1}$ is H, and $R^{c1}$ is selected from 5-membered heteroaryl, 4-10 membered heterocycloalkyl, (5-10 membered heteroaryl)-$C_{1-4}$ alkylene, and (4-10 membered heterocycloalkyl)-$C_{1-4}$ alkylene, each of which is optionally substituted with 1 or 2 $R^g$; or
any $R^{c1}$ and $R^{d1}$ together with the N atom to which they are attached form a 4-7 membered heterocycloalkyl, which is optionally substituted with $R^g$.

108. The compound of paragraph 106, wherein the compound of Formula (VI) is selected from any one of the compounds listed in Table 15a, or a pharmaceutically acceptable salt thereof.

109. A pharmaceutical composition comprising a compound of paragraph 106, or a pharmaceutically acceptable salt thereof, and a pharmaceutically acceptable carrier.

110. A method for inhibiting NAMPT activity within a mammal, wherein said method comprises administering, to said mammal, an effective amount of a compound of paragraph 106, or a pharmaceutically acceptable salt thereof.

111. A compound selected from any one of the compounds listed in Table 15b, or a pharmaceutically acceptable salt thereof.

112. A pharmaceutical composition comprising a compound of paragraph 111, or a pharmaceutically acceptable salt thereof, and a pharmaceutically acceptable carrier.

113. A method for inhibiting NAMPT activity within a mammal, wherein said method comprises administering, to said mammal, an effective amount of a compound of paragraph 111, or a pharmaceutically acceptable salt thereof.

114. A method of treating a mammal having a disease, disorder, or condition responsive to inhibiting NAMPT activity within the mammal, wherein said method comprises administering, to said mammal, a therapeutically effective amount of:

(i) a compound of Formula (I), as recited in paragraphs 1-80, or a pharmaceutically acceptable salt thereof, or a pharmaceutical composition comprising of paragraph 81, or (ii) a compound of Formula (II), as recited in paragraphs 82-86, or a pharmaceutically acceptable salt thereof, or a pharmaceutical composition comprising of paragraph 87, or (iii) a compound of Formula (III), as recited in paragraphs 89-94, or a pharmaceutically acceptable salt thereof, or a pharmaceutical composition comprising of paragraph 95, or (iv) a compound of Formula (IV), as recited in paragraphs 97-99, or a pharmaceutically acceptable salt thereof, or a pharmaceutical composition comprising of paragraph 100, or (v) a compound of Formula (V), as recited in paragraphs 102-103, or a pharmaceutically acceptable salt thereof, or a pharmaceutical composition comprising of paragraph 104; or (vi) a compound of Formula (VI), as recited in paragraphs 106-108, or a pharmaceutically acceptable salt thereof, or a pharmaceutical composition comprising of paragraph 109.

(vii) a compound of paragraph 111, or a pharmaceutically acceptable salt thereof, or a pharmaceutical composition comprising of paragraph 112.

115. The method of paragraph 114, wherein said disease, disorder, or condition is cancer, an inflammatory condition, an autoimmune condition, or an acute or subacute neuronal injury.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method for inhibiting NAMPT activity within a mammal, wherein said method comprises administering, to said mammal, an effective amount of a compound of Formula (I):

(I)

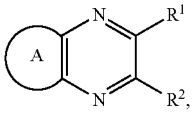

or a pharmaceutically acceptable salt thereof, wherein:

ring A is selected from $C_{5-7}$ cycloalkyl, phenyl, and pyridinyl, each of which is optionally substituted with 1, 2, or 3 substituents independently selected from $R^A$;

each $R^A$ is independently selected from $Cy^1$, halo, CN, $NO_2$, $C_{1-6}$ alkyl, $C_{1-6}$ haloalkyl, $OR^{a1}$, $C(O)NR^{c1}R^{d1}$, $C(NR^{e1})NR^{c1}R^{d1}$, $C(NR^{e1})NR^{c1}OR^{a1}$, $C(O)OR^{a1}$, $NR^{c1}R^{d1}$ $NR^{c1}C(O)R^{b1}$, $NR^{c1}C(O)OR^{a1}$, $NR^{c1}C(O)NR^{c1}R^{d1}$, $NR^{c1}C(S)NR^{c1}R^{d1}$, and $S(O)_2NR^{c1}R^{d1}$;

wherein said $C_{1-6}$ alkyl, are each optionally substituted with 1, 2, or 3 substituents independently selected from $R^7$;

each $R^7$ is independently selected from $OR^{a1}$, $NR^{c1}R^{d1}$, $NR^{c1}C(O)R^{b1}$ $NR^{c1}C(O)NR^{c1}R^{d1}$;

each $Cy^1$ is independently selected from $C_{6-10}$ aryl, 5-10 membered heteroaryl, each of which is optionally substituted with 1, 2, 3, 4, or 5 substituents independently selected from $R^{Cy1}$;

each $R^{Cy1}$ is independently selected from halo, $C_{1-6}$ alkyl, $C_{1-6}$ haloalkyl, $C_{2-6}$ alkenyl, $C_{2-6}$ alkynyl, $OR^{a1}$, $NR^{c1}R^{d1}$, and $S(O)_2R^{b1}$, wherein said $C_{1-6}$ alkyl, $C_{2-6}$ alkenyl, $C_{2-6}$ alkynyl, are each optionally substituted with 1, 2, or 3 substituents independently selected from $R^8$;

each $R^8$ is independently selected from 5-10 membered heteroaryl, $OR^{a1}$, $NR^{c1}R^{d1}$, wherein said 5-10 membered heteroaryl are each optionally substituted with 1, 2, 3, 4, or 5 substituents independently selected from $R^g$;

$R^1$ is selected from $R^9$, $N(R^N)Ph$, and $S(O)_2R^9$;

$R^2$ is selected from $R^9$, $N(R^N)Ph$, and $S(O)_2R^9$;

$R^N$ is selected from H, $C_{1-4}$ alkyl, and $C_{1-4}$ haloalkyl;

each $R^9$ is independently selected from $C_{1-3}$ haloalkyl, $C_{6-10}$ aryl and 5- to 7-membered heteroaryl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $OR^{a1}$, $NR^{c1}R^{d1}$, $NR^{c1}C(O)R^{b1}$, $NR^{c1}S(O)_2R^{b1}$, and $S(O)^2R^{b1}$; wherein said $C_{1-6}$ alkyl are each optionally substituted with 1, 2, or 3 substituents independently selected from $R^{11}$;

each $R^{11}$ is independently selected from $OR^{a1}$, $NR^{c1}R^{d1}$, and $NR^{c1}C(O)R^{b1}$;

each $R^{e1}$ is selected from H;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from $C_{1-6}$ alkyl, $C_{1-6}$ alkoxy, and $C_{1-6}$ alkylcarbonylamino;

provided that if the compound of Formula (I) has formula (i):

(i)

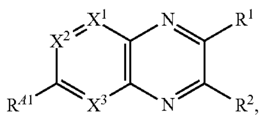

in which $X^1$, $X^2$, and $X^3$ are each independently selected from N, CH, and $CR^A$, and $R^{A1}$ is selected from $C(O)R^{b1}$ and $C(O)NR^{c1}R^{d1}$, then (i) at least one of $X^1$, $X^2$, and $X^3$ is N; or (ii) at least one of $R^1$ and $R^2$ is selected from $C_{1-6}$ haloalkyl and $S(O)_2R^9$.

2. The method of claim 1, wherein the compound of Formula (Ia) has formula:

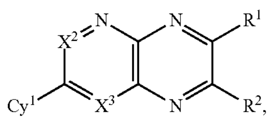

or a pharmaceutically acceptable salt thereof, wherein:

$X^2$ and $X^3$ are each independently selected from N, CH, and $CR^A$.

3. The method of claim 2, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$Cy^1$ is 5-10 membered heteroaryl, optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$ wherein said $C_{1-6}$ alkyl is optionally substituted with 1, 2, or 3 substituents independently selected from $R^8$; and each $R^8$ is independently selected from $OR^{a1}$ and $NR^{c1}R^{d1}$.

4. The method of claim 3, wherein:

$R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$; or $R^1$ is $C_{1-3}$ haloalkyl; and $R^2$ is $C_{6-10}$ aryl, optionally substituted with 1, 2, or 3 substituents independently selected from $R^{10}$; or $R^1$ is $C_{6-10}$ aryl, optionally substituted with 1, 2, or 3 substituents independently selected from $R^{10}$; and $R^2$ is $C_{1-3}$ haloalkyl; or $R^1$ is 5-7 membered heteroaryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$, or $R^1$ is $C_{6-10}$ aryl, optionally substituted with 1, 2, or 3 substituents independently selected from $R^{10}$; and $R^2$ is 5-7 membered heteroaryl, optionally substituted with 1, 2, or 3 substituents independently selected from $R^{10}$, and each $R^{10}$ is independently selected from halo and $S(O)_2R^{b1}$.

5. The method of claim 2, wherein:

each $R^A$ is independently selected from H, halo, $C_{1-6}$ alkyl, and $C_{1-6}$ alkoxy;

$Cy^1$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^{Cy1}$;

each $R^{Cy1}$ is independently selected from halo, $C_{1-6}$ alkyl, $OR^{a1}$, $NR^{c1}R^{d1}$, and $S(O)_2R^{b1}$, wherein said $C_{1-6}$ alkyl is optionally substituted with 1, 2, or 3 substituents independently selected from $R^8$; and each $R^8$ is independently selected from $OR^{a1}$ and $NR^{c1}R^{d1}$.

6. The method of claim 5, wherein:

$R^1$ is phenyl, optionally substituted with 1, 2, or 3 substituents independently selected from $R^{10}$; and $R^2$ is phenyl, optionally substituted with 1, 2, or 3 substituents independently selected from $R^{10}$; or $R^1$ is trifluoromethyl; and $R^2$ is phenyl, optionally substituted with 1, 2, or 3 substituents independently selected from $R^{10}$; or $R^1$ is thiophenyl, optionally substituted with 1, 2, or 3 substituents independently selected from $R^{10}$; and $R^2$ is phenyl, optionally substituted with 1, 2, or 3 substituents independently selected from $R^{10}$; or $R^1$ is phenyl, optionally substituted with 1, 2, or 3 substituents independently selected from $R^{10}$; and $R^2$ is thiophenyl, optionally substituted with 1, 2, or 3 substituents independently selected from $R^{10}$; or $R^1$ is phenyl, optionally substituted with 1, 2, or 3 substituents independently selected from $R^{10}$, and $R^2$ is trifluoromethyl; and each $R^{10}$ is independently selected from halo and $S(O)_2R^{b1}$.

7. The method of claim 1, wherein the compound of Formula (I) has Formula (Ib):

(Ib)

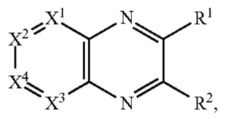

or a pharmaceutically acceptable salt thereof, wherein:

$X^1$, $X^2$, $X^3$, and $X^4$ are each independently selected from N, CH, and $CR^A$;

$R^1$ is selected from $C_{1-6}$ haloalkyl and $S(O)_2R^9$; and $R^2$ is $R^9$.

8. The method of claim 7, wherein the compound of Formula (Ib) has formula:

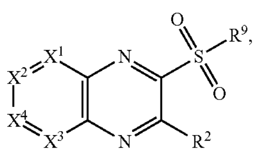

or a pharmaceutically acceptable salt thereof.

9. The method of claim 7, wherein the compound of Formula (Ib) is selected from:

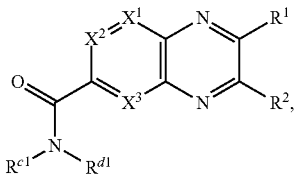

and

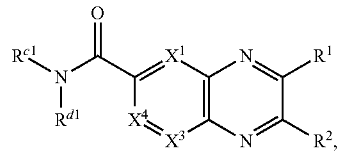

or a pharmaceutically acceptable salt thereof, wherein:

$X^1$ is selected from N, CH, and $CR^A$;

$X^2$ is selected from CH and $CR^A$;

$X^3$ is selected from N, CH, and $CR^A$; and $X^4$ is selected from CH and $CR^A$.

10. The method of claim 9, wherein:

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$;

or any $R^{c1}$ and $R^{d1}$ together with the N atom to which they are attached form a 4-7 membered heterocycloalkyl, which is optionally substituted with 1 or 2 substituents independently selected from $R^g$;

each $R^9$ is independently selected from $C_{6-10}$ aryl and 5-7 membered heteroaryl, each of which is optionally substituted with 1, 2, or 3 independently selected $R^{10}$;

each $R^{10}$ is independently selected from halo and $C_{1-6}$ alkyl.

11. The method of claim 1, wherein the compound of Formula (I) has Formula (Ic):

(Ic)

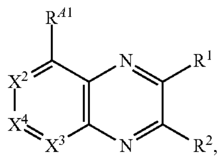

or a pharmaceutically acceptable salt thereof, wherein:

$X^3$ is selected from N, CH, and $CR^A$, $X^2$ is selected from CH and $CR^A$;

$X^4$ is selected from CH and $CR^A$, and $R^{A1}$ is selected from $C(O)NR^{c1}R^{d1}$ and $C(O)OR^{a1}$.

12. The method of claim 11, wherein:

each $R^A$ is independently selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^{c1}$ and $R^{d1}$ are each independently selected from H, $C_{1-6}$ alkyl, $C_{1-4}$ haloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$; or $R^{c1}$ and $R^{d1}$ together with the N atom to which they are attached form a 4-7 membered heterocycloalkyl, which is optionally substituted with 1 or 2 substituents independently selected from $R^g$;

$R^1$ and $R^2$ are each independently an $C_{6-10}$ aryl, optionally substituted with 1, 2, or 3 independently selected $R^{10}$; and each $R^{10}$ is independently selected from halo and $C_{1-6}$ alkyl.

13. A method of claim 1, wherein the compound of Formula (I) has Formula (Id):

(Id)

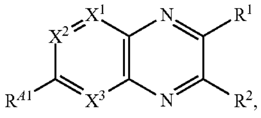

or a pharmaceutically acceptable salt thereof, wherein:

$X^1$ is selected from N, CH, and $CR^A$;

$X^3$ is selected from N, CH, and $CR^A$, $X^2$ is selected from CH and $CR^A$, and $R^{A1}$ is selected from $NR^{c1}R^{d1}$, $NR^{c1}C(O)R^{b1}$, $NR^{c1}C(O)OR^{a1}$, and $NR^{c1}C(O)$ $NR^{c1}R^{d1}$.

14. The method of claim 13, wherein:

each $R^A$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^{a1}$ is selected from $C_{1-6}$ alkyl, $C_{1-4}$ haloalkyl, $C_{2-6}$ alkenyl, and $C_{2-6}$ alkynyl, each of which is optionally substituted with 1 or 2 $R^g$;

$R^{b1}$ is selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1 or 2 $R^g$;

each $R^{c1}$ and $R^{d1}$ is independently selected from H, $C_{1-6}$ alkyl, $C_{2-6}$ alkynyl, $C_{3-10}$ cycloalkyl, 4-10 membered heterocycloalkyl, 5-10 membered heteroaryl, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1 or 2 independently selected $R^g$; or $R^{c1}$ and $R^{d1}$ together with the N atom to which they are attached form a 4-7 membered heterocycloalkyl, which is optionally substituted with 1 or 2 substituents independently selected from $R^g$;

$R^1$ and $R^2$ are each independently an $C_{6-10}$ aryl, optionally substituted with 1, 2, or 3 independently selected $R^{10}$; and each $R^{10}$ is independently selected from halo and $C_{1-6}$ alkyl.

15. The method of claim 1, wherein the compound of Formula (I) has Formula (Ie):

(Ie)

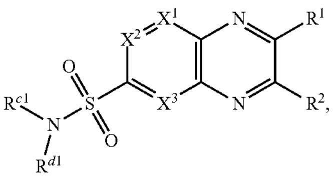

or a pharmaceutically acceptable salt thereof, wherein:

$X^1$ is selected from N, CH, and $CR^A$;

$X^3$ is selected from N, CH, and $CR^A$, and $X^2$ is selected from CH and $CR^A$.

16. The method of claim 15, wherein:

each $R^A$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$R^{c1}$ and $R^{d1}$ are each independently selected from $C_{1-6}$ alkyl, $C_{3-10}$ cycloalkyl, (4-10 membered heterocycloalkyl)-$C_{1-4}$ alkylene, and (5-10 membered heteroaryl)-$C_{1-4}$ alkylene, each of which is optionally substituted with 1 or 2 $R^g$;

$R^1$ and $R^2$ are each independently an $C_{6-10}$ aryl, optionally substituted with 1 or 2 independently selected $R^{10}$, and each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

17. The method of claim 1, wherein the compound of Formula (I) is selected from:

(If)

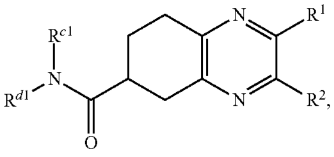

and (Ig)

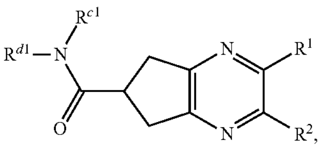

or a pharmaceutically acceptable salt thereof.

18. The method of claim 17, wherein:

$R^{c1}$ and $R^{d1}$ together with the N atom to which they are attached form a 4-7 membered heterocycloalkyl, which is optionally substituted with 1, 2, or 3 substituents independently selected from $R^g$;

$R^1$ and $R^2$ are each independently an $C_{6-10}$ aryl, optionally substituted with 1, 2, or 3 substituents independently selected from $R^{10}$; and each $R^{10}$ is independently a halo.

19. A method for inhibiting NAMPT activity within a mammal, wherein said method comprises administering, to said mammal, an effective amount of a compound selected from any one of the following compounds:

BC19192

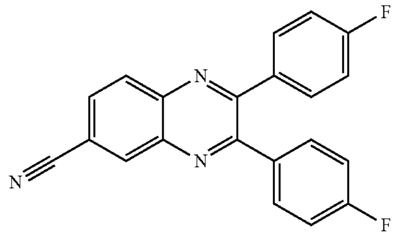

BC19194

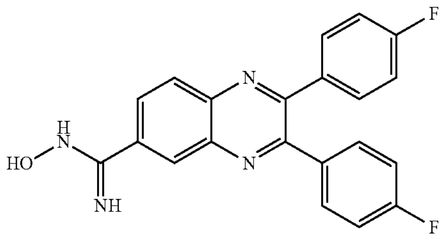

BC19578

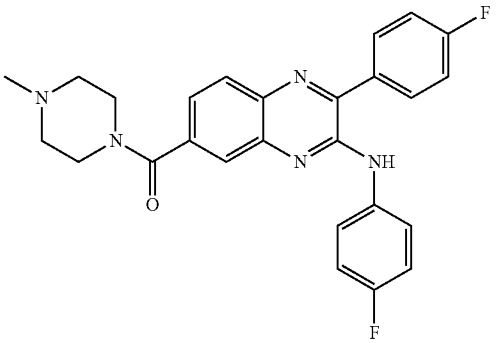

BC19668

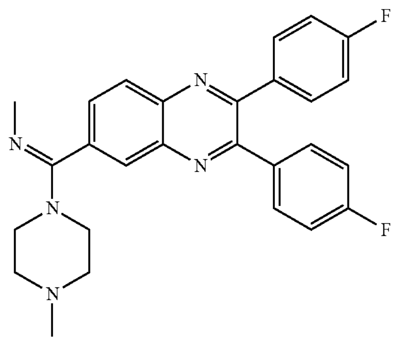

-continued
BC19577
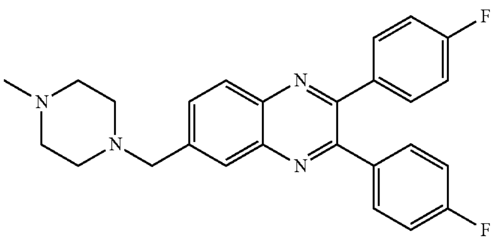
BC19403
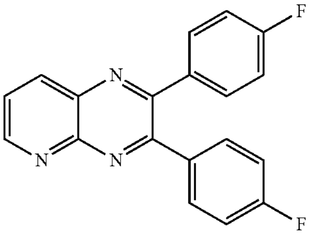
BC19408
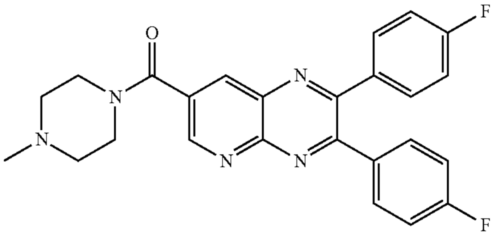
BC19512
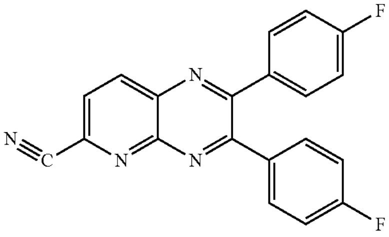
BC19448
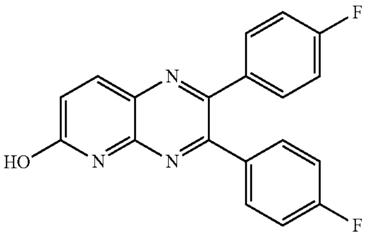
BC19666
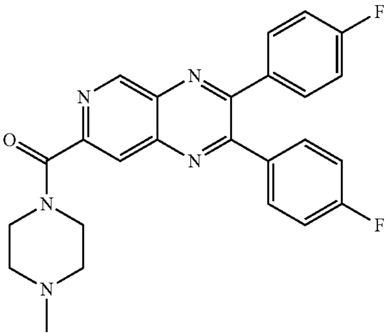
-continued
BC19101
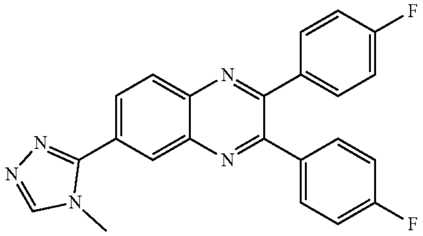
BC19139
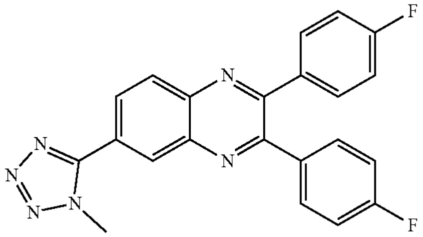
BC19140
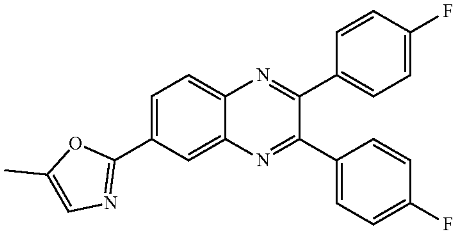
BC19141
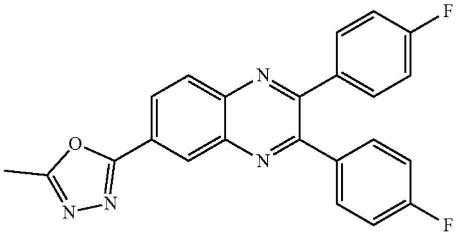
BC19143
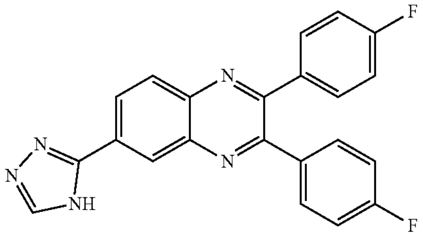
BC19148
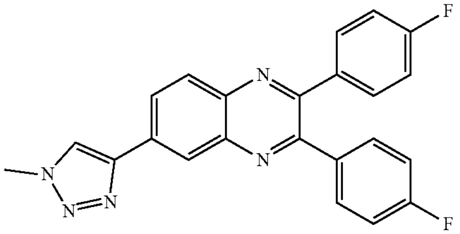

-continued
BC19150
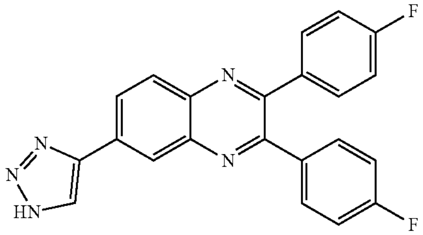
BC19238
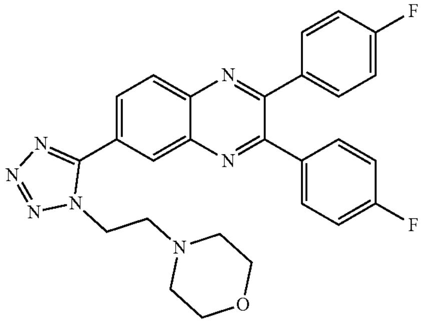
BC19240
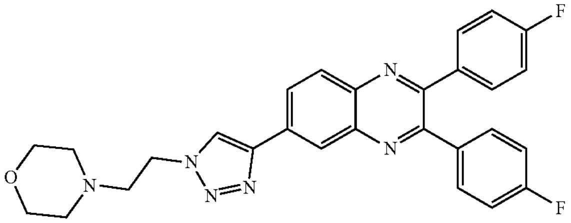
BC19241
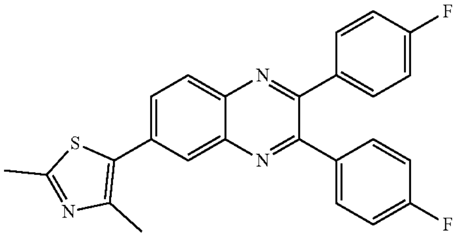
BC19242
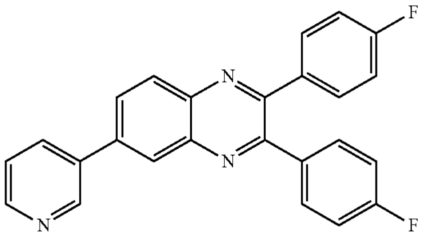
BC19243
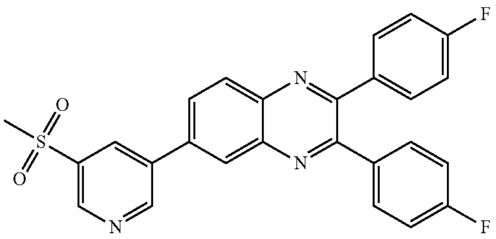
-continued
BC19244
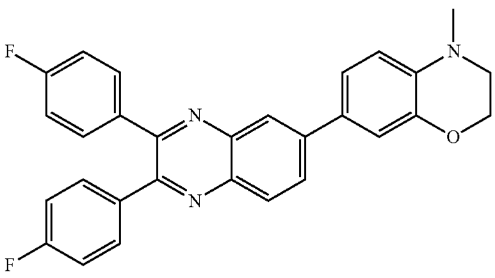
BC19245
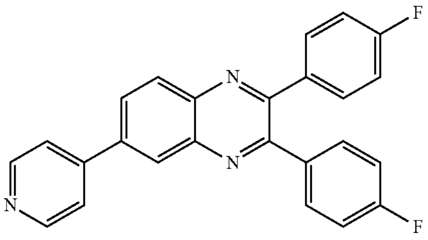
BC19246
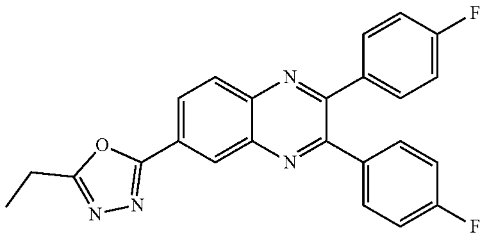
BC19247
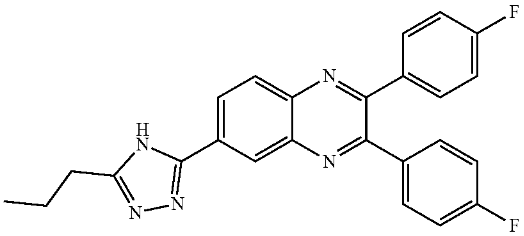
BC19250
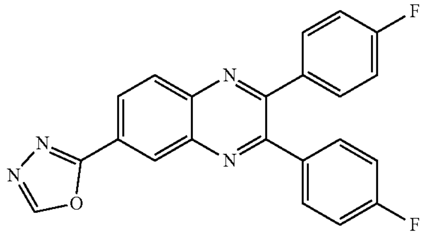
BC19301
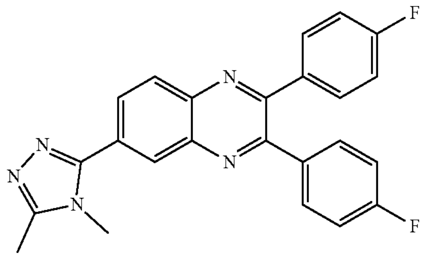

BC19302
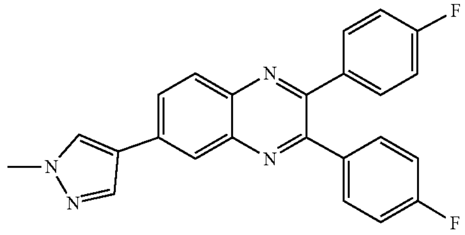
BC19304
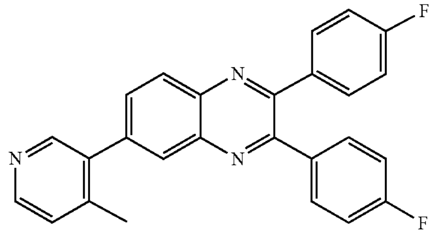
BC19305
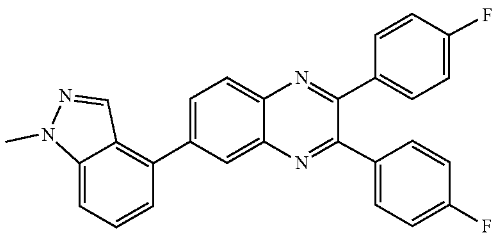
BC19306
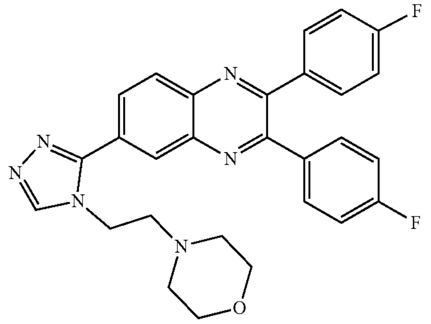
BC19396
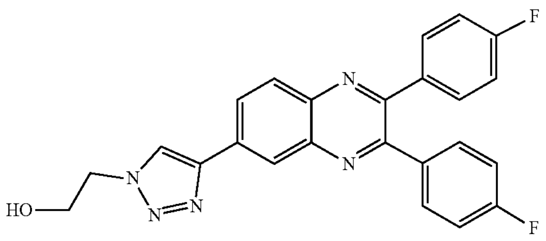
BC19404
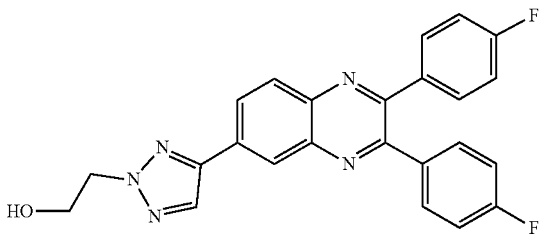
-continued
BC19112
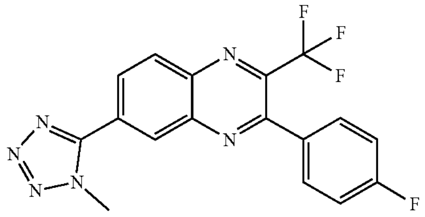
BC19152
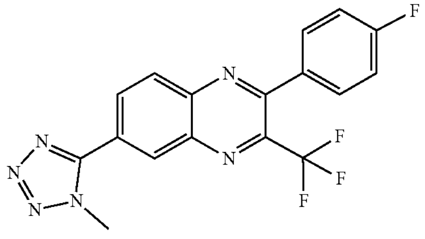
BC19159
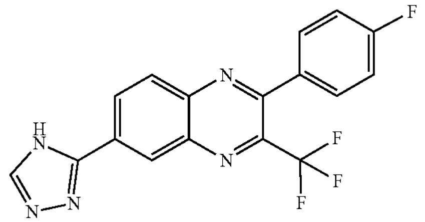
BC19401
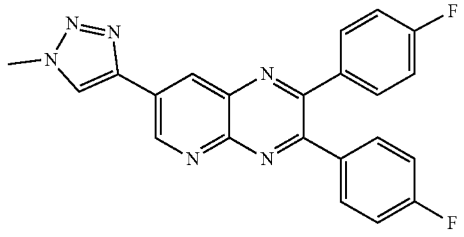
BC19402
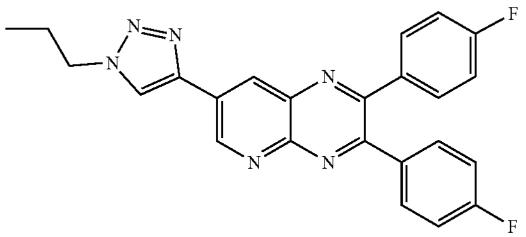
BC19619
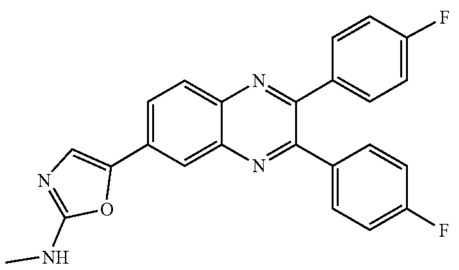

-continued
BC19664
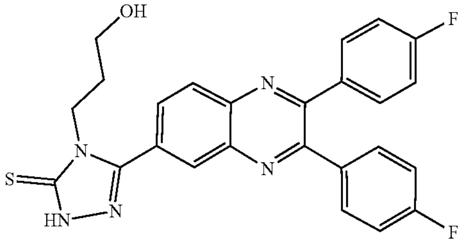
BC19665
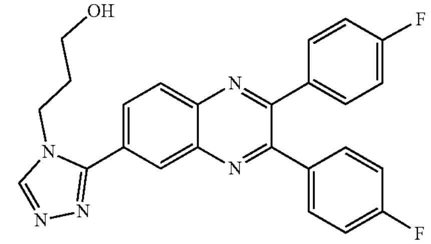
BC19667
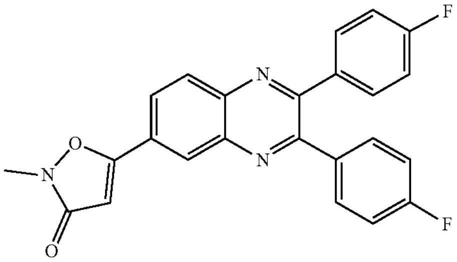
BC19496
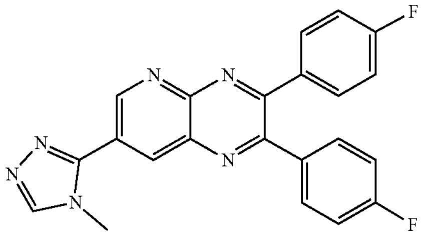
BC19103
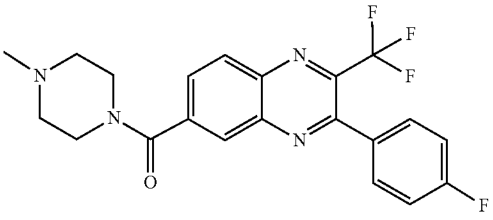
BC19142
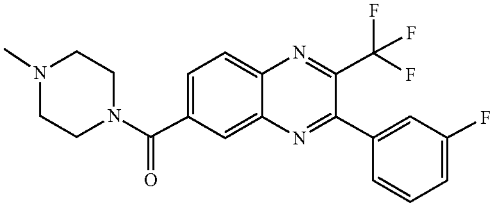
-continued
BC19307
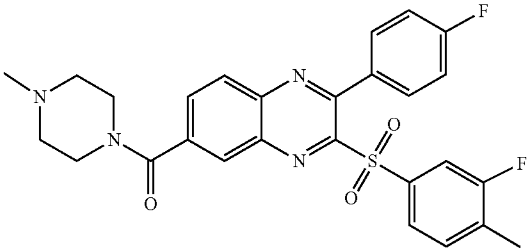
BC19308
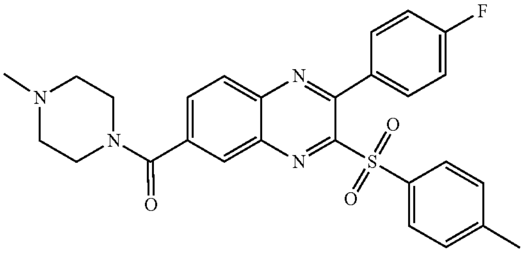
BC19395
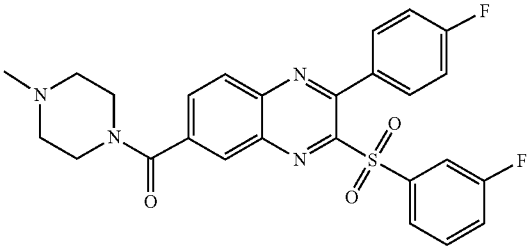
BC19321
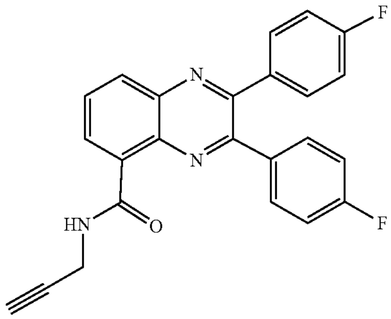
BC19400
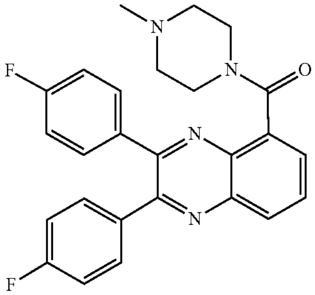

-continued
BC19195
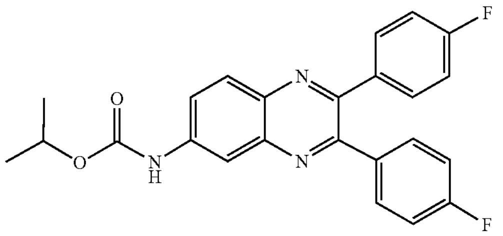
BC19239
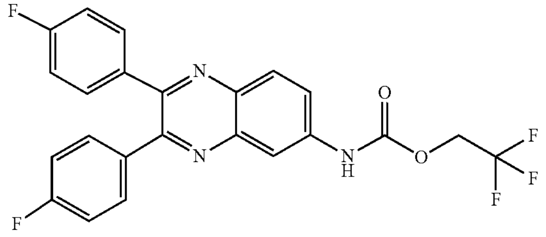
BC19251
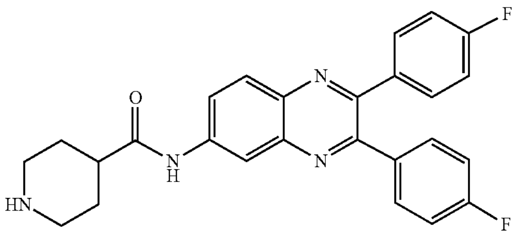
BC19309
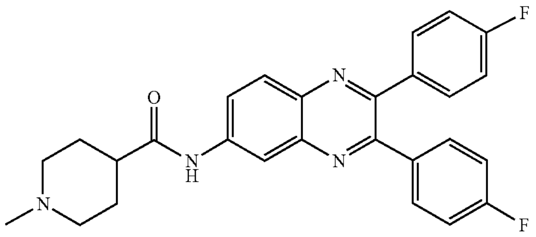
BC19310
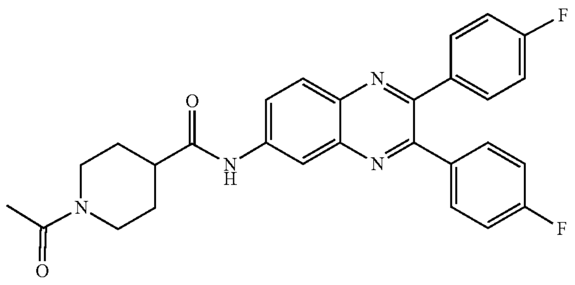
BC19311
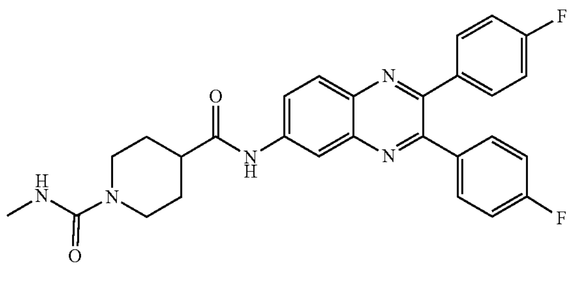
-continued
BC19312
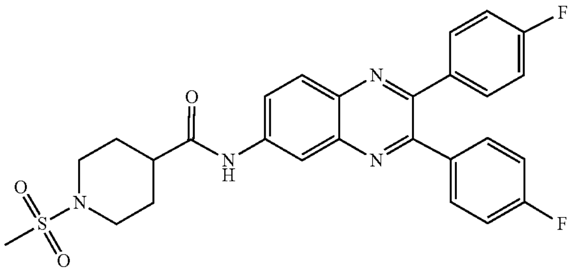
BC19313
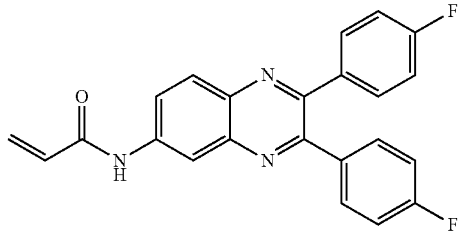
BC19314
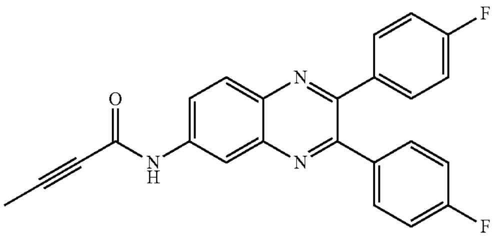
BC19315
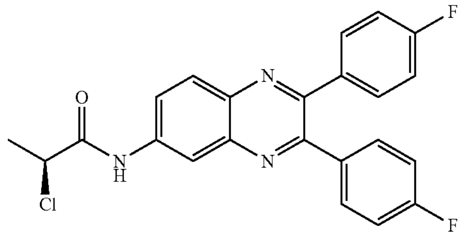
BC19397
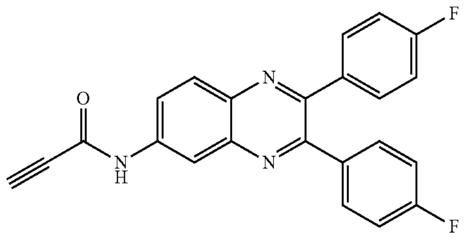

-continued
BC19494
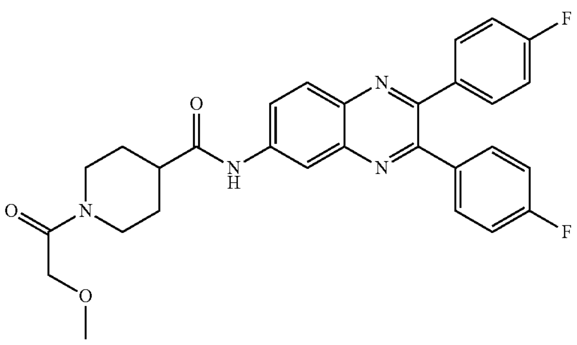
BC19510
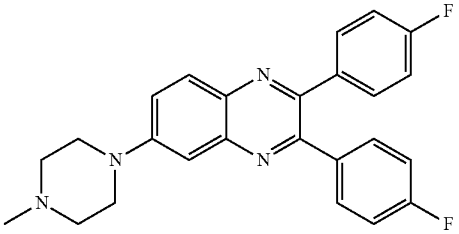
BC19511
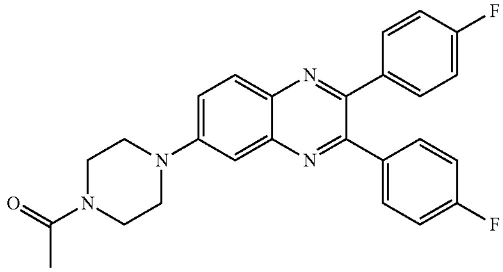
BC19563
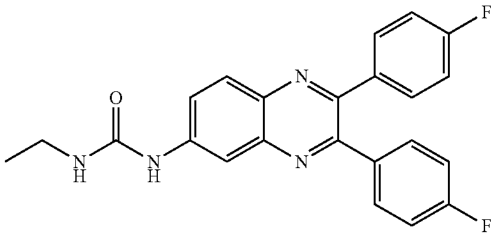
BC19564
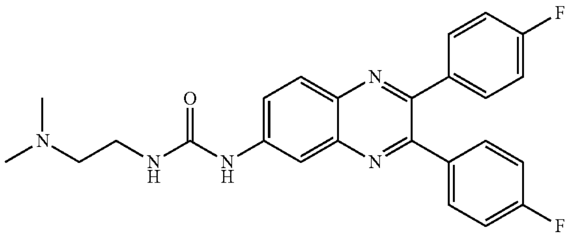
-continued
BC19565
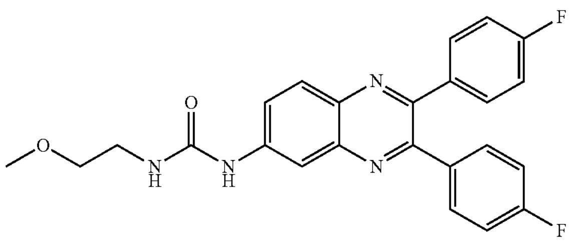
BC19566
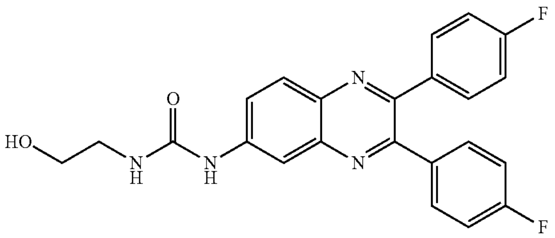
BC19567
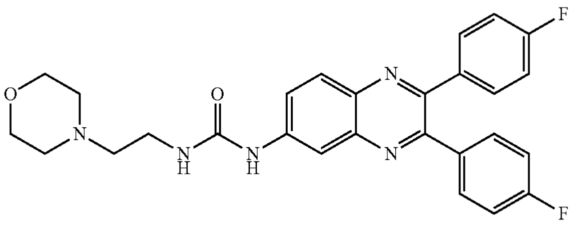
BC19568
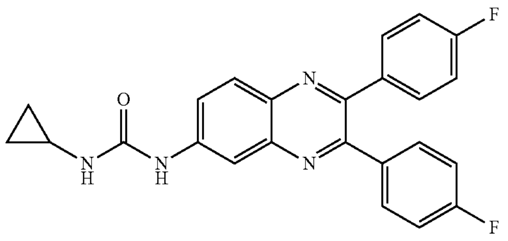
BC19569
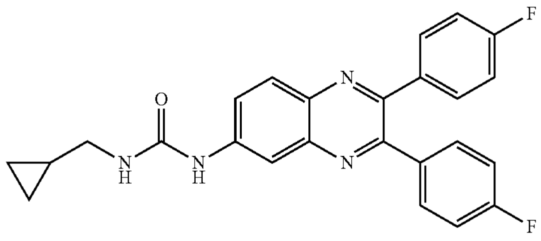
BC19570
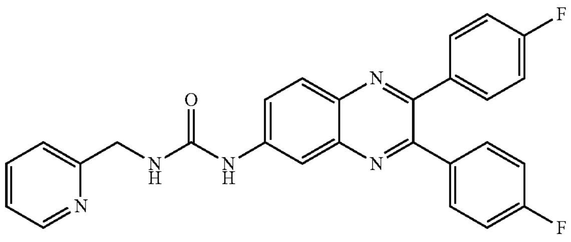

-continued
BC19571
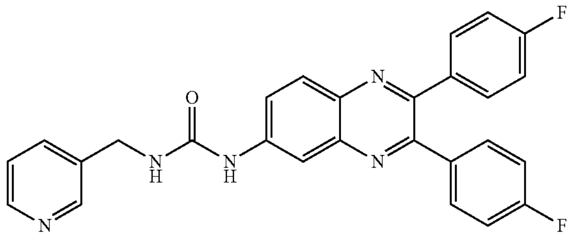
BC19572
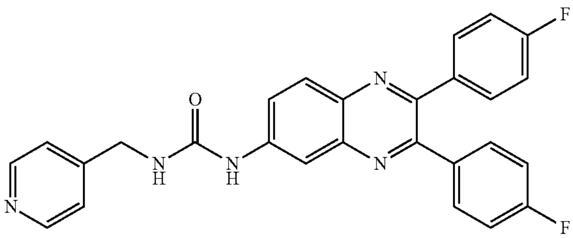
BC19573
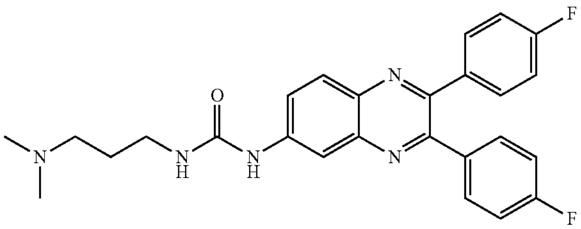
BC19574
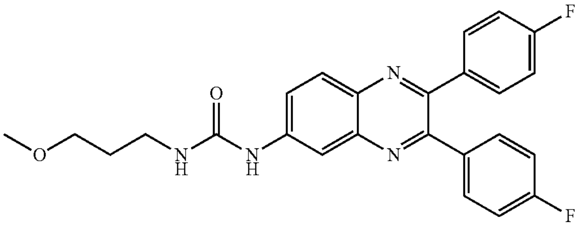
BC19575
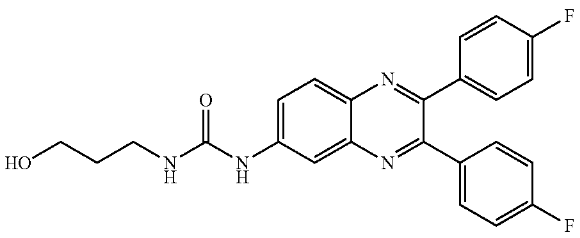
BC19576
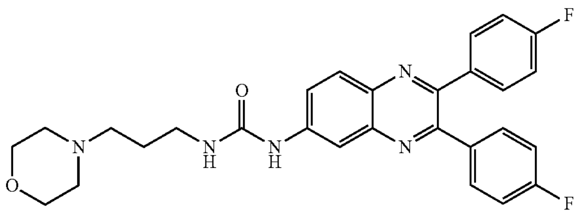
-continued
BC19616
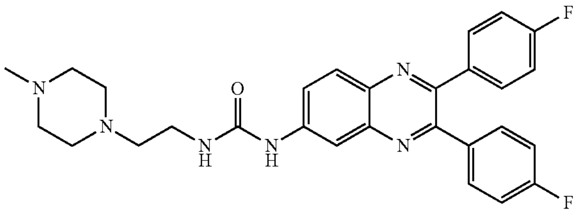
BC19617
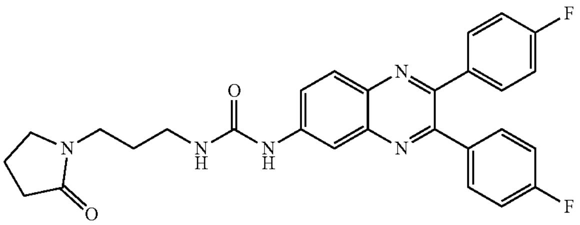
BC20317
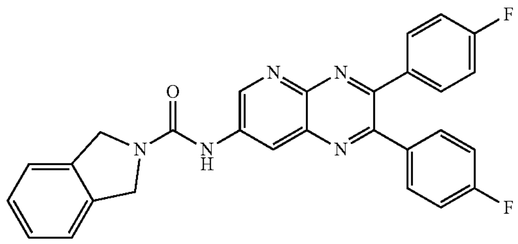
BC20321
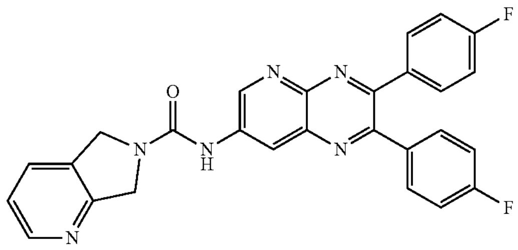
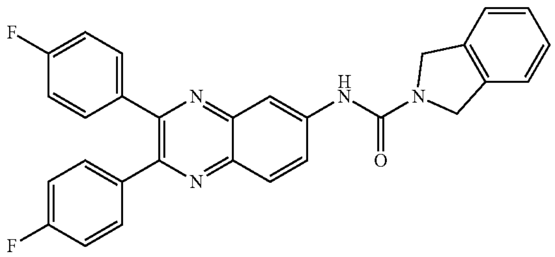
BC20330
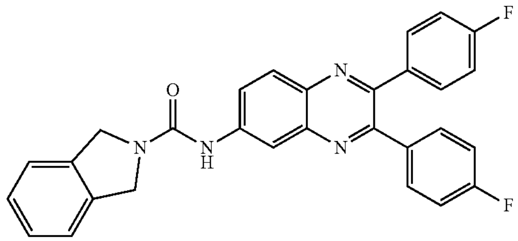

-continued
BC20333
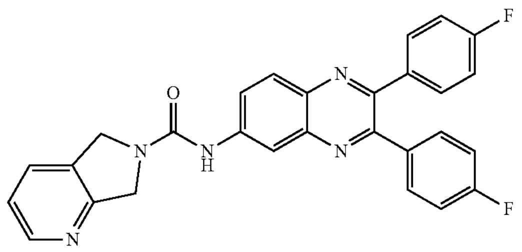
BC20334
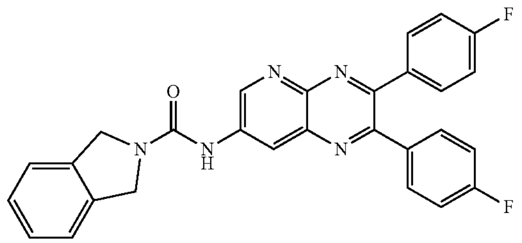
ZE18-0567
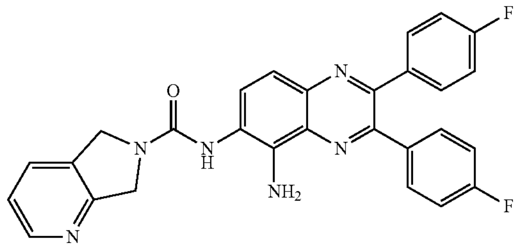
BC20218
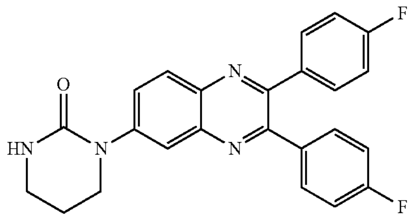
BC20219
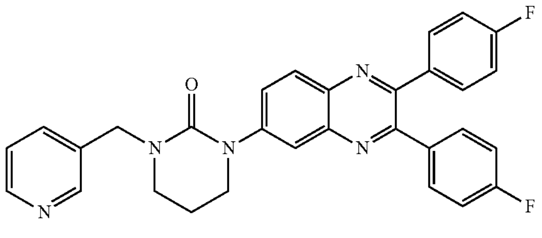
BC20226
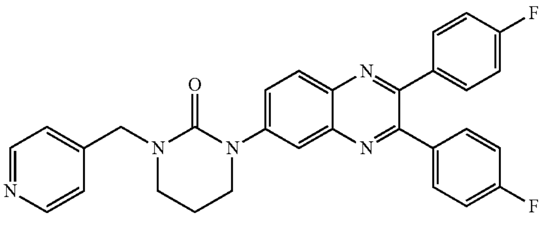
-continued
BC20277
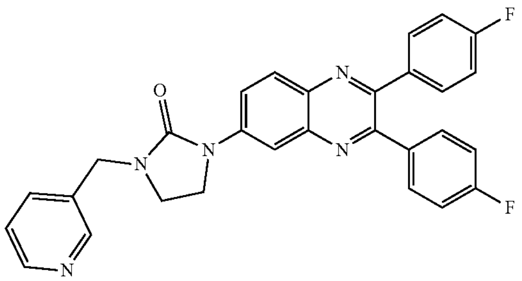
BC20291
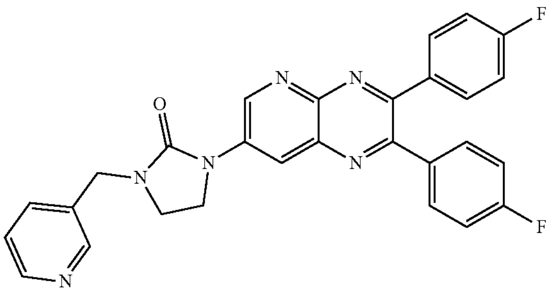
BC20297
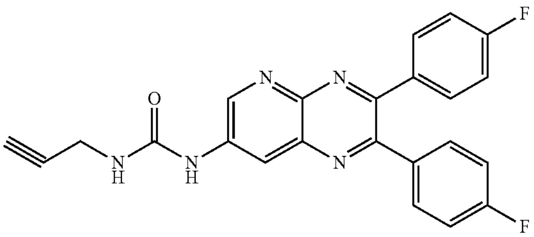
BC20312
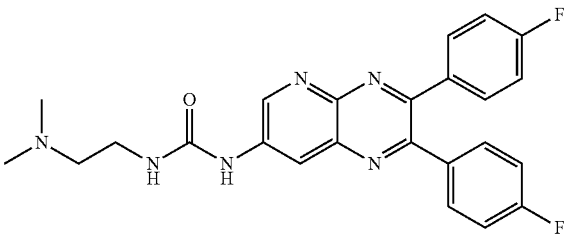
BC20298
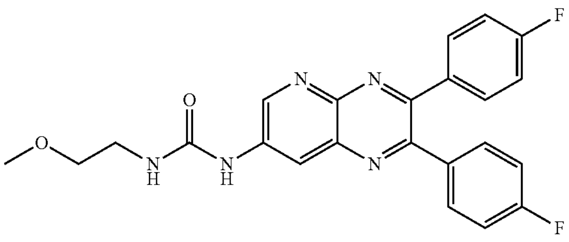

-continued
BC20299
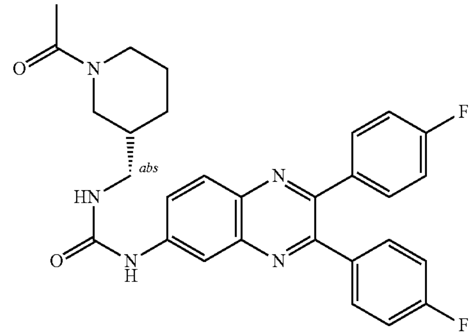
BC20300
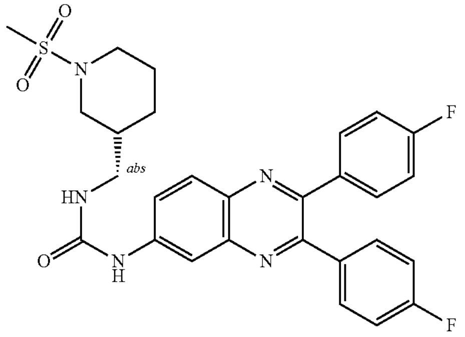
BC20217
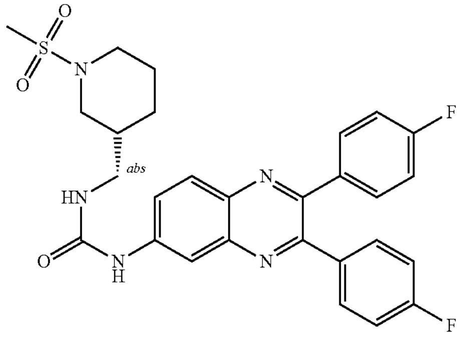
BC20225
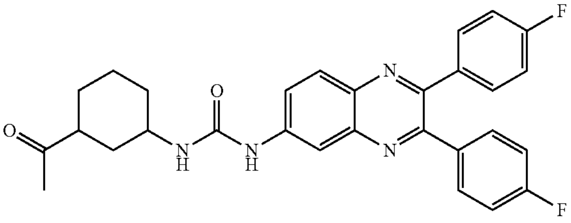
BC20237
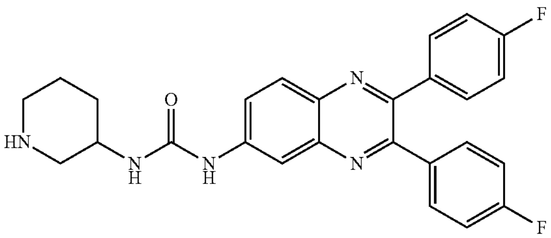
-continued
BC20238
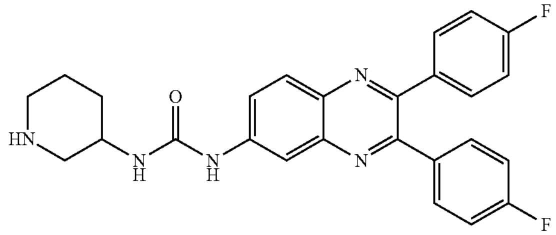
BC20239
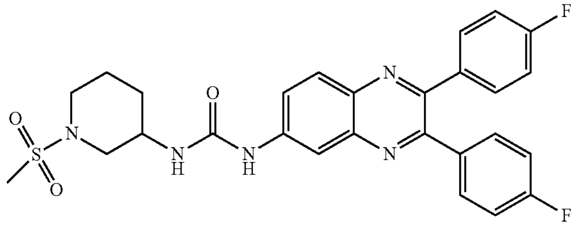
BC20255
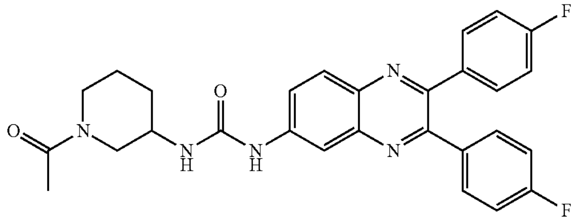
BC20256
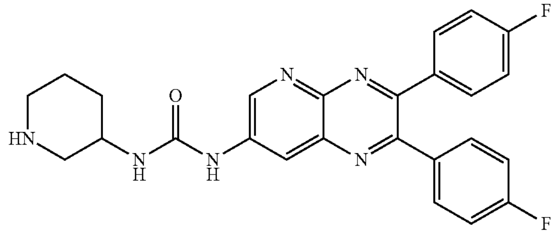
BC20269
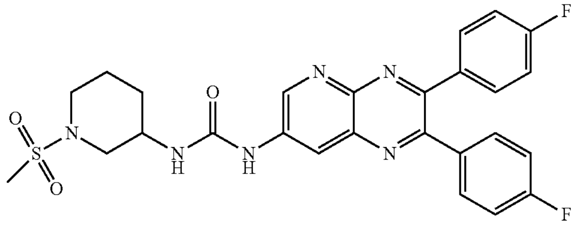
BC20293
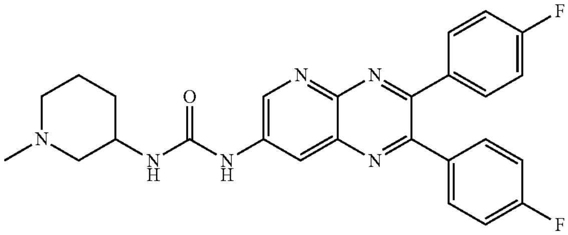

-continued
BC20207
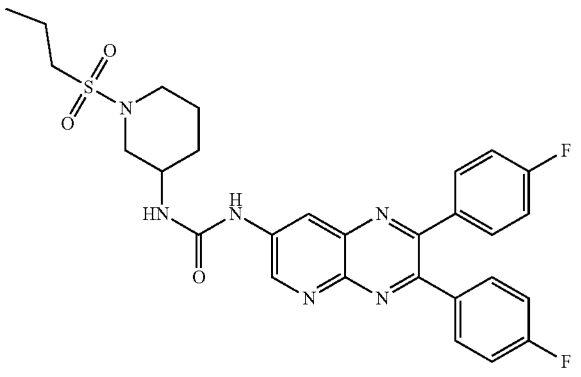
BC20310
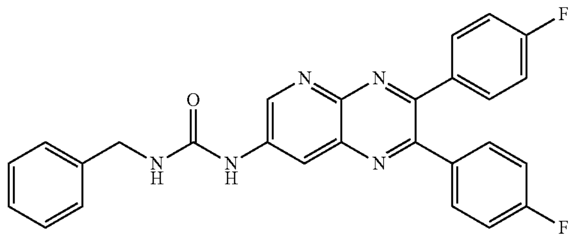
BC20311
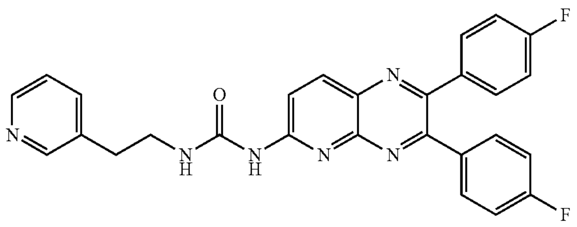
BC20224
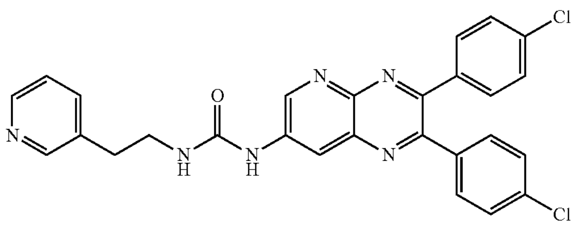
BC20254
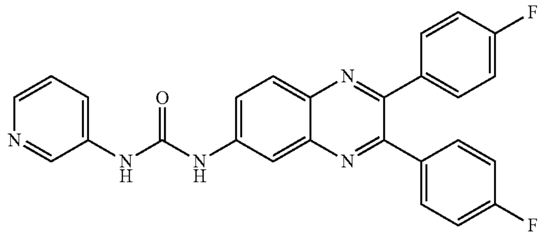
-continued
BC20213
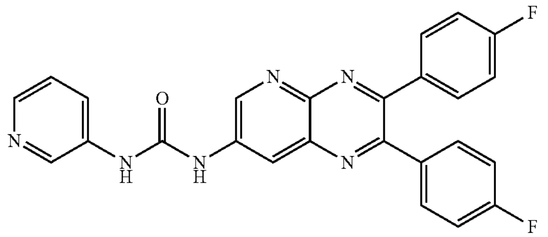
BC20316
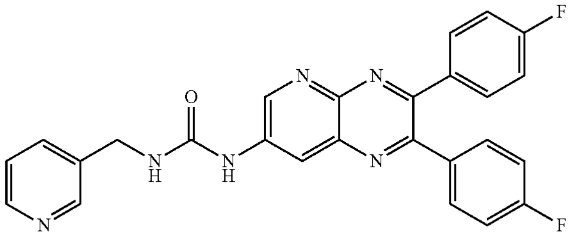
BC20216
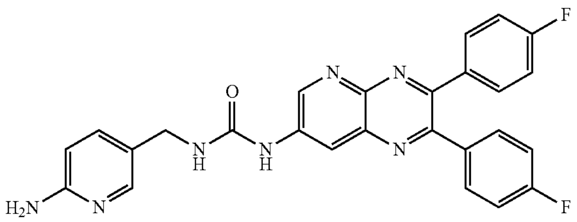
BC20268
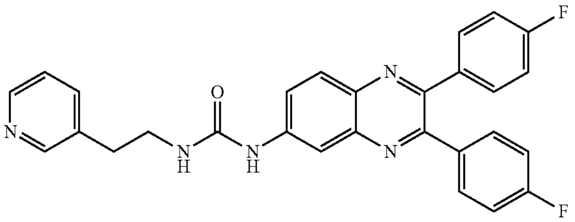
BC20314
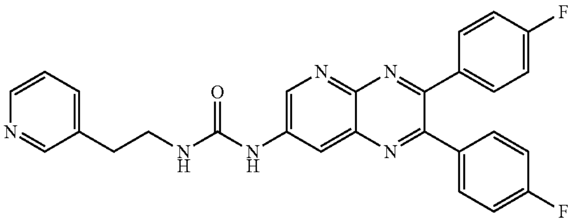
BC20315
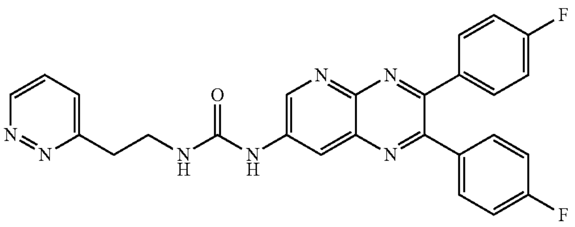

-continued
BC20318
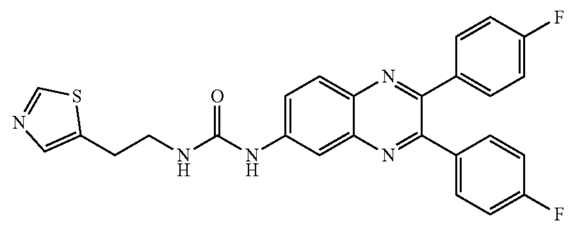
BC20320
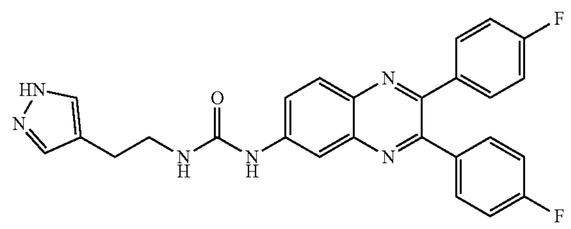
BC20331
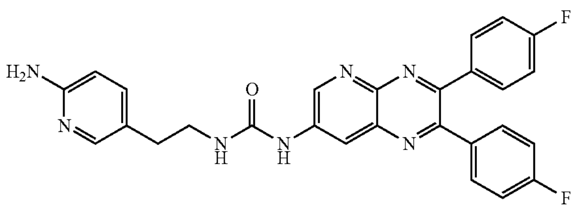
BC20319
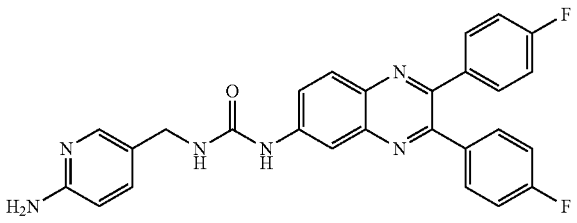
BC19504
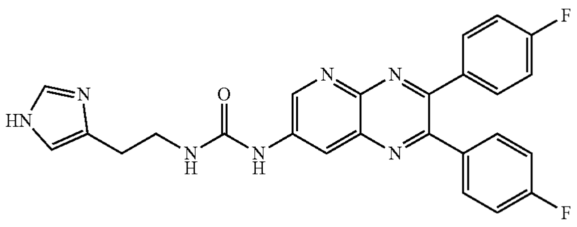
BC19505
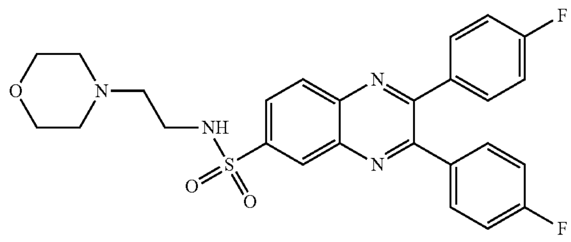
BC19506
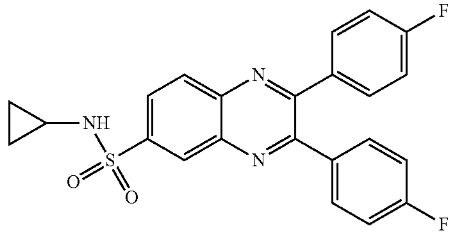
BC19507
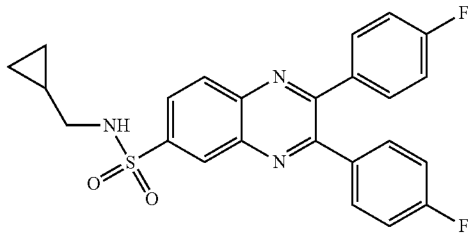
BC19508
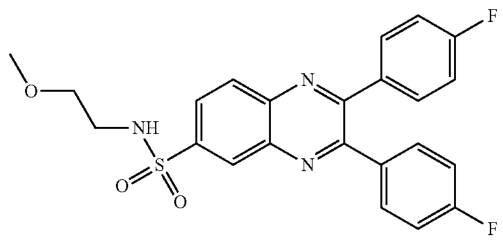
BC19509
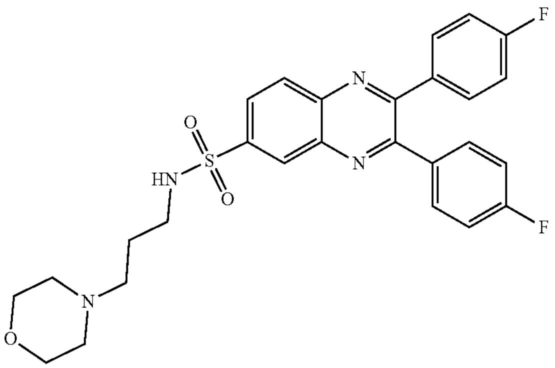
BC19554
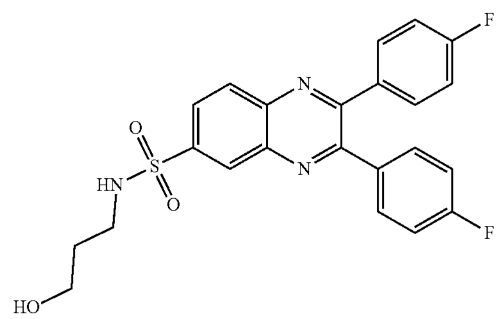

-continued
BC19555
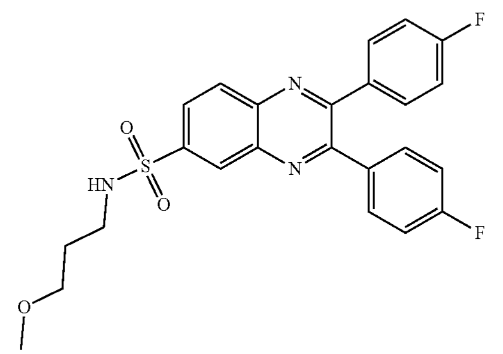
BC19556
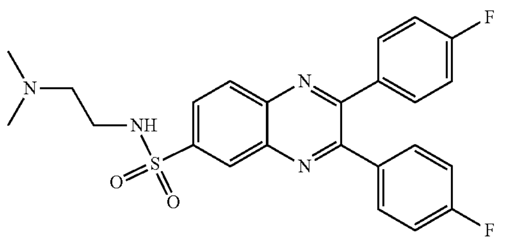
BC19557
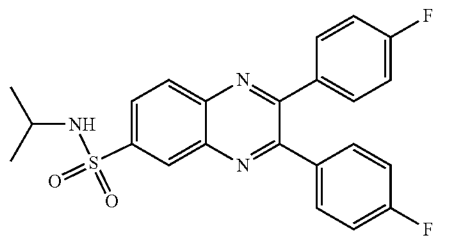
BC19559
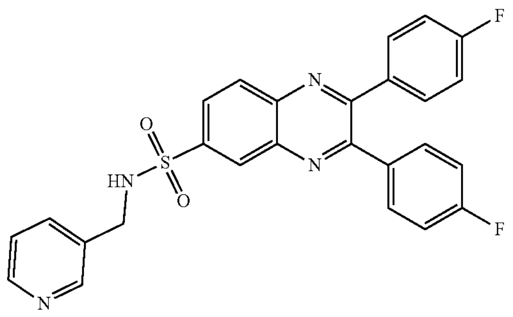
BC19560
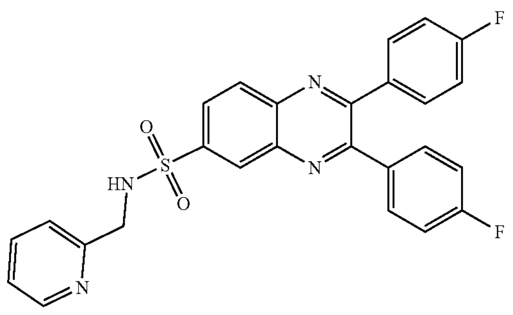
-continued
BC19561
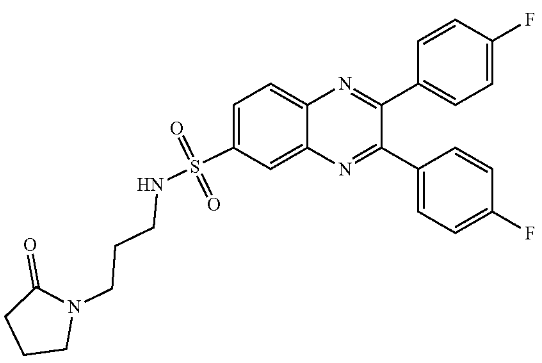
BC19562
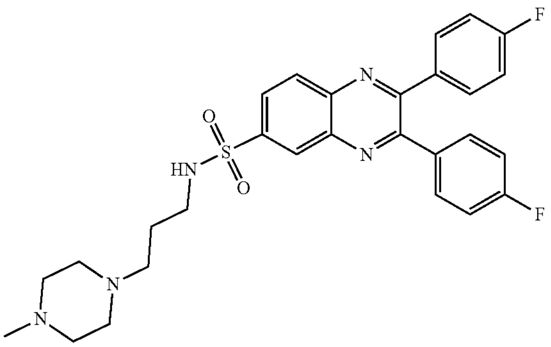
BC19663
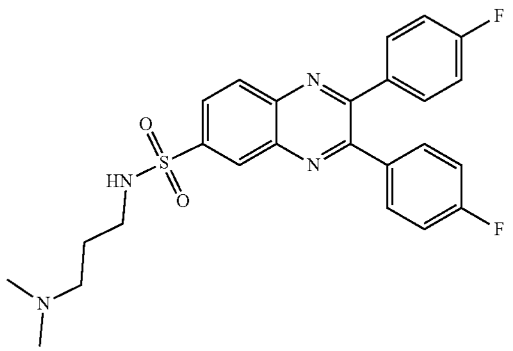
BC19723
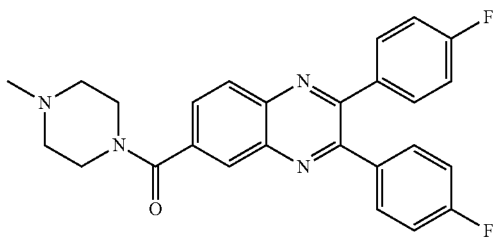
BC20202
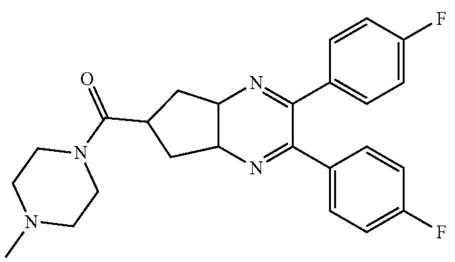

-continued
BC20203
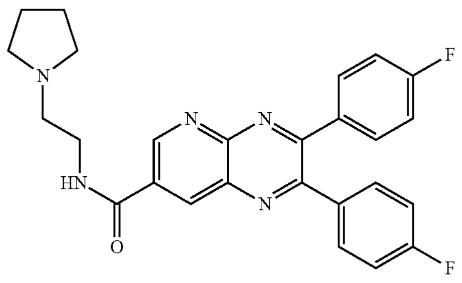
BC20204
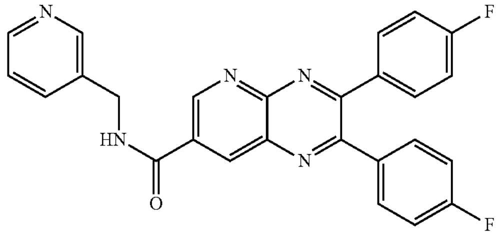
BC20205
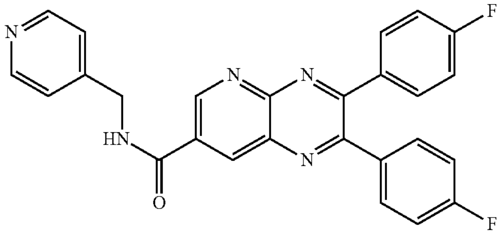
BC20206
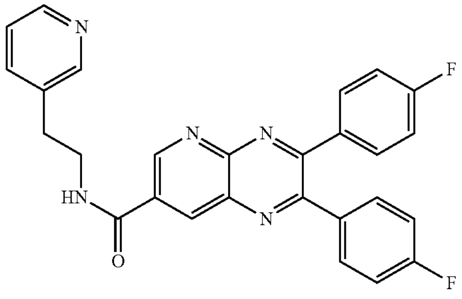
BC20208
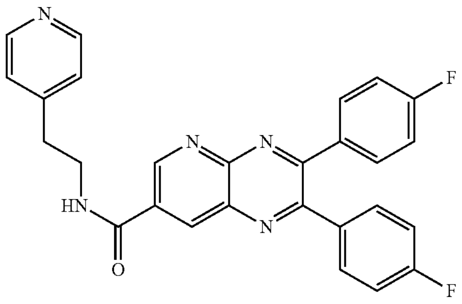
-continued
BC20209
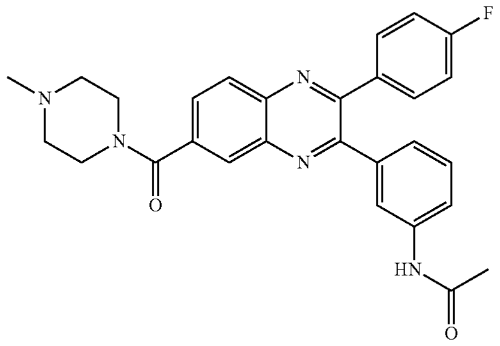
BC20210
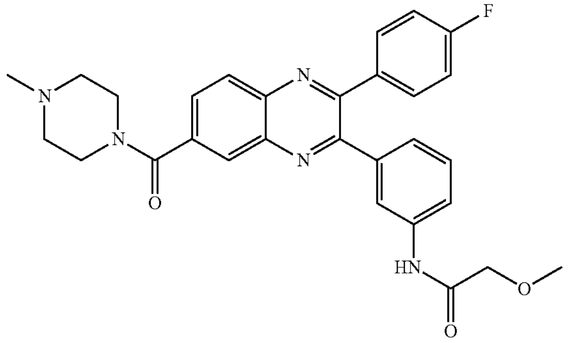
BC20211
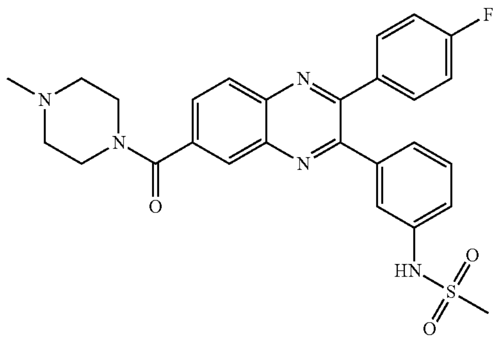
BC20212
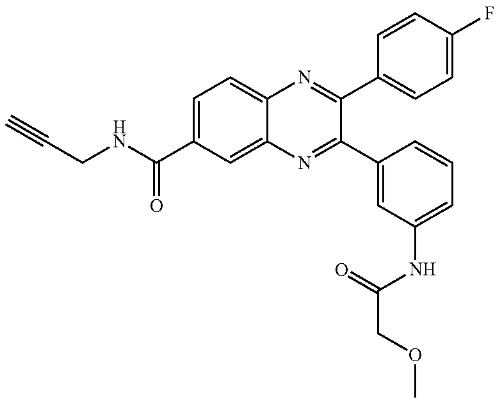

-continued
BC20214
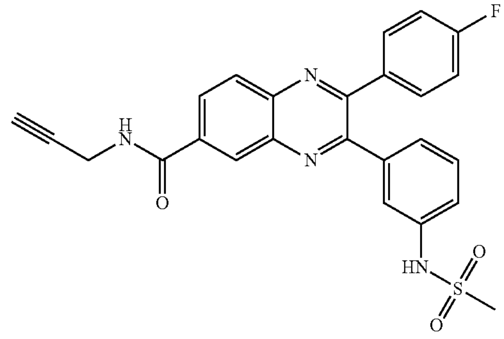
BC20215
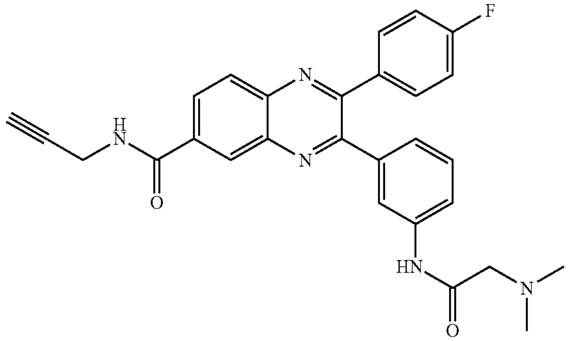
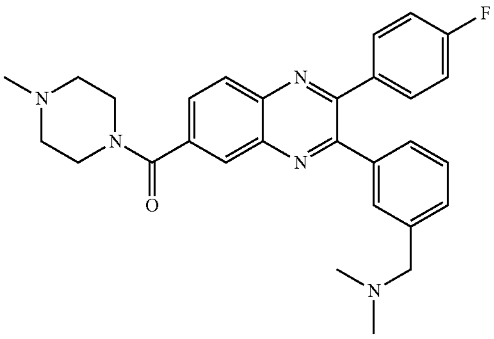
BC20220
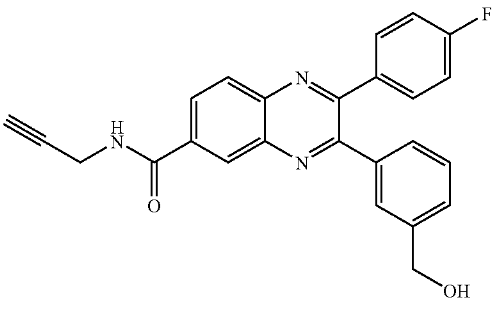
-continued
BC20221
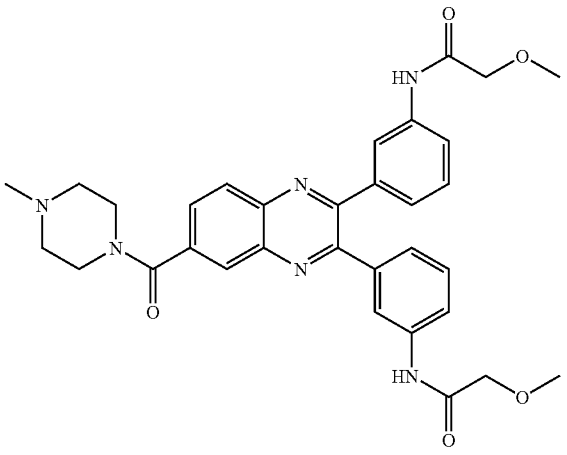
BC20222
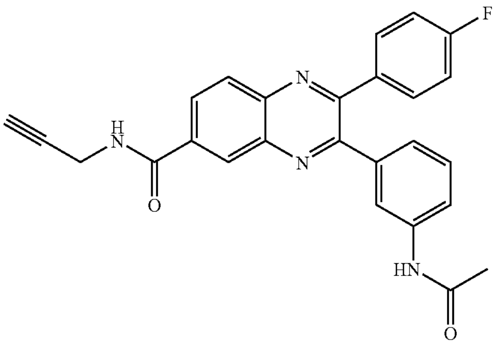
BC20223
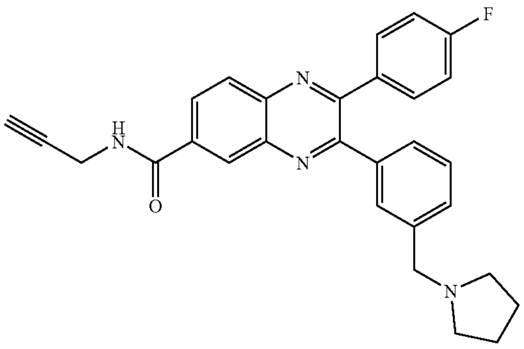

BC20227
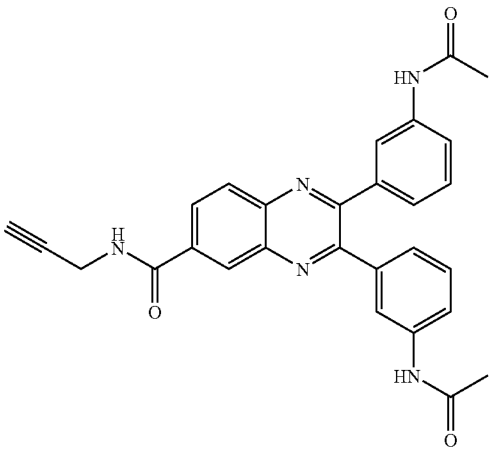
BC20228
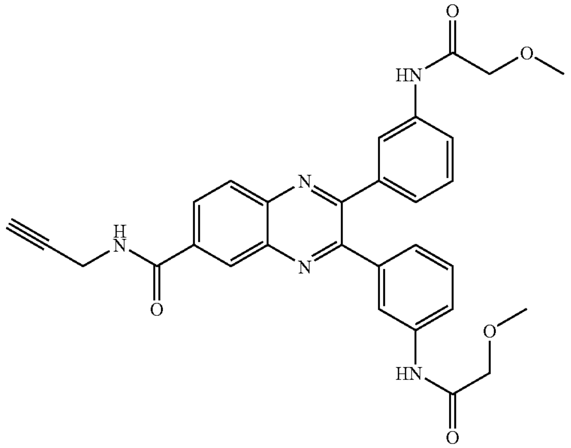
BC20229
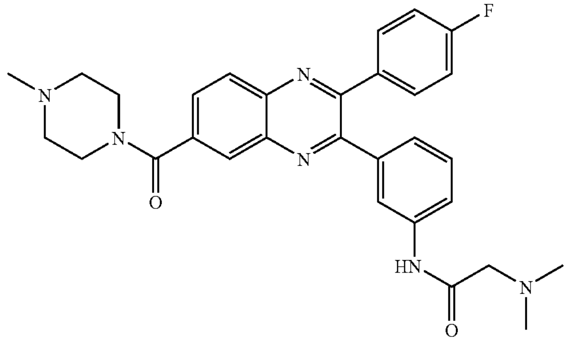
BC20230
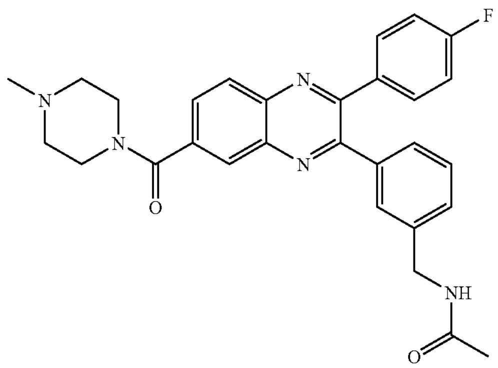
BC20231
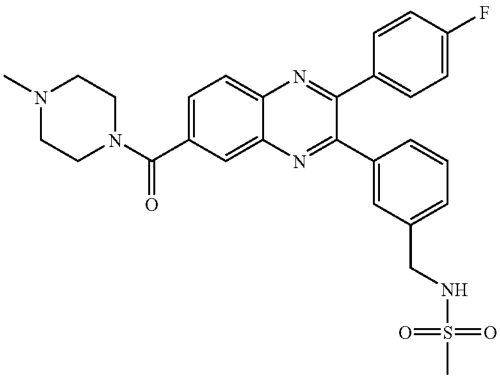
BC20232
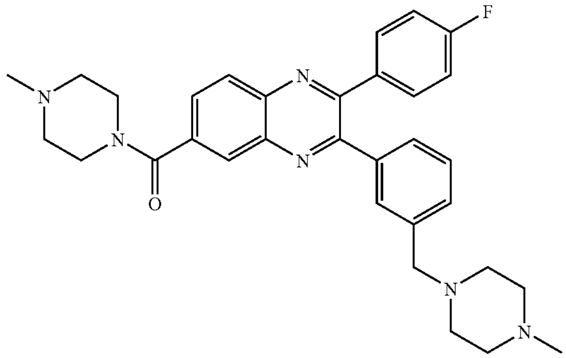
BC20233
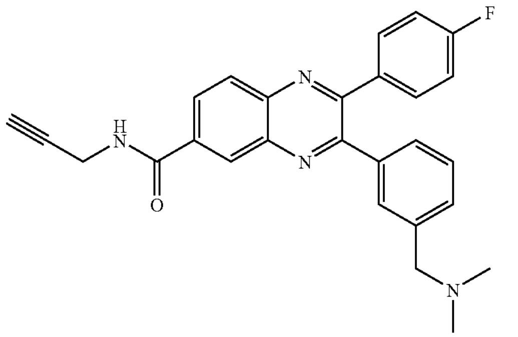

-continued
BC20234
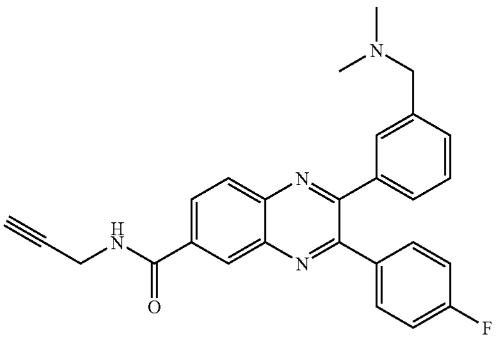
BC20240
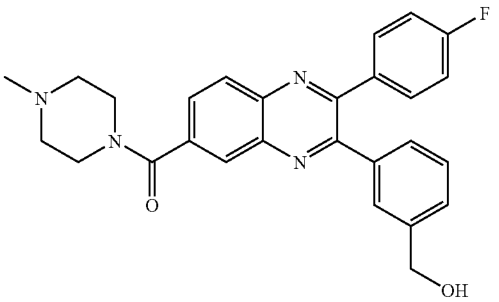
BC20241
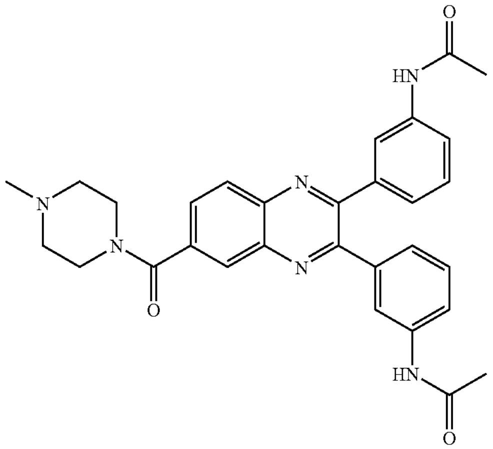
BC20242
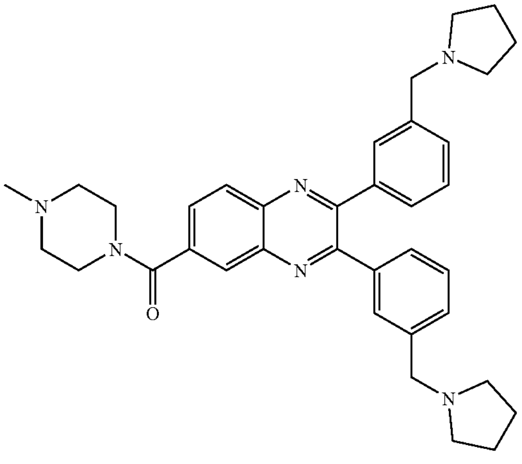
-continued
BC20243
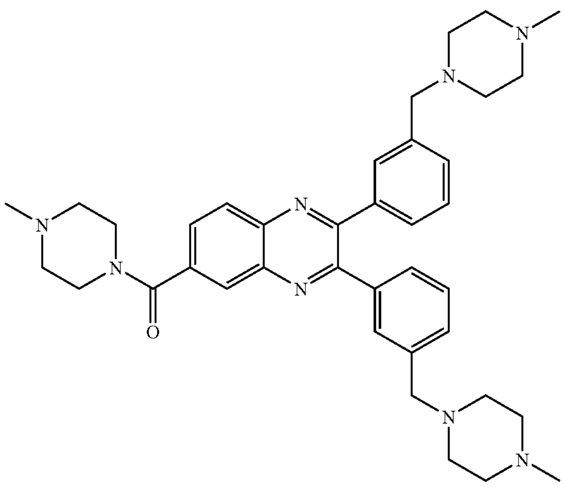
BC20244
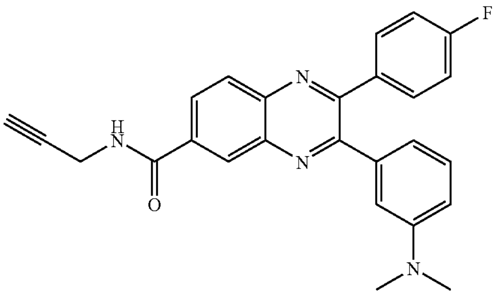
BC20245
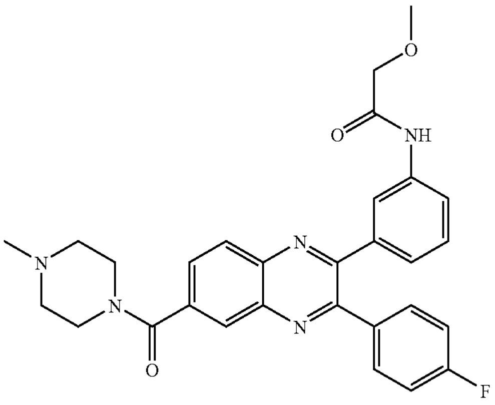
BC20246
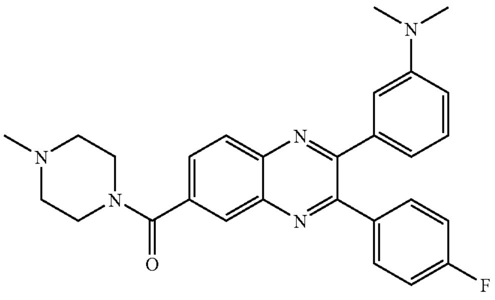

-continued
BC20247
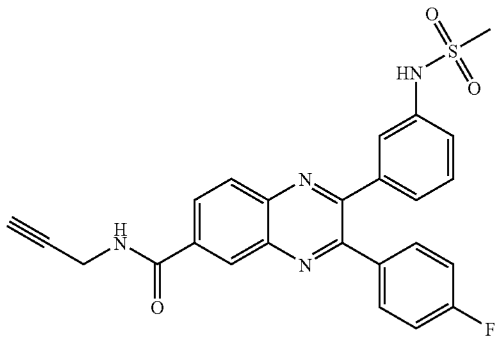
BC20258
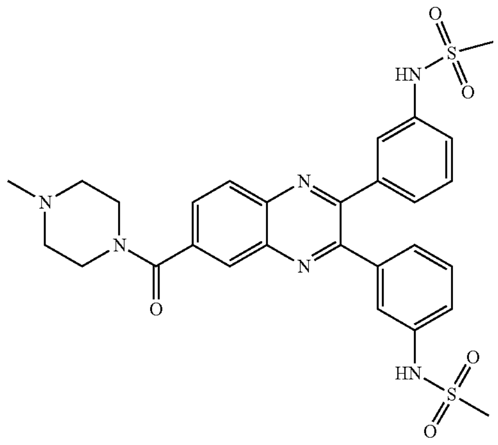
BC20248
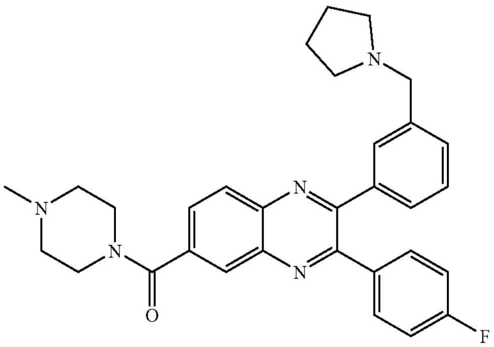
BC20259
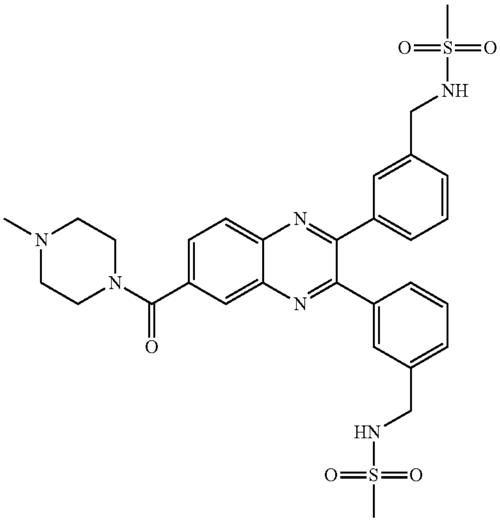
BC20249
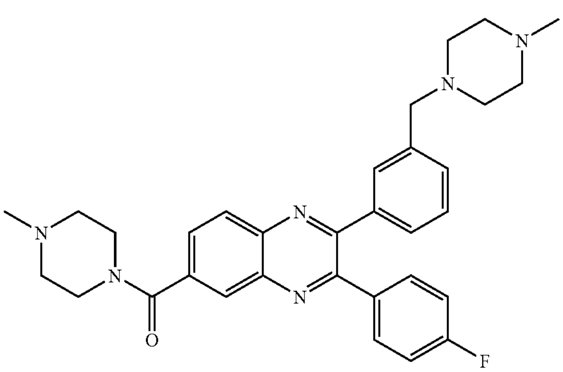
BC20260
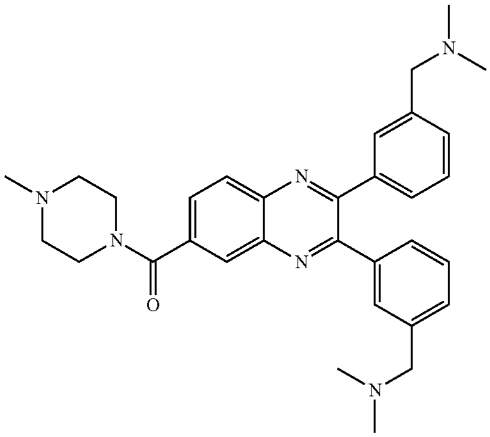

BC20261
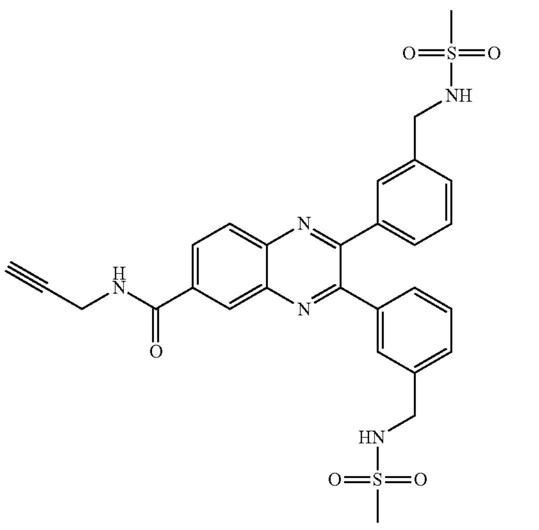
BC20262
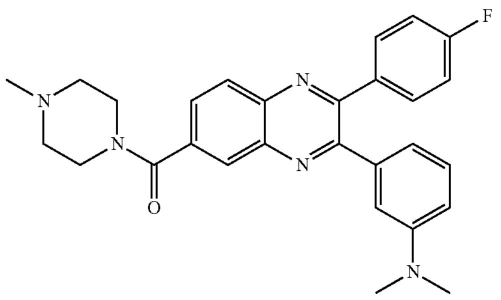
BC20263
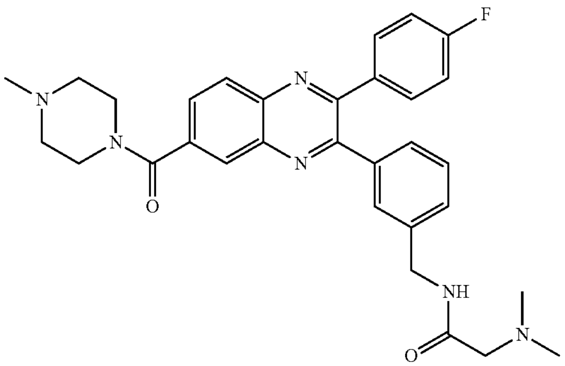
BC20264
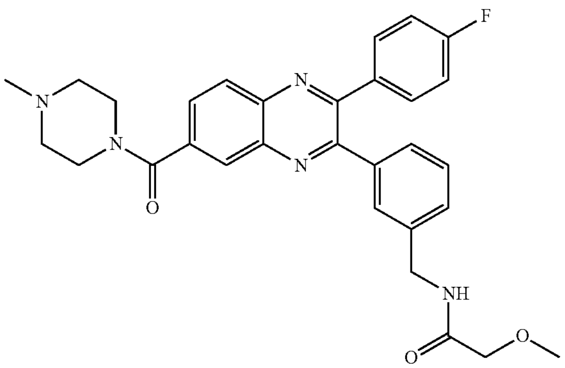
BC20265
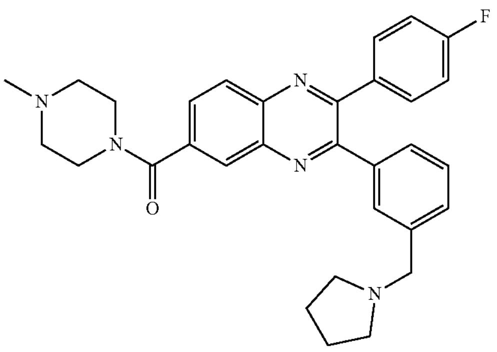
BC20266
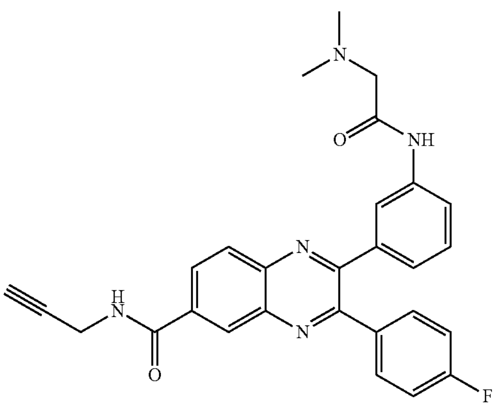
BC20272
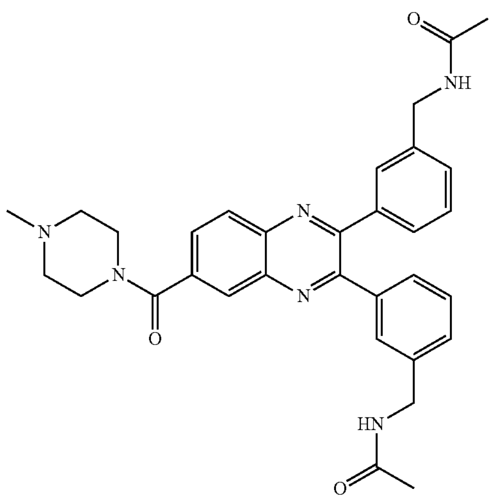

-continued
BC20273
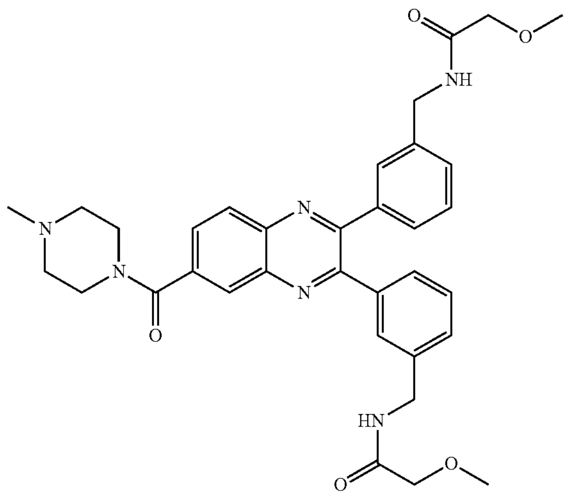
BC20274
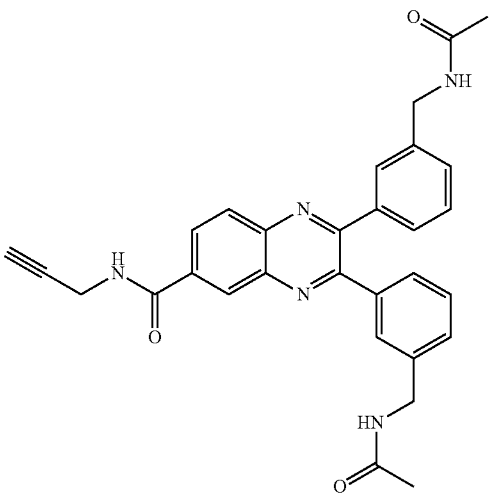
BC20275
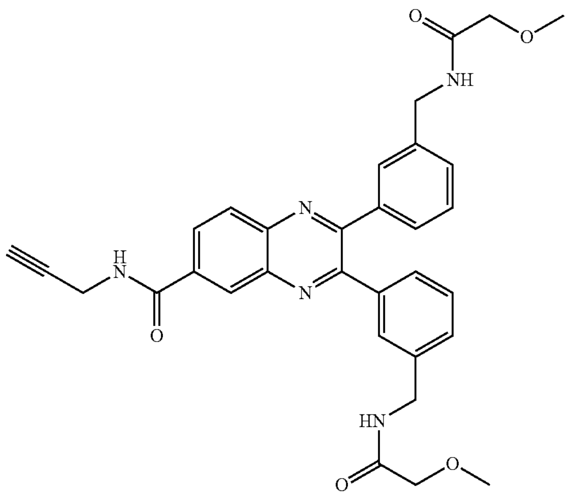
-continued
BC20276
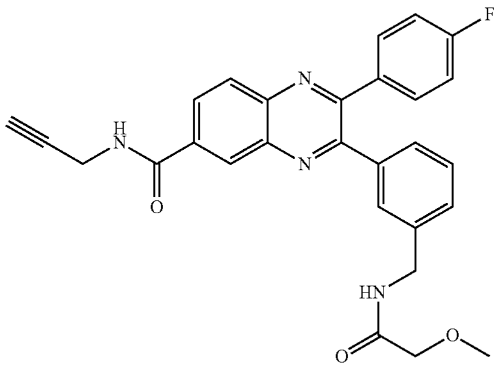
BC20286
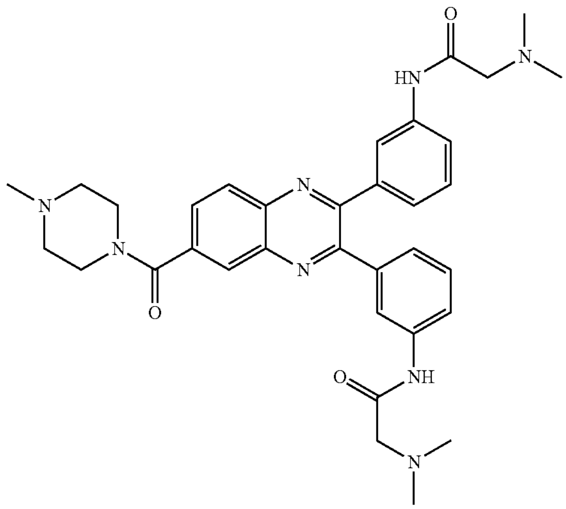
BC20288
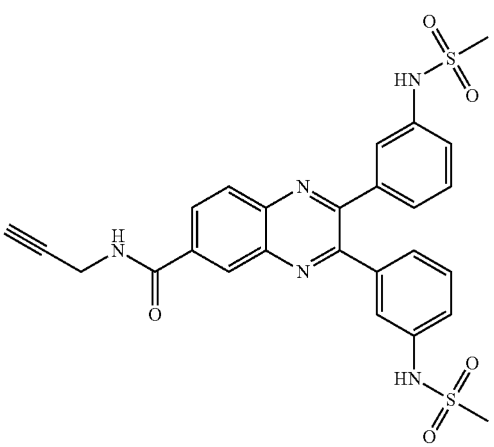

-continued
BC20289
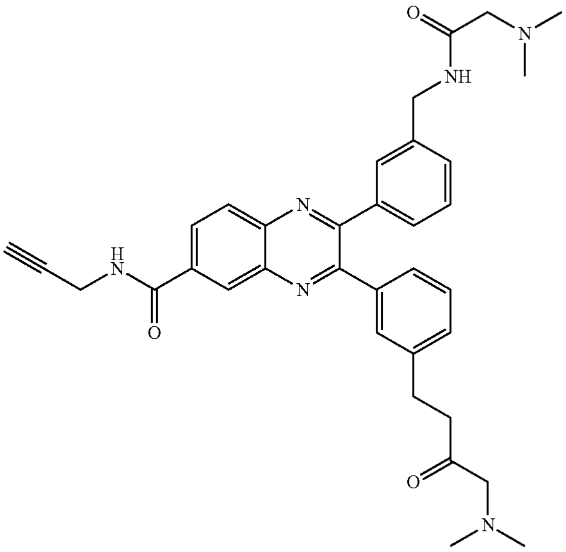
BC20290
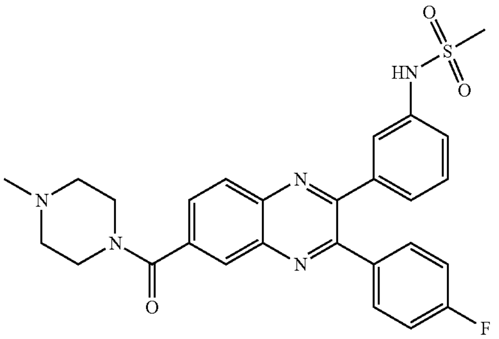
BC20296
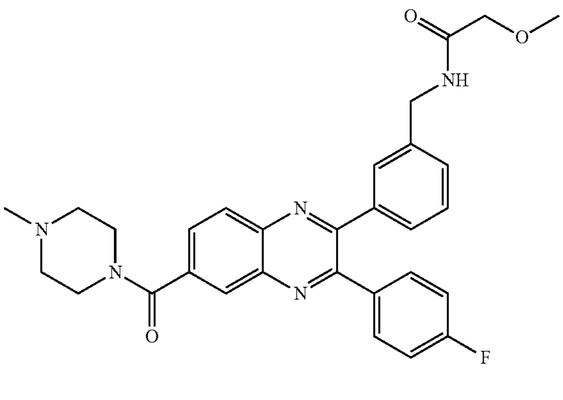
-continued
BC20306
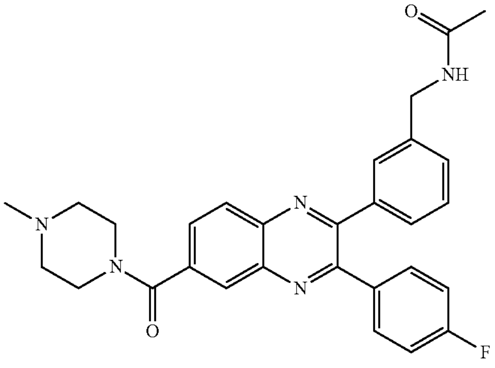
BC20307
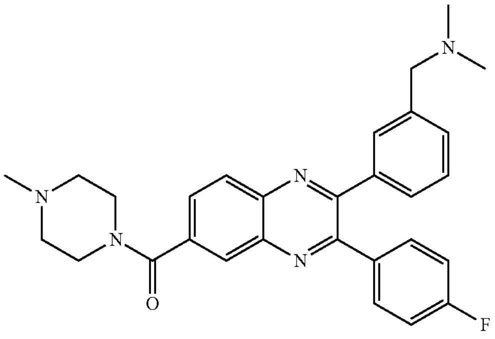
BC20235
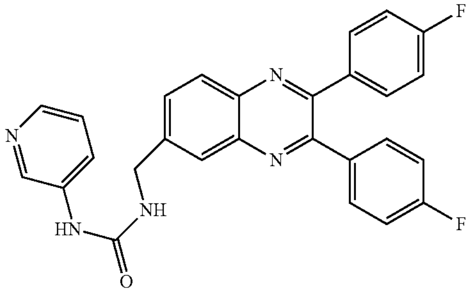
BC20236
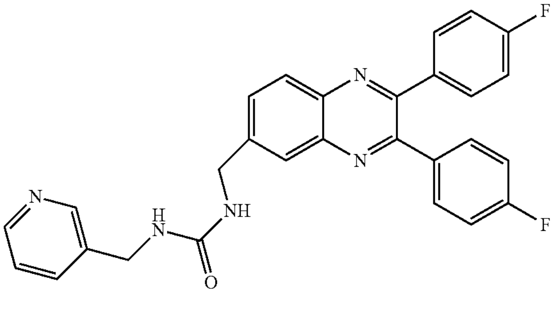

-continued
BC20250
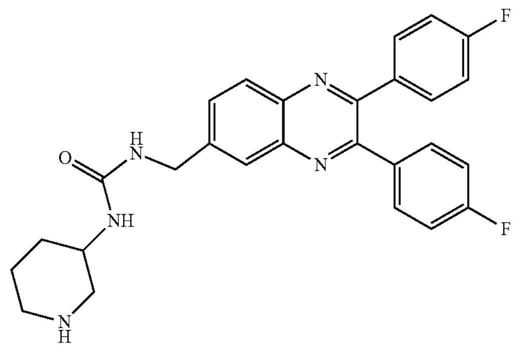
BC20251
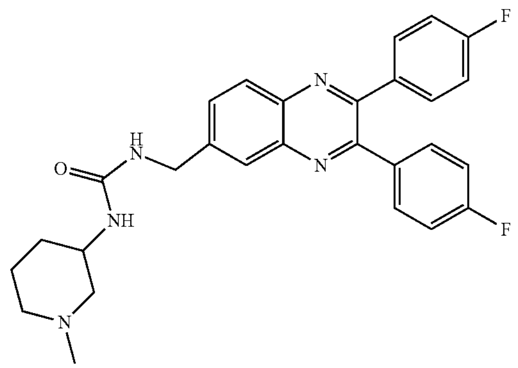
BC20252
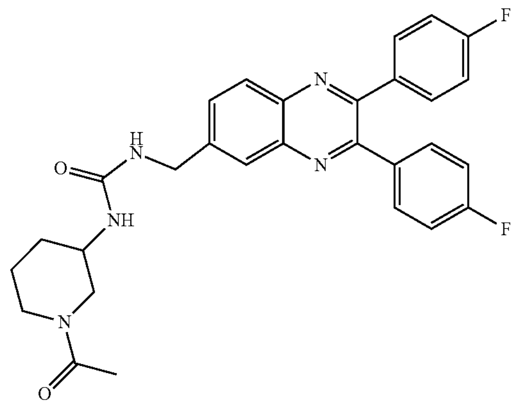
BC20253
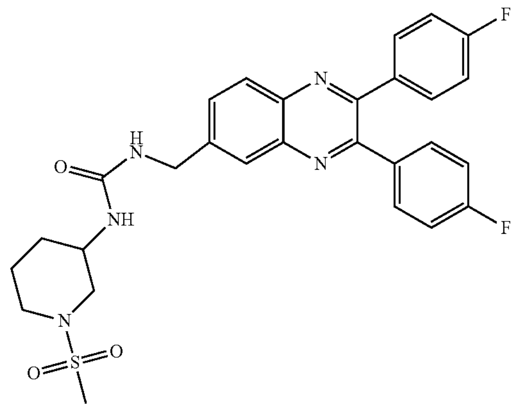
-continued
BC20267
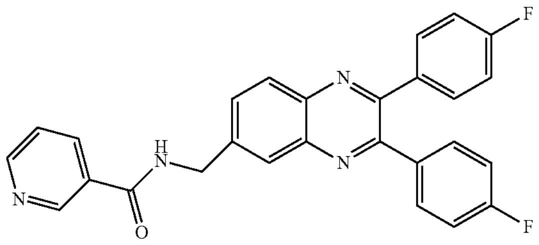
BC20278
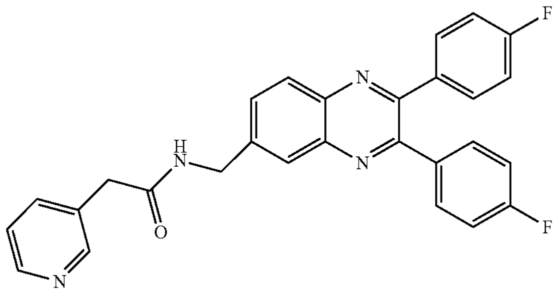
BC20284
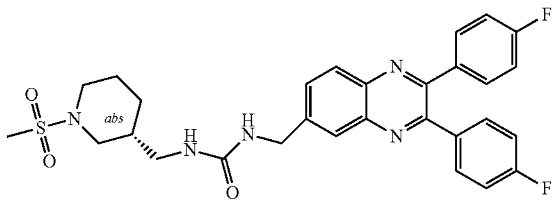
BC20285
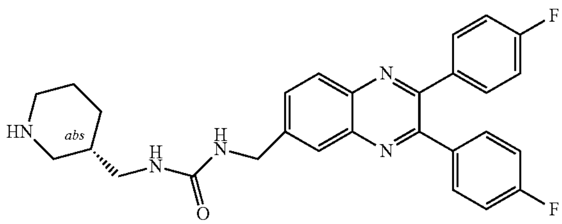
BC20294
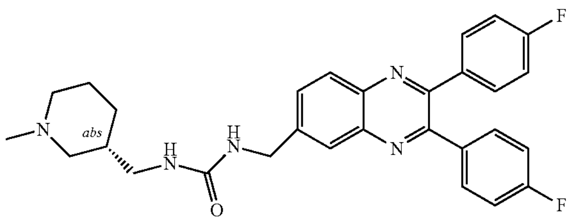
BC20301
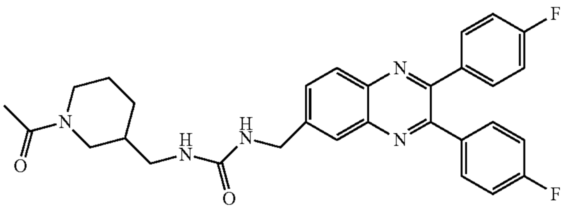

-continued
BC20325
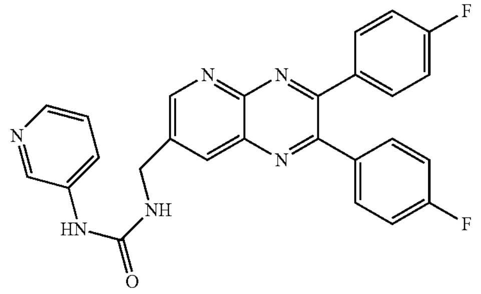
BC20326
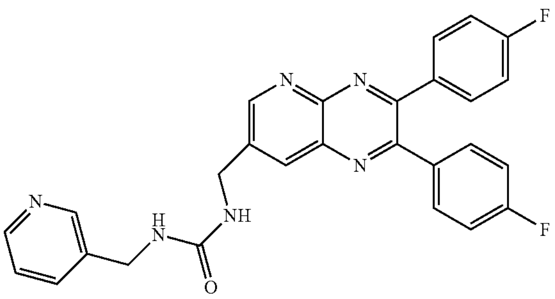
BC20327
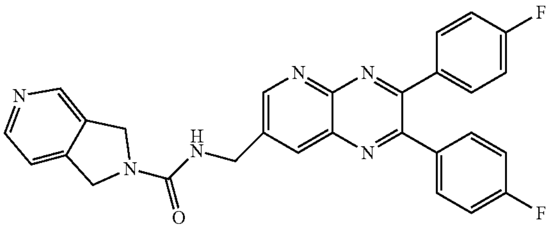
BC20328
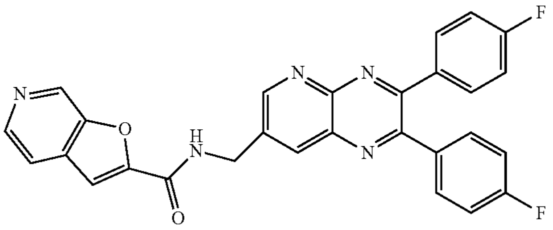
BC20329
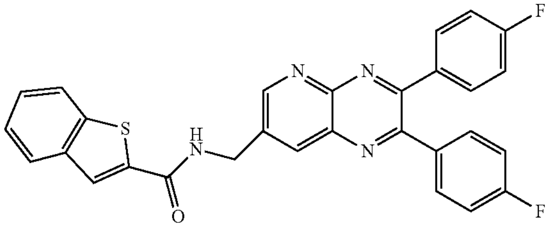
BC20332
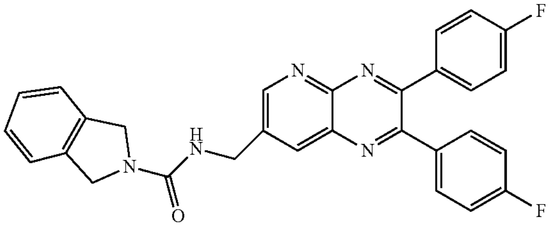
-continued
BC20270
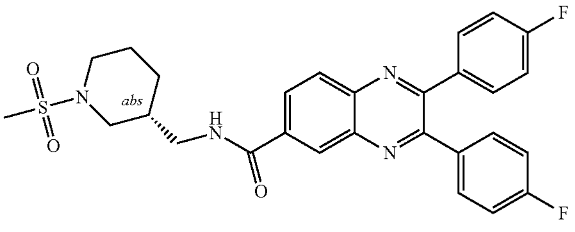
BC20271
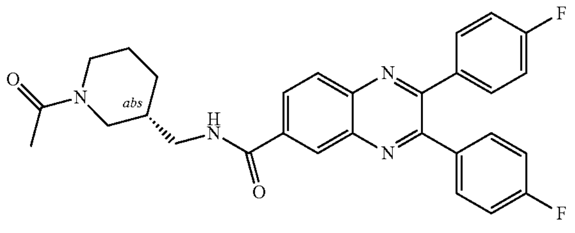
BC20279
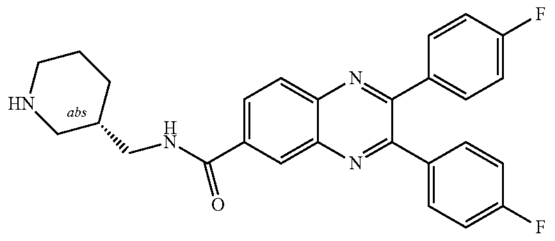
BC20280
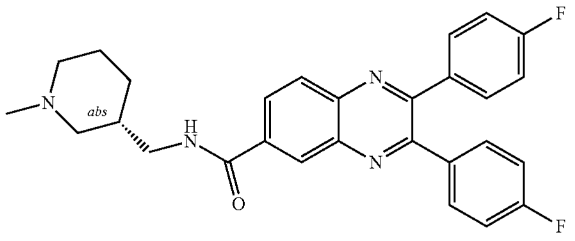
BC20281
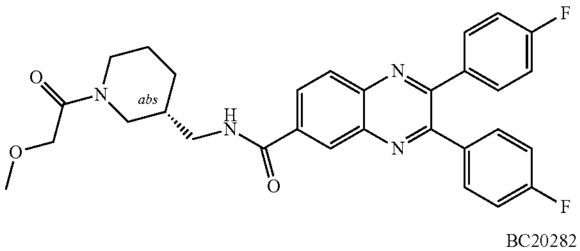
BC20282
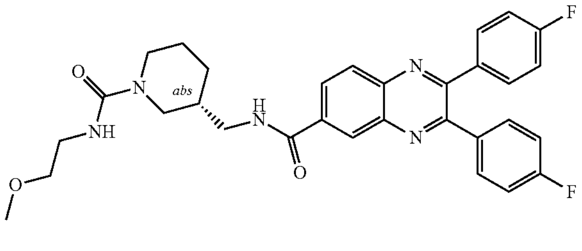

-continued
BC20283
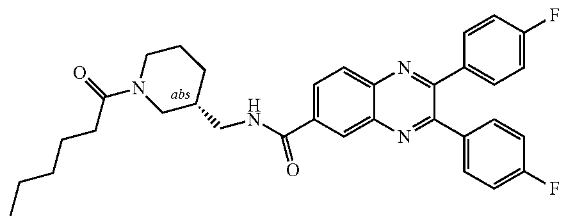
BC20292
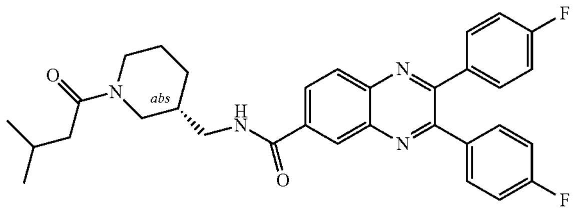
BC20295
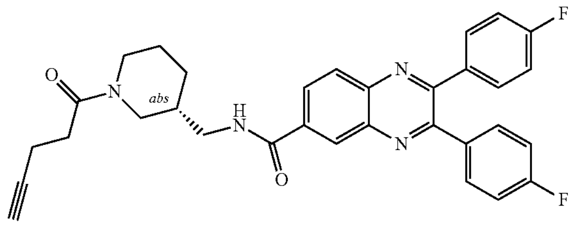
BC20309
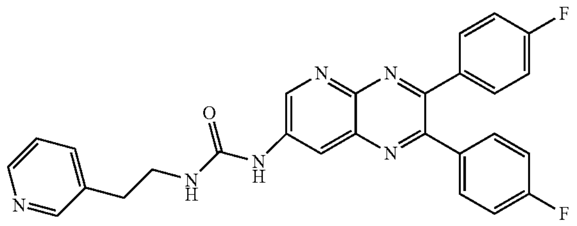
-continued
BC20322
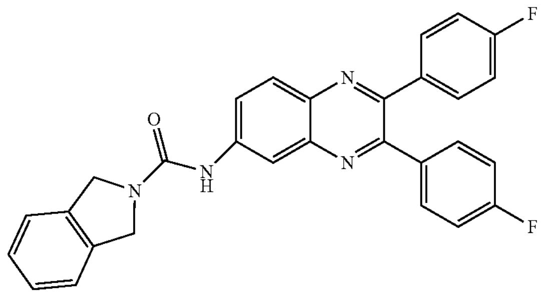
BC20323
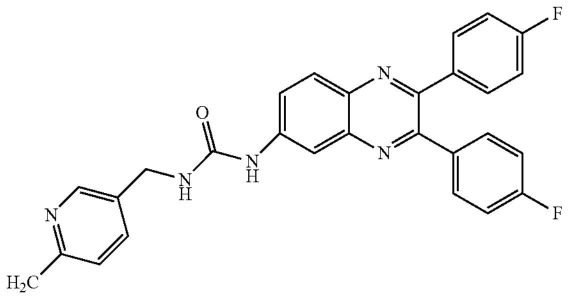
BC20324
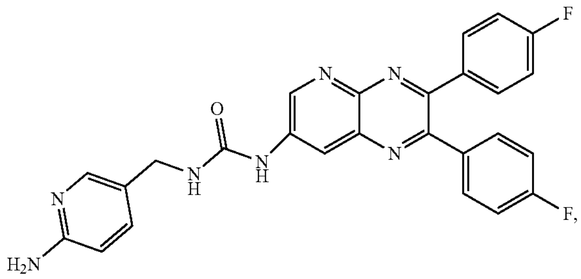
or a pharmaceutically acceptable salt thereof.
* * * * *